US012767704B2

(12) United States Patent
Sok et al.

(10) Patent No.: US 12,767,704 B2
(45) Date of Patent: Oct. 20, 2026

(54) ANTIBODIES CAPABLE OF BINDING HIV GP120 AND METHODS OF USE THEREOF

(71) Applicants: International AIDS Vaccine Initiative, New York, NY (US); The Scripps Research Institute, La Jolla, CA (US)

(72) Inventors: Devin Sok, New York, NY (US); Dennis R. Burton, La Jolla, CA (US); Joseph G. Jardine, La Jolla, CA (US)

(73) Assignees: INTERNATIONAL AIDS VACCINE INITIATIVE, New York, NY (US); THE SCRIPPS RESEARCH INSTITUTE, La Jolla, CA (US)

(*) Notice: Subject to any disclaimer, the term of this patent is extended or adjusted under 35 U.S.C. 154(b) by 1101 days.

(21) Appl. No.: 17/772,561

(22) PCT Filed: Oct. 29, 2020

(86) PCT No.: PCT/US2020/057816

§ 371 (c)(1),
(2) Date: Apr. 28, 2022

(87) PCT Pub. No.: WO2021/087015

PCT Pub. Date: May 6, 2021

(65) Prior Publication Data

US 2023/0134571 A1 May 4, 2023

Related U.S. Application Data

(60) Provisional application No. 62/927,239, filed on Oct. 29, 2019.

(51) Int. Cl.
*C07K 16/114* (2026.01)
*A61P 31/18* (2006.01)

(52) U.S. Cl.
CPC ............ *C07K 16/114* (2026.01); *A61P 31/18* (2018.01); *C07K 2317/31* (2013.01); *C07K 2317/565* (2013.01); *C07K 2317/567* (2013.01); *C07K 2317/76* (2013.01); *C07K 2317/92* (2013.01)

(58) Field of Classification Search
CPC ............ C07K 16/1045; C07K 2317/31; C07K 2317/565; C07K 2317/567; C07K 2317/76; C07K 2317/92; C07K 2317/21; C07K 2317/33; A61P 31/18; A61K 39/42; A61K 2039/505
See application file for complete search history.

(56) References Cited

U.S. PATENT DOCUMENTS

| | | | |
|---|---|---|---|
| 8,673,307 B1 | 3/2014 | Nussenssweig et al. |
| 10,093,720 B2 | 10/2018 | Burton et al. |
| 2011/0044995 A1 | 2/2011 | Matsushita et al. |
| 2015/0361160 A1 | 12/2015 | Burton et al. |
| 2019/0031742 A1 | 1/2019 | Chan-Hui et al. |

FOREIGN PATENT DOCUMENTS

| | | |
|---|---|---|
| EP | 0462551 B1 | 12/1991 |
| WO | 2017096221 A1 | 6/2017 |
| WO | 2018237357 | 12/2018 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*
Joseph G. Jardine, Supplementary Materials for "HIV-1 broadly neutralizing antibody precursor B cells revealed by germline-targeting immunogen", Science, Mar. 25, 2016, 351(6280), 1458-1463.
Salar N. Khan, "Targeting the HIV-1 Spike and Coreceptor with Bi- and Trispecific Antibodies for Single-Component Broad Inhibition of Entry", Journal of Virology, Sep. 2018, vol. 92, Issue 18, 19 pages.
Liang Wei-Ching et al., "Dramatic activation of an antibody by a single amino acid change in framework", Scientific Reports, vol. 11, No. 1, Nov. 16, 2021 (Nov. 16, 2021), XP093221801.
International Search Report for PCT/US2020/057816, mailed Mar. 8, 2021.
Written Opinion of the International Searching Authority for PCT/US2020/057816, mailed Mar. 22, 2021.
Third Party Observation submitted in PCT/US2020/057816 on Feb. 28, 2022.
Walker, L.M. et al., "Passive Immunotherapy of Viral Infections: Super-Antibodies Enter the Fray," Nature Reviews Immunology, vol. 18, No. 5, pp. 297-308, Jan. 30, 2018.
Rudicell, R. et al., "Enhanced Potency of a Broadly neutralizing HIV-1 Antibody In Vitro Improves Protection Against Lentiviral Infection In Vivo," The Journal of Virology, vol. 88, No. 21, pp. 12669-12682, Aug. 20, 2014.

(Continued)

*Primary Examiner* — Robert S Landsman
(74) *Attorney, Agent, or Firm* — Nixon & Vanderhye, PC

(57) ABSTRACT

The present disclosure relates to anti-HIV Env antibodies and their use in the treatment or prevention of HIV/AIDS. In one aspect, provided herein are enhanced engineered anti-HIV Env antibodies that were derived from the PGDM1400 parent antibody using directed-evolution and yeast display. In one aspect, provided herein are pharmaceutical compositions comprising the enhanced engineered anti-HIV Env antibodies disclosed herein.

17 Claims, 1 Drawing Sheet

Specification includes a Sequence Listing.

(56) References Cited

OTHER PUBLICATIONS

Grobben et al., "The potential of engineered antibodies for HIV-1 therapy and cure," Current Opinion in Virology, 38:70-80, Aug. 15, 2019.

* cited by examiner

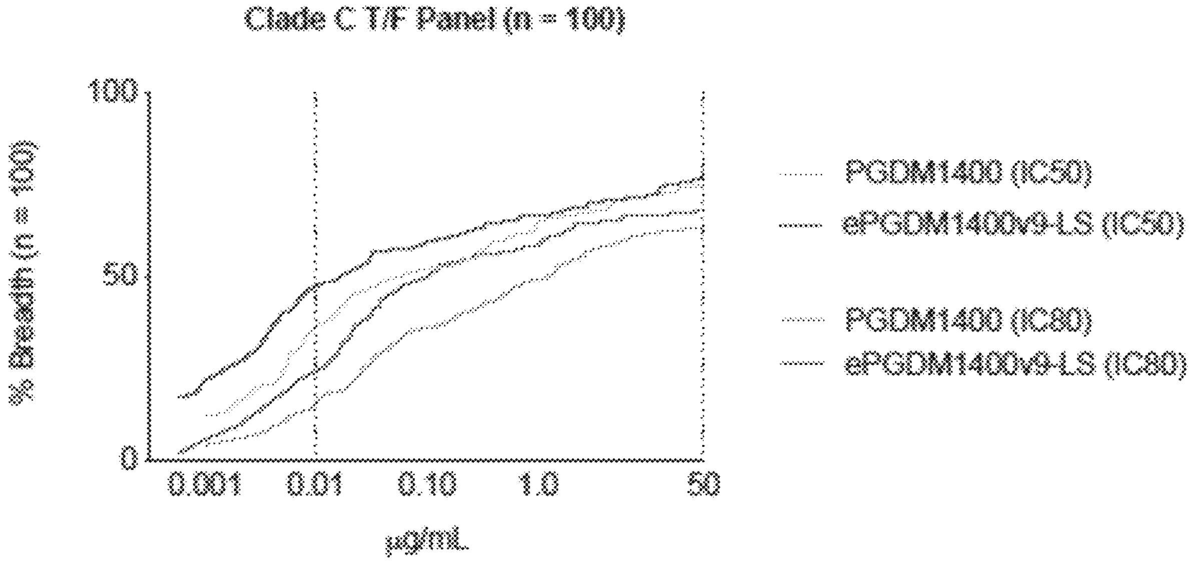
Clade C T/F Panel (n = 100)
% Breadth (n = 100)
100
50
0
0.001
0.01
0.10
1.0
50
μg/mL
PGDM1400 (IC50)
ePGDM1400v9-LS (IC50)
PGDM1400 (IC80)
ePGDM1400v9-LS (IC80)

SEQUENCE LISTING

<160> NUMBER OF SEQ ID NOS: 114

<210> SEQ ID NO 1
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 1

```
Gln Val His Leu Thr Gln Ser Gly Pro Glu Val Arg Lys Pro Gly Thr
1               5                   10                  15

Ser Val Lys Val Ser Cys Lys Ala Pro Gly Asn Thr Leu Lys Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Asn Trp Ala Val Asp Val Asp Tyr Leu Ser Asn Leu
        115                 120                 125

Glu Phe Trp Gly Gln Gly Thr Ala Val Thr Val Ser Ser
    130                 135                 140
```

<210> SEQ ID NO 2
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 2

```
Asp Phe Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110
```

<210> SEQ ID NO 3
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 3

Gln Val Gln Leu Val Gln Ser Gly Ala Glu Val Arg Lys Pro Gly Ala
1 5 10 15

Ser Val Lys Val Ser Cys Lys Asn Pro Gly Asn Thr Leu Thr Thr Tyr
20 25 30

Asp Leu His Trp Val Arg Gln Val Pro Gly Gln Gly Leu Gln Trp Met
35 40 45

Gly Trp Ile Ser His Glu Gly Asp Lys Lys Val Ile Val Glu Arg Phe
50 55 60

Lys Ala Lys Val Asp Ile Asp Trp Asp Arg Ser Thr Asn Thr Ala Tyr
65 70 75 80

Leu Gln Leu Ser Gly Leu Thr Ser Glu Asp Thr Ala Val Tyr Tyr Cys
85 90 95

Ala Lys Gly Ser Lys His Arg Leu Arg Asp Tyr Ala Leu Tyr Asp Glu
100 105 110

Asp Gly Ala Leu Glu Trp Ala Val Asp Val Asp Tyr Leu Ala Asn Leu
115 120 125

Glu Phe Trp Gly Gln Gly Thr Ala Val Thr Val Ser Ser
130 135 140

<210> SEQ ID NO 4
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 4

Gln Ala Gln Leu Val Gln Ser Gly Ala Glu Val Arg Lys Pro Gly Ala
1 5 10 15

Ser Val Lys Val Ser Cys Lys Asn Pro Gly Asn Thr Leu Thr Thr Tyr
20 25 30

Asp Leu His Trp Val Arg Ser Val Pro Gly Gln Gly Leu Glu Trp Met
35 40 45

Gly Trp Ile Ser His Glu Gly Asp Lys Lys Val Ile Ala Glu Arg Phe
50 55 60

Lys Ala Lys Val Asp Ile Asp Trp Asp Arg Ser Thr Asn Thr Ala Tyr
65 70 75 80

Leu Gly Leu Ser Gly Leu Thr Ser Glu Asp Thr Ala Val Tyr Tyr Cys
85 90 95

Ala Lys Gly Ser Lys His Arg Leu Arg Asp Tyr Ala Leu Tyr Asp Glu
100 105 110

Asp Gly Ala Leu Glu Trp Ala Glu Asp Val Asp Tyr Leu Ala Asn Leu
115 120 125

Glu Phe Trp Gly Gln Gly Thr Ala Val Thr Val Ser Ser
130 135 140

<210> SEQ ID NO 5
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 5

Gln Val Gln Leu Val Gln Ser Gly Pro Glu Val Arg Lys Pro Gly Ala
1 5 10 15

Ser Val Lys Val Ser Cys Lys Asn Pro Gly Asn Thr Leu Thr Thr Tyr

```
            20                  25                  30

Asp Leu His Trp Val Arg Gln Val Pro Gly Gln Gly Leu Gln Trp Met
        35                  40                  45

Gly Trp Ile Ser His Glu Gly Asp Lys Lys Val Ile Val Glu Lys Phe
    50                  55                  60

Lys Ala Lys Val Asp Ile Asp Trp Asp Arg Ser Thr Asn Thr Ala Tyr
65                  70                  75                  80

Leu Gln Leu Ser Gly Leu Thr Ser Glu Asp Thr Ala Val Tyr Tyr Cys
                85                  90                  95

Ala Lys Gly Ser Lys His Arg Leu Arg Asp Tyr Ala Leu Tyr Asp Glu
            100                 105                 110

Asp Gly Ala Leu Glu Trp Ala Glu Asp Val Asp Tyr Leu Ala Asn Leu
        115                 120                 125

Glu Phe Trp Gly Gln Gly Thr Ala Val Thr Val Ser Ser
    130                 135                 140


<210> SEQ ID NO 6
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 6

Gln Val Gln Leu Val Gln Ser Gly Pro Glu Val Arg Lys Pro Gly Thr
1               5                   10                  15

Ser Val Lys Val Ser Cys Lys Asn Pro Gly Asn Thr Leu Thr Thr Tyr
            20                  25                  30

Asp Leu His Trp Val Arg Gln Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Asp Ile Asp Trp Asp Arg Ser Thr Asn Thr Ala Tyr
65                  70                  75                  80

Leu Gly Leu Ser Gly Leu Thr Ser Glu Asp Thr Ala Val Tyr Tyr Cys
                85                  90                  95

Ala Lys Gly Ser Lys His Arg Leu Arg Asp Tyr Ala Leu Tyr Asp Asp
            100                 105                 110

Asp Gly Ala Leu Glu Trp Ala Glu Asp Val Asp Tyr Leu Ala Asn Leu
        115                 120                 125

Glu Phe Trp Gly Gln Gly Thr Ala Val Thr Val Ser Ser
    130                 135                 140


<210> SEQ ID NO 7
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 7

Gln Ala Gln Leu Val Gln Ser Gly Ala Glu Val Arg Lys Pro Gly Thr
1               5                   10                  15

Ser Val Lys Val Ser Cys Lys Asn Pro Gly Asn Thr Leu Thr Thr Tyr
            20                  25                  30

Asp Leu His Trp Val Arg Ser Val Pro Gly Gln Gly Leu Glu Trp Met
        35                  40                  45
```

```
Gly Trp Ile Ser His Glu Gly Asp Lys Lys Glu Ile Val Glu Arg Phe
    50                  55                  60

Lys Ala Lys Val Asp Ile Asp Trp Asp Arg Ser Thr Asn Thr Ala Tyr
65                  70                  75                  80

Leu Gln Leu Ser Gly Leu Thr Ser Glu Asp Thr Ala Val Tyr Tyr Cys
                85                  90                  95

Ala Lys Gly Ser Lys His Arg Leu Arg Asp Tyr Ala Leu Tyr Asp Glu
            100                 105                 110

Asp Gly Ala Leu Asn Trp Ala Val Asp Val Asp Tyr Leu Ala Asn Leu
        115                 120                 125

Glu Phe Trp Gly Gln Gly Thr Ala Val Thr Val Ser Ser
    130                 135                 140


<210> SEQ ID NO 8
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 8

Gln Val Gln Leu Val Gln Ser Gly Pro Glu Val Arg Lys Pro Gly Ala
1               5                   10                  15

Ser Val Lys Val Ser Cys Lys Asn Pro Gly Asn Thr Leu Thr Thr Tyr
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Asp Ile Asp Trp Asp Arg Ser Thr Asn Thr Ala Tyr
65                  70                  75                  80

Leu Gln Leu Ser Gly Leu Thr Ser Glu Asp Thr Ala Val Tyr Tyr Cys
                85                  90                  95

Ala Lys Gly Ser Lys His Arg Leu Arg Asp Tyr Ala Leu Tyr Asp Glu
            100                 105                 110

Asp Gly Ala Leu Glu Tyr Ala Glu Asp Val Asp Tyr Leu Ala Asn Leu
        115                 120                 125

Glu Phe Trp Gly Gln Gly Thr Ala Val Thr Val Ser Ser
    130                 135                 140


<210> SEQ ID NO 9
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 9

Gln Ala Gln Leu Val Gln Ser Gly Pro Glu Val Arg Lys Pro Gly Thr
1               5                   10                  15

Ser Val Lys Val Ser Cys Lys Asn Pro Gly Asn Thr Leu Thr Thr Tyr
            20                  25                  30

Asp Leu His Trp Val Arg Gln Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80
```

Leu Gln Leu Ser Gly Leu Thr Ser Glu Asp Thr Ala Val Tyr Tyr Cys
85 90 95

Ala Lys Gly Ser Lys His Arg Leu Arg Asp Tyr Ala Leu Tyr Asp Glu
100 105 110

Asp Gly Ala Leu Asn Trp Ala Val Asp Val Asp Tyr Leu Ala Asn Leu
115 120 125

Glu Phe Trp Gly Gln Gly Thr Ala Val Thr Val Ser Ser
130 135 140

<210> SEQ ID NO 10
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 10

Gln Ala Gln Leu Val Gln Ser Gly Ala Glu Val Arg Lys Pro Gly Thr
1 5 10 15

Ser Val Lys Val Ser Cys Lys Asn Pro Gly Asn Thr Leu Thr Thr Tyr
20 25 30

Asp Leu His Trp Val Arg Gln Val Pro Gly Gln Gly Leu Gln Trp Met
35 40 45

Gly Trp Ile Ser His Glu Gly Asp Lys Lys Val Ile Val Glu Arg Phe
50 55 60

Gln Gly Arg Val Asp Ile Asp Trp Asp Arg Ser Thr Asn Thr Ala Tyr
65 70 75 80

Leu Gln Leu Ser Gly Leu Thr Ser Glu Asp Thr Ala Val Tyr Tyr Cys
85 90 95

Ala Lys Gly Ser Lys His Arg Leu Arg Asp Tyr Ala Leu Tyr Asp Glu
100 105 110

Asp Gly Ala Leu Asn Trp Ala Val Asp Val Asp Tyr Leu Ala Asn Leu
115 120 125

Glu Phe Trp Gly Gln Gly Thr Ala Val Thr Val Ser Ser
130 135 140

<210> SEQ ID NO 11
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 11

Gln Ala Gln Leu Val Gln Ser Gly Pro Glu Val Arg Lys Pro Gly Thr
1 5 10 15

Ser Val Lys Val Ser Cys Lys Asn Pro Gly Asn Thr Leu Thr Thr Tyr
20 25 30

Asp Leu His Trp Val Arg Gln Val Pro Gly Gln Gly Leu Glu Trp Met
35 40 45

Gly Trp Ile Ser His Glu Gly Asp Gln Lys Val Ile Val Glu Lys Phe
50 55 60

Lys Ala Lys Val Asp Ile Asp Trp Asp Arg Ser Thr Asn Thr Ala Tyr
65 70 75 80

Leu Gln Leu Ser Gly Leu Thr Ser Glu Asp Thr Ala Val Tyr Tyr Cys
85 90 95

Ala Lys Gly Ser Lys His Arg Leu Arg Asp Tyr Ala Leu Tyr Asp Glu

```
            100                 105                 110

Asp Gly Ala Leu Glu Trp Ala Val Asp Val Asp Tyr Leu Ala Asn Leu
        115                 120                 125

Glu Phe Trp Gly Gln Gly Thr Ala Val Thr Val Ser Ser
    130                 135                 140


<210> SEQ ID NO 12
<211> LENGTH: 141
<212> TYPE: PRT
<213> ORGANISM: Artificial Sequence
<220> FEATURE:
<223> OTHER INFORMATION: Recombinantly produced polypeptide

<400> SEQUENCE: 12

Gln Val Gln Leu Val Gln Ser Gly Pro Glu Val Arg Lys Pro Gly Thr
1               5                   10                  15

Ser Val Lys Val Ser Cys Lys Asn Pro Gly Asn Thr Leu Thr Thr Tyr
            20                  25                  30

Asp Leu His Trp Val Arg Gln Val Pro Gly Gln Gly Leu Gln Trp Met
        35                  40                  45

Gly Trp Ile Ser His Glu Gly Asp Gln Lys Val Ile Val Glu Arg Phe
    50                  55                  60

Lys Ala Lys Val Asp Ile Asp Trp Asp Arg Ser Thr Asn Thr Ala Tyr
65                  70                  75                  80

Leu Gln Leu Ser Gly Leu Thr Ser Glu Asp Thr Ala Val Tyr Tyr Cys
                85                  90                  95

Ala Lys Gly Ser Lys His Arg Leu Arg Asp Tyr Ala Leu Tyr Asp Glu
            100                 105                 110

Asp Gly Ala Leu Asn Trp Ala Val Asp Val Asp Tyr Leu Ala Asn Leu
        115                 120                 125

Glu Phe Trp Gly Gln Gly Thr Ala Val Thr Val Ser Ser
    130                 135                 140


<210> SEQ ID NO 13
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 13

Asp Ile Val Leu Thr Gln Ser Pro Leu Ser Leu Ser Val Thr Pro Gly
1               5                   10                  15

Glu Ser Ala Ser Ile Ser Cys Lys Ser Asp Gln Ser Leu Gln His Gly
            20                  25                  30

Asp Arg Asn Asn Tyr Leu Ala Trp Tyr Val Gln Lys Pro Gly Lys Ser
        35                  40                  45

Pro Gln Leu Leu Ile Asp Leu Ala Ser Glu Arg Ala Ser Gly Val Pro
    50                  55                  60

Asp Arg Phe Ser Gly Ser Gly Ser Glu Lys Asp Phe Thr Leu Lys Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 14
<211> LENGTH: 112
```

<212> TYPE: PRT
<213> ORGANISM: Artificial Sequence
<220> FEATURE:
<223> OTHER INFORMATION: Recombinantly produced polypeptide

<400> SEQUENCE: 14

```
Asp Ile Val Leu Thr Gln Ser Pro Leu Ser Leu Ser Val Thr Pro Gly
1               5                   10                  15

Glu Ser Ala Ser Ile Ser Cys Lys Ser Ser Gln Ser Leu Gln His Gly
            20                  25                  30

Asp Arg Asn Asn Tyr Leu Ala Trp Tyr Leu Gln Lys Pro Gly Lys Ser
        35                  40                  45

Pro Gln Leu Leu Leu Asp Leu Gly Ser Asp Arg Ala Ser Gly Val Pro
    50                  55                  60

Asp Arg Phe Ser Gly Ser Gly Ser Arg Lys Asp Phe Thr Leu Ser Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110
```

<210> SEQ ID NO 15
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 15

```
Asp Ile Val Leu Thr Gln Ser Pro His Ser Leu Ser Val Thr Pro Gly
1               5                   10                  15

Glu Pro Ala Ser Ile Ser Cys Lys Ser Ser Gln Ser Leu Leu His Gly
            20                  25                  30

Asp Arg Asn Asn Tyr Leu Ala Trp Tyr Val Gln Lys Pro Gly Arg Ser
        35                  40                  45

Pro Gln Leu Leu Leu Asp Leu Ala Ser Asp Arg Ala Ser Gly Val Pro
    50                  55                  60

Asp Arg Phe Ser Gly Ser Gly Ser Glu Lys Asp Phe Thr Leu Lys Ile
65                  70                  75                  80

Asp Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 16

```
Asp Phe Val Leu Thr Gln Ser Pro Leu Ser Leu Ser Val Thr Pro Gly
1               5                   10                  15

Glu Ser Ala Ser Ile Ser Cys Lys Ser Ser Gln Ser Leu Gln His Gly
            20                  25                  30

Asp Arg Asn Asn Tyr Leu Ala Trp Tyr Val Gln Lys Pro Gly Gln Ser
        35                  40                  45

Pro Gln Leu Leu Ile Asp Leu Ala Ser Asp Arg Ala Ser Gly Val Pro
```

```
    50                  55                  60

Asp Arg Phe Ser Gly Ser Gly Ser Glu Lys Asp Phe Thr Leu Ser Ile
65                  70                  75                  80

Asp Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 17
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 17

Asp Phe Val Leu Thr Gln Ser Pro Leu Ser Leu Ser Val Thr Pro Gly
1               5                   10                  15

Glu Ser Ala Ser Ile Ser Cys Lys Ser Asp His Ser Leu Gln His Gly
            20                  25                  30

Asp Arg Asn Asn Tyr Leu Ala Trp Tyr Val Gln Lys Pro Gly Arg Ser
        35                  40                  45

Pro Gln Leu Leu Ile Asp Leu Ala Ser Glu Arg Ala Ser Gly Val Pro
    50                  55                  60

Asp Arg Phe Ser Gly Ser Gly Ser Arg Lys Asp Phe Thr Leu Lys Ile
65                  70                  75                  80

Asp Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 18
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 18

Asp Ile Val Leu Thr Gln Ser Pro Leu Ser Leu Ser Val Thr Pro Gly
1               5                   10                  15

Glu Ser Ala Ser Ile Ser Cys Lys Ser Asp His Ser Leu Gln His Gly
            20                  25                  30

Asp Arg Asn Asn Tyr Leu Ala Trp Tyr Val Gln Lys Pro Gly Lys Ser
        35                  40                  45

Pro Gln Leu Leu Ile Asp Leu Ala Ser Asp Arg Ala Ser Gly Val Pro
    50                  55                  60

Asp Arg Phe Ser Gly Ser Gly Ser Glu Lys Asp Phe Thr Leu Ser Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 19
<211> LENGTH: 112
<212> TYPE: PRT
<213> ORGANISM: Artificial Sequence
<220> FEATURE:
```

<223> OTHER INFORMATION: Recombinantly produced polypeptide

<400> SEQUENCE: 19

Asp Ile Val Leu Thr Gln Ser Pro Leu Ser Leu Ser Val Thr Pro Gly
1 5 10 15

Glu Ser Ala Ser Ile Ser Cys Lys Ser Ser Gln Ser Leu Gln His Gly
20 25 30

Asp Arg Asn Asn Tyr Leu Ala Trp Tyr Val Gln Lys Pro Gly Arg Ser
35 40 45

Pro Gln Leu Leu Leu Asp Leu Ala Ser Asp Arg Ala Ser Gly Val Pro
50 55 60

Asp Arg Phe Ser Gly Ser Gly Ser Glu Lys Asp Phe Thr Leu Lys Ile
65 70 75 80

Asp Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

<210> SEQ ID NO 20
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 20

Asp Ile Val Leu Thr Gln Ser Pro Leu Ser Leu Ser Val Thr Pro Gly
1 5 10 15

Glu Ser Ala Ser Ile Ser Cys Lys Ser Ser His Ser Leu Gln His Gly
20 25 30

Asp Arg Asn Asn Tyr Leu Ala Trp Tyr Val Gln Lys Pro Gly Gln Ser
35 40 45

Pro Gln Leu Leu Ile Asp Leu Gly Ser Asp Arg Ala Ser Gly Val Pro
50 55 60

Asp Arg Phe Ser Gly Ser Gly Ser Glu Lys Asp Phe Thr Leu Lys Ile
65 70 75 80

Asp Arg Val Glu Ala Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

<210> SEQ ID NO 21
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 21

Asp Ile Val Leu Thr Gln Ser Pro Leu Ser Leu Ser Val Thr Pro Gly
1 5 10 15

Glu Ser Ala Ser Ile Ser Cys Lys Ser Ser Gln Ser Leu Ile His Gly
20 25 30

Asp Arg Asn Asn Tyr Leu Ala Trp Tyr Val Gln Lys Pro Gly Arg Ser
35 40 45

Pro Gln Leu Leu Ile Asp Leu Ala Ser Glu Arg Ala Ser Gly Val Pro
50 55 60

Asp Arg Phe Ser Gly Ser Gly Ser Arg Lys Asp Phe Thr Leu Lys Ile

```
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 22
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 22

Asp Ile Val Leu Thr Gln Ser Pro Leu Ser Leu Ser Val Thr Pro Gly
1               5                   10                  15

Glu Pro Ala Ser Ile Ser Cys Lys Ser Asp Gln Ser Leu Gln His Gly
            20                  25                  30

Asp Arg Asn Asn Tyr Leu Ala Trp Tyr Val Gln Lys Pro Gly Arg Ser
        35                  40                  45

Pro Gln Leu Leu Ile Asp Leu Ala Ser Asp Arg Ala Ser Gly Val Pro
    50                  55                  60

Asp Arg Phe Ser Gly Ser Gly Ser Glu Lys Asp Phe Thr Leu Ser Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 23
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 23

Asp Ile Val Leu Thr Gln Ser Pro Leu Ser Leu Ser Val Thr Pro Gly
1               5                   10                  15

Glu Ser Ala Ser Ile Ser Cys Lys Ser Asp Gln Ser Leu Gln His Gly
            20                  25                  30

Asp Arg Asn Asn Tyr Leu Ala Trp Tyr Val Gln Lys Pro Gly Arg Ser
        35                  40                  45

Pro Gln Leu Leu Ile Asp Leu Ala Ser Asp Arg Ala Ser Gly Val Pro
    50                  55                  60

Asp Arg Phe Ser Gly Ser Gly Ser Glu Lys Asp Phe Thr Leu Ser Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 24
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 24
```

Asp Ile Val Leu Thr Gln Ser Pro Leu Ser Leu Ser Val Thr Pro Gly
1 5 10 15

Glu Pro Ala Ser Ile Ser Cys Lys Ser Ser Gln Ser Leu Gln His Gly
20 25 30

Asp Arg Asn Asn Tyr Leu Ala Trp Tyr Val Gln Lys Pro Gly Gln Ser
35 40 45

Pro Gln Leu Leu Ile Asp Leu Ala Ser Asp Arg Ala Ser Gly Val Pro
50 55 60

Asp Arg Phe Ser Gly Ser Gly Ser Glu Lys Asp Phe Thr Leu Ser Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

<210> SEQ ID NO 25
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 25

Asp Ile Val Leu Thr Gln Ser Pro Leu Ser Leu Ser Val Thr Pro Gly
1 5 10 15

Glu Ser Ala Ser Ile Ser Cys Lys Ser Ser His Ser Leu Gln His Gly
20 25 30

Asp Arg Asn Asn Tyr Leu Ala Trp Tyr Val Gln Lys Pro Gly Arg Ser
35 40 45

Pro Gln Leu Leu Leu Asp Leu Ala Ser Glu Arg Ala Ser Gly Val Pro
50 55 60

Asp Arg Phe Ser Gly Ser Gly Ser Glu Lys Asp Phe Thr Leu Lys Ile
65 70 75 80

Ser Arg Val Glu Thr Glu Asp Val Gly Thr Tyr Tyr Cys Met Gln Gly
85 90 95

Arg Glu Ser Pro Trp Thr Phe Gly Gln Gly Thr Lys Val Asp Ile Lys
100 105 110

<210> SEQ ID NO 26
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 26

Asp Ile Val Leu Thr Gln Ser Pro Leu Ser Leu Ser Val Thr Pro Gly
1 5 10 15

Glu Pro Ala Ser Ile Ser Cys Lys Ser Ser Gln Ser Leu Ile His Gly
20 25 30

Asp Arg Asn Asn Tyr Leu Ala Trp Tyr Val Gln Lys Pro Gly Lys Ser
35 40 45

Pro Gln Leu Leu Ile Asp Leu Ala Ser Asp Arg Ala Ser Gly Val Pro
50 55 60

Asp Arg Phe Ser Gly Ser Gly Ser Glu Lys Asp Phe Thr Leu Ser Ile
65 70 75 80

Ser Arg Val Glu Ala Glu Asp Val Gly Thr Tyr Tyr Cys Met Gln Gly

```
                85                  90                  95

Arg Glu Ser Pro Trp Thr Phe Gly Gln Gly Thr Lys Val Asp Ile Lys
            100                 105                 110


<210> SEQ ID NO 27
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 27

Asp Ile Val Leu Thr Gln Ser Pro Leu Ser Leu Ser Val Thr Pro Gly
1               5                   10                  15

Glu Pro Ala Ser Ile Ser Cys Lys Ser Ser His Ser Leu Gln His Gly
            20                  25                  30

Asp Arg Asn Asn Tyr Leu Ala Trp Tyr Val Gln Lys Pro Gly Arg Ser
        35                  40                  45

Pro Gln Leu Leu Ile Asp Leu Ala Ser Asp Arg Ala Ser Gly Val Pro
    50                  55                  60

Asp Arg Phe Ser Gly Ser Gly Ser Glu Lys Asp Phe Thr Leu Ser Ile
65                  70                  75                  80

Ser Arg Val Glu Ala Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 28
<211> LENGTH: 112
<212> TYPE: PRT
<213> ORGANISM: Artificial Sequence
<220> FEATURE:
<223> OTHER INFORMATION: Recombinantly produced polypeptide

<400> SEQUENCE: 28

Asp Ile Val Leu Thr Gln Ser Pro Leu Ser Leu Ser Val Thr Pro Gly
1               5                   10                  15

Glu Ser Ala Ser Ile Ser Cys Lys Ser Ser His Ser Leu Gln His Gly
            20                  25                  30

Asp Arg Asn Asn Tyr Leu Ala Trp Tyr Leu Gln Lys Pro Gly Gln Ser
        35                  40                  45

Pro Gln Leu Leu Ile Asp Leu Ala Ser Asp Arg Ala Ser Gly Val Pro
    50                  55                  60

Asp Arg Phe Ser Gly Ser Gly Ser Glu Lys Asp Phe Thr Leu Lys Ile
65                  70                  75                  80

Asp Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 29
<211> LENGTH: 36
<212> TYPE: PRT
<213> ORGANISM: Artificial Sequence
<220> FEATURE:
<223> OTHER INFORMATION: Recombinantly produced polypeptide

<400> SEQUENCE: 29

Cys Ala Lys Gly Ser Lys His Arg Leu Arg Asp Tyr Ala Leu Tyr Asp
1               5                   10                  15
```

Asp Asp Gly Ala Leu Asn Trp Ala Val Asp Val Asp Tyr Leu Ser Asn
20 25 30

Leu Glu Phe Trp
35

<210> SEQ ID NO 30
<211> LENGTH: 11
<212> TYPE: PRT
<213> ORGANISM: Artificial Sequence
<220> FEATURE:
<223> OTHER INFORMATION: Recombinantly produced polypeptide

<400> SEQUENCE: 30

Cys Met Gln Gly Arg Glu Ser Pro Trp Thr Phe
1 5 10

<210> SEQ ID NO 31
<211> LENGTH: 36
<212> TYPE: PRT
<213> ORGANISM: Artificial Sequence
<220> FEATURE:
<223> OTHER INFORMATION: Recombinantly produced polypeptide

<400> SEQUENCE: 31

Cys Ala Lys Gly Ser Lys His Arg Leu Arg Asp Tyr Ala Leu Tyr Asp
1 5 10 15

Glu Asp Gly Ala Leu Glu Trp Ala Val Asp Val Asp Tyr Leu Ala Asn
20 25 30

Leu Glu Phe Trp
35

<210> SEQ ID NO 32
<211> LENGTH: 36
<212> TYPE: PRT
<213> ORGANISM: Artificial Sequence
<220> FEATURE:
<223> OTHER INFORMATION: Recombinantly produced polypeptide

<400> SEQUENCE: 32

Cys Ala Lys Gly Ser Lys His Arg Leu Arg Asp Tyr Ala Leu Tyr Asp
1 5 10 15

Glu Asp Gly Ala Leu Glu Trp Ala Glu Asp Val Asp Tyr Leu Ala Asn
20 25 30

Leu Glu Phe Trp
35

<210> SEQ ID NO 33
<211> LENGTH: 36
<212> TYPE: PRT
<213> ORGANISM: Artificial Sequence
<220> FEATURE:
<223> OTHER INFORMATION: Recombinantly produced polypeptide

<400> SEQUENCE: 33

Cys Ala Lys Gly Ser Lys His Arg Leu Arg Asp Tyr Ala Leu Tyr Asp
1 5 10 15

Asp Asp Gly Ala Leu Glu Trp Ala Glu Asp Val Asp Tyr Leu Ala Asn
20 25 30

Leu Glu Phe Trp
35

<210> SEQ ID NO 34

<211> LENGTH: 36
<212> TYPE: PRT
<213> ORGANISM: Artificial Sequence
<220> FEATURE:
<223> OTHER INFORMATION: Recombinantly produced polypeptide

<400> SEQUENCE: 34

Cys Ala Lys Gly Ser Lys His Arg Leu Arg Asp Tyr Ala Leu Tyr Asp
1               5                   10                  15

Glu Asp Gly Ala Leu Asn Trp Ala Val Asp Val Asp Tyr Leu Ala Asn
            20                  25                  30

Leu Glu Phe Trp
        35

<210> SEQ ID NO 35
<211> LENGTH: 36
<212> TYPE: PRT
<213> ORGANISM: Artificial Sequence
<220> FEATURE:
<223> OTHER INFORMATION: Recombinantly produced polypeptide

<400> SEQUENCE: 35

Cys Ala Lys Gly Ser Lys His Arg Leu Arg Asp Tyr Ala Leu Tyr Asp
1               5                   10                  15

Glu Asp Gly Ala Leu Glu Tyr Ala Glu Asp Val Asp Tyr Leu Ala Asn
            20                  25                  30

Leu Glu Phe Trp
        35

<210> SEQ ID NO 36
<211> LENGTH: 8
<212> TYPE: PRT
<213> ORGANISM: Artificial Sequence
<220> FEATURE:
<223> OTHER INFORMATION: Recombinantly produced polypeptide

<400> SEQUENCE: 36

Gly Asn Thr Leu Lys Thr Tyr Asp
1               5

<210> SEQ ID NO 37
<211> LENGTH: 8
<212> TYPE: PRT
<213> ORGANISM: Artificial Sequence
<220> FEATURE:
<223> OTHER INFORMATION: Recombinantly produced polypeptide

<400> SEQUENCE: 37

Gly Asn Thr Leu Thr Thr Tyr Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Recombinantly produced polypeptide

<400> SEQUENCE: 38

Ile Ser His Glu Gly Asp Lys Lys
1               5

<210> SEQ ID NO 39
<211> LENGTH: 8
<212> TYPE: PRT

<213> ORGANISM: Artificial Sequence
<220> FEATURE:
<223> OTHER INFORMATION: Recombinantly produced polypeptide

<400> SEQUENCE: 39

Ile Ser His Glu Gly Asp Gln Lys
1 5

<210> SEQ ID NO 40
<211> LENGTH: 11
<212> TYPE: PRT
<213> ORGANISM: Artificial Sequence
<220> FEATURE:
<223> OTHER INFORMATION: Recombinantly produced polypeptide

<400> SEQUENCE: 40

His Ser Leu Ile His Gly Asp Arg Asn Asn Tyr
1 5 10

<210> SEQ ID NO 41
<211> LENGTH: 11
<212> TYPE: PRT
<213> ORGANISM: Artificial Sequence
<220> FEATURE:
<223> OTHER INFORMATION: Recombinantly produced polypeptide

<400> SEQUENCE: 41

Gln Ser Leu Gln His Gly Asp Arg Asn Asn Tyr
1 5 10

<210> SEQ ID NO 42
<211> LENGTH: 11
<212> TYPE: PRT
<213> ORGANISM: Artificial Sequence
<220> FEATURE:
<223> OTHER INFORMATION: Recombinantly produced polypeptide

<400> SEQUENCE: 42

Gln Ser Leu Leu His Gly Asp Arg Asn Asn Tyr
1 5 10

<210> SEQ ID NO 43
<211> LENGTH: 11
<212> TYPE: PRT
<213> ORGANISM: Artificial Sequence
<220> FEATURE:
<223> OTHER INFORMATION: Recombinantly produced polypeptide

<400> SEQUENCE: 43

His Ser Leu Gln His Gly Asp Arg Asn Asn Tyr
1 5 10

<210> SEQ ID NO 44
<211> LENGTH: 11
<212> TYPE: PRT
<213> ORGANISM: Artificial Sequence
<220> FEATURE:
<223> OTHER INFORMATION: Recombinantly produced polypeptide

<400> SEQUENCE: 44

Gln Ser Leu Ile His Gly Asp Arg Asn Asn Tyr
1 5 10

<210> SEQ ID NO 45
<211> LENGTH: 3
<212> TYPE: PRT
<213> ORGANISM: Artificial Sequence
<220> FEATURE:
<223> OTHER INFORMATION: Recombinantly produced polypeptide

<400> SEQUENCE: 45

Leu Ala Ser
1

<210> SEQ ID NO 46
<211> LENGTH: 3
<212> TYPE: PRT
<213> ORGANISM: Artificial Sequence
<220> FEATURE:
<223> OTHER INFORMATION: Recombinantly produced polypeptide

<400> SEQUENCE: 46

Leu Gly Ser
1

<210> SEQ ID NO 47
<211> LENGTH: 25
<212> TYPE: PRT
<213> ORGANISM: Artificial Sequence
<220> FEATURE:
<223> OTHER INFORMATION: Recombinantly produced polypeptide

<400> SEQUENCE: 47

```
Gln Val His Leu Thr Gln Ser Gly Pro Glu Val Arg Lys Pro Gly Thr
1               5                   10                  15

Ser Val Lys Val Ser Cys Lys Ala Pro
            20                  25
```

<210> SEQ ID NO 48
<211> LENGTH: 25
<212> TYPE: PRT
<213> ORGANISM: Artificial Sequence
<220> FEATURE:
<223> OTHER INFORMATION: Recombinantly produced polypeptide

<400> SEQUENCE: 48

```
Gln Val Gln Leu Val Gln Ser Gly Ala Glu Val Arg Lys Pro Gly Ala
1               5                   10                  15

Ser Val Lys Val Ser Cys Lys Asn Pro
            20                  25
```

<210> SEQ ID NO 49
<211> LENGTH: 25
<212> TYPE: PRT
<213> ORGANISM: Artificial Sequence
<220> FEATURE:
<223> OTHER INFORMATION: Recombinantly produced polypeptide

<400> SEQUENCE: 49

```
Gln Ala Gln Leu Val Gln Ser Gly Ala Glu Val Arg Lys Pro Gly Ala
1               5                   10                  15

Ser Val Lys Val Ser Cys Lys Asn Pro
            20                  25
```

<210> SEQ ID NO 50
<211> LENGTH: 25
<212> TYPE: PRT
<213> ORGANISM: Artificial Sequence
<220> FEATURE:
<223> OTHER INFORMATION: Recombinantly produced polypeptide

<400> SEQUENCE: 50

Gln Val Gln Leu Val Gln Ser Gly Pro Glu Val Arg Lys Pro Gly Ala
1 5 10 15

Ser Val Lys Val Ser Cys Lys Asn Pro
20 25

<210> SEQ ID NO 51
<211> LENGTH: 25
<212> TYPE: PRT
<213> ORGANISM: Artificial Sequence
<220> FEATURE:
<223> OTHER INFORMATION: Recombinantly produced polypeptide

<400> SEQUENCE: 51

Gln Val Gln Leu Val Gln Ser Gly Pro Glu Val Arg Lys Pro Gly Thr
1 5 10 15

Ser Val Lys Val Ser Cys Lys Asn Pro
20 25

<210> SEQ ID NO 52
<211> LENGTH: 25
<212> TYPE: PRT
<213> ORGANISM: Artificial Sequence
<220> FEATURE:
<223> OTHER INFORMATION: Recombinantly produced polypeptide

<400> SEQUENCE: 52

Gln Ala Gln Leu Val Gln Ser Gly Ala Glu Val Arg Lys Pro Gly Thr
1 5 10 15

Ser Val Lys Val Ser Cys Lys Asn Pro
20 25

<210> SEQ ID NO 53
<211> LENGTH: 25
<212> TYPE: PRT
<213> ORGANISM: Artificial Sequence
<220> FEATURE:
<223> OTHER INFORMATION: Recombinantly produced polypeptide

<400> SEQUENCE: 53

Gln Ala Gln Leu Val Gln Ser Gly Pro Glu Val Arg Lys Pro Gly Thr
1 5 10 15

Ser Val Lys Val Ser Cys Lys Asn Pro
20 25

<210> SEQ ID NO 54
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 54

Leu His Trp Val Arg Ser Val Pro Gly Gln Gly Leu Gln Trp Met Gly
1 5 10 15

Trp

<210> SEQ ID NO 55
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 55

Leu His Trp Val Arg Gln Val Pro Gly Gln Gly Leu Gln Trp Met Gly
1 5 10 15

Trp

<210> SEQ ID NO 56
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 56

Leu His Trp Val Arg Ser Val Pro Gly Gln Gly Leu Glu Trp Met Gly
1 5 10 15

Trp

<210> SEQ ID NO 57
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 57

Leu His Trp Val Arg Gln Val Pro Gly Gln Gly Leu Glu Trp Met Gly
1 5 10 15

Trp

<210> SEQ ID NO 58
<211> LENGTH: 37
<212> TYPE: PRT
<213> ORGANISM: Artificial Sequence
<220> FEATURE:
<223> OTHER INFORMATION: Recombinantly produced polypeptide

<400> SEQUENCE: 58

Val Ile Val Glu Arg Phe Lys Ala Lys Val Thr Ile Asp Trp Asp Arg
1 5 10 15

Ser Thr Asn Thr Ala Tyr Leu Gln Leu Ser Gly Leu Thr Ser Gly Asp
20 25 30

Thr Ala Val Tyr Tyr
35

<210> SEQ ID NO 59
<211> LENGTH: 37
<212> TYPE: PRT
<213> ORGANISM: Artificial Sequence
<220> FEATURE:
<223> OTHER INFORMATION: Recombinantly produced polypeptide

<400> SEQUENCE: 59

Val Ile Val Glu Arg Phe Lys Ala Lys Val Asp Ile Asp Trp Asp Arg
1 5 10 15

Ser Thr Asn Thr Ala Tyr Leu Gln Leu Ser Gly Leu Thr Ser Glu Asp
20 25 30

Thr Ala Val Tyr Tyr
35

<210> SEQ ID NO 60
<211> LENGTH: 37
<212> TYPE: PRT
<213> ORGANISM: Artificial Sequence
<220> FEATURE:

<223> OTHER INFORMATION: Recombinantly produced polypeptide

<400> SEQUENCE: 60

Val Ile Ala Glu Arg Phe Lys Ala Lys Val Asp Ile Asp Trp Asp Arg
1               5                   10                  15

Ser Thr Asn Thr Ala Tyr Leu Gly Leu Ser Gly Leu Thr Ser Glu Asp
            20                  25                  30

Thr Ala Val Tyr Tyr
        35

<210> SEQ ID NO 61
<211> LENGTH: 37
<212> TYPE: PRT
<213> ORGANISM: Artificial Sequence
<220> FEATURE:
<223> OTHER INFORMATION: Recombinantly produced polypeptide

<400> SEQUENCE: 61

Val Ile Val Glu Lys Phe Lys Ala Lys Val Asp Ile Asp Trp Asp Arg
1               5                   10                  15

Ser Thr Asn Thr Ala Tyr Leu Gln Leu Ser Gly Leu Thr Ser Glu Asp
            20                  25                  30

Thr Ala Val Tyr Tyr
        35

<210> SEQ ID NO 62
<211> LENGTH: 37
<212> TYPE: PRT
<213> ORGANISM: Artificial Sequence
<220> FEATURE:
<223> OTHER INFORMATION: Recombinantly produced polypeptide

<400> SEQUENCE: 62

Val Ile Val Glu Arg Phe Lys Ala Lys Val Asp Ile Asp Trp Asp Arg
1               5                   10                  15

Ser Thr Asn Thr Ala Tyr Leu Gly Leu Ser Gly Leu Thr Ser Glu Asp
            20                  25                  30

Thr Ala Val Tyr Tyr
        35

<210> SEQ ID NO 63
<211> LENGTH: 37
<212> TYPE: PRT
<213> ORGANISM: Artificial Sequence
<220> FEATURE:
<223> OTHER INFORMATION: Recombinantly produced polypeptide

<400> SEQUENCE: 63

Glu Ile Val Glu Arg Phe Lys Ala Lys Val Asp Ile Asp Trp Asp Arg
1               5                   10                  15

Ser Thr Asn Thr Ala Tyr Leu Gln Leu Ser Gly Leu Thr Ser Glu Asp
            20                  25                  30

Thr Ala Val Tyr Tyr
        35

<210> SEQ ID NO 64
<211> LENGTH: 37
<212> TYPE: PRT
<213> ORGANISM: Artificial Sequence
<220> FEATURE:
<223> OTHER INFORMATION: Recombinantly produced polypeptide

<400> SEQUENCE: 64

Val Ile Val Glu Arg Phe Lys Ala Lys Val Thr Ile Asp Trp Asp Arg
1 5 10 15

Ser Thr Asn Thr Ala Tyr Leu Gln Leu Ser Gly Leu Thr Ser Glu Asp
20 25 30

Thr Ala Val Tyr Tyr
35

<210> SEQ ID NO 65
<211> LENGTH: 37
<212> TYPE: PRT
<213> ORGANISM: Artificial Sequence
<220> FEATURE:
<223> OTHER INFORMATION: Recombinantly produced polypeptide

<400> SEQUENCE: 65

Val Ile Val Glu Arg Phe Gln Gly Arg Val Asp Ile Asp Trp Asp Arg
1 5 10 15

Ser Thr Asn Thr Ala Tyr Leu Gln Leu Ser Gly Leu Thr Ser Glu Asp
20 25 30

Thr Ala Val Tyr Tyr
35

<210> SEQ ID NO 66
<211> LENGTH: 10
<212> TYPE: PRT
<213> ORGANISM: Artificial Sequence
<220> FEATURE:
<223> OTHER INFORMATION: Recombinantly produced polypeptide

<400> SEQUENCE: 66

Gly Gln Gly Thr Ala Val Thr Val Ser Ser
1 5 10

<210> SEQ ID NO 67
<211> LENGTH: 26
<212> TYPE: PRT
<213> ORGANISM: Artificial Sequence
<220> FEATURE:
<223> OTHER INFORMATION: Recombinantly produced polypeptide

<400> SEQUENCE: 67

Asp Phe Val Leu Thr Gln Ser Pro His Ser Leu Ser Val Thr Pro Gly
1 5 10 15

Glu Ser Ala Ser Ile Ser Cys Lys Ser Ser
20 25

<210> SEQ ID NO 68
<211> LENGTH: 26
<212> TYPE: PRT
<213> ORGANISM: Artificial Sequence
<220> FEATURE:
<223> OTHER INFORMATION: Recombinantly produced polypeptide

<400> SEQUENCE: 68

Asp Ile Val Leu Thr Gln Ser Pro Leu Ser Leu Ser Val Thr Pro Gly
1 5 10 15

Glu Ser Ala Ser Ile Ser Cys Lys Ser Asp
20 25

<210> SEQ ID NO 69
<211> LENGTH: 26
<212> TYPE: PRT
<213> ORGANISM: Artificial Sequence
<220> FEATURE:
<223> OTHER INFORMATION: Recombinantly produced polypeptide

<400> SEQUENCE: 69

Asp Ile Val Leu Thr Gln Ser Pro Leu Ser Leu Ser Val Thr Pro Gly
1               5                   10                  15

Glu Ser Ala Ser Ile Ser Cys Lys Ser Ser
            20                  25

<210> SEQ ID NO 70
<211> LENGTH: 26
<212> TYPE: PRT
<213> ORGANISM: Artificial Sequence
<220> FEATURE:
<223> OTHER INFORMATION: Recombinantly produced polypeptide

<400> SEQUENCE: 70

Asp Ile Val Leu Thr Gln Ser Pro His Ser Leu Ser Val Thr Pro Gly
1               5                   10                  15

Glu Pro Ala Ser Ile Ser Cys Lys Ser Ser
            20                  25

<210> SEQ ID NO 71
<211> LENGTH: 26
<212> TYPE: PRT
<213> ORGANISM: Artificial Sequence
<220> FEATURE:
<223> OTHER INFORMATION: Recombinantly produced polypeptide

<400> SEQUENCE: 71

Asp Phe Val Leu Thr Gln Ser Pro Leu Ser Leu Ser Val Thr Pro Gly
1               5                   10                  15

Glu Ser Ala Ser Ile Ser Cys Lys Ser Ser
            20                  25

<210> SEQ ID NO 72
<211> LENGTH: 26
<212> TYPE: PRT
<213> ORGANISM: Artificial Sequence
<220> FEATURE:
<223> OTHER INFORMATION: Recombinantly produced polypeptide

<400> SEQUENCE: 72

Asp Phe Val Leu Thr Gln Ser Pro Leu Ser Leu Ser Val Thr Pro Gly
1               5                   10                  15

Glu Ser Ala Ser Ile Ser Cys Lys Ser Asp
            20                  25

<210> SEQ ID NO 73
<211> LENGTH: 26
<212> TYPE: PRT
<213> ORGANISM: Artificial Sequence
<220> FEATURE:
<223> OTHER INFORMATION: Recombinantly produced polypeptide

<400> SEQUENCE: 73

Asp Ile Val Leu Thr Gln Ser Pro Leu Ser Leu Ser Val Thr Pro Gly
1               5                   10                  15

Glu Pro Ala Ser Ile Ser Cys Lys Ser Asp
            20                  25

<210> SEQ ID NO 74
<211> LENGTH: 26
<212> TYPE: PRT

<213> ORGANISM: Artificial Sequence
<220> FEATURE:
<223> OTHER INFORMATION: Recombinantly produced polypeptide

<400> SEQUENCE: 74

Asp Ile Val Leu Thr Gln Ser Pro Leu Ser Leu Ser Val Thr Pro Gly
1 5 10 15

Glu Pro Ala Ser Ile Ser Cys Lys Ser Ser
20 25

<210> SEQ ID NO 75
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 75

Leu Ala Trp Tyr Val Gln Lys Pro Gly Arg Ser Pro Gln Leu Leu Ile
1 5 10 15

Tyr

<210> SEQ ID NO 76
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 76

Leu Ala Trp Tyr Val Gln Lys Pro Gly Lys Ser Pro Gln Leu Leu Ile
1 5 10 15

Asp

<210> SEQ ID NO 77
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 77

Leu Ala Trp Tyr Leu Gln Lys Pro Gly Lys Ser Pro Gln Leu Leu Leu
1 5 10 15

Asp

<210> SEQ ID NO 78
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 78

Leu Ala Trp Tyr Val Gln Lys Pro Gly Arg Ser Pro Gln Leu Leu Leu
1 5 10 15

Asp

<210> SEQ ID NO 79
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 79

Leu Ala Trp Tyr Val Gln Lys Pro Gly Gln Ser Pro Gln Leu Leu Ile
1 5 10 15

Asp

<210> SEQ ID NO 80
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 80

Leu Ala Trp Tyr Val Gln Lys Pro Gly Arg Ser Pro Gln Leu Leu Ile
1 5 10 15

Asp

<210> SEQ ID NO 81
<211> LENGTH: 17
<212> TYPE: PRT
<213> ORGANISM: Artificial Sequence
<220> FEATURE:
<223> OTHER INFORMATION: Recombinantly produced polypeptide

<400> SEQUENCE: 81

Leu Ala Trp Tyr Leu Gln Lys Pro Gly Gln Ser Pro Gln Leu Leu Ile
1 5 10 15

Asp

<210> SEQ ID NO 82
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 82

Ser Arg Ala Ser Gly Val Pro Asp Arg Phe Ser Gly Ser Gly Ser Asp
1 5 10 15

Lys Asp Phe Thr Leu Lys Ile Ser Arg Val Glu Thr Glu Asp Val Gly
20 25 30

Thr Tyr Tyr
35

<210> SEQ ID NO 83
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 83

Glu Arg Ala Ser Gly Val Pro Asp Arg Phe Ser Gly Ser Gly Ser Glu
1 5 10 15

Lys Asp Phe Thr Leu Lys Ile Ser Arg Val Glu Ala Glu Asp Val Gly
20 25 30

Thr Tyr Tyr
35

<210> SEQ ID NO 84
<211> LENGTH: 35

<212> TYPE: PRT
<213> ORGANISM: Artificial Sequence
<220> FEATURE:
<223> OTHER INFORMATION: Recombinantly produced polypeptide

<400> SEQUENCE: 84

```
Asp Arg Ala Ser Gly Val Pro Asp Arg Phe Ser Gly Ser Gly Ser Arg
1               5                   10                  15

Lys Asp Phe Thr Leu Ser Ile Ser Arg Val Glu Ala Glu Asp Val Gly
            20                  25                  30

Thr Tyr Tyr
        35
```

<210> SEQ ID NO 85
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 85

```
Asp Arg Ala Ser Gly Val Pro Asp Arg Phe Ser Gly Ser Gly Ser Glu
1               5                   10                  15

Lys Asp Phe Thr Leu Lys Ile Asp Arg Val Glu Thr Glu Asp Val Gly
            20                  25                  30

Thr Tyr Tyr
        35
```

<210> SEQ ID NO 86
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 86

```
Asp Arg Ala Ser Gly Val Pro Asp Arg Phe Ser Gly Ser Gly Ser Glu
1               5                   10                  15

Lys Asp Phe Thr Leu Ser Ile Asp Arg Val Glu Ala Glu Asp Val Gly
            20                  25                  30

Thr Tyr Tyr
        35
```

<210> SEQ ID NO 87
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 87

```
Glu Arg Ala Ser Gly Val Pro Asp Arg Phe Ser Gly Ser Gly Ser Arg
1               5                   10                  15

Lys Asp Phe Thr Leu Lys Ile Asp Arg Val Glu Ala Glu Asp Val Gly
            20                  25                  30

Thr Tyr Tyr
        35
```

<210> SEQ ID NO 88
<211> LENGTH: 35
<212> TYPE: PRT
<213> ORGANISM: Artificial Sequence
<220> FEATURE:

<223> OTHER INFORMATION: Recombinantly produced polypeptide

<400> SEQUENCE: 88

Asp Arg Ala Ser Gly Val Pro Asp Arg Phe Ser Gly Ser Gly Ser Glu
1 5 10 15

Lys Asp Phe Thr Leu Ser Ile Ser Arg Val Glu Thr Glu Asp Val Gly
20 25 30

Thr Tyr Tyr
35

<210> SEQ ID NO 89
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 89

Asp Arg Ala Ser Gly Val Pro Asp Arg Phe Ser Gly Ser Gly Ser Glu
1 5 10 15

Lys Asp Phe Thr Leu Lys Ile Asp Arg Val Glu Ala Glu Asp Val Gly
20 25 30

Thr Tyr Tyr
35

<210> SEQ ID NO 90
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 90

Glu Arg Ala Ser Gly Val Pro Asp Arg Phe Ser Gly Ser Gly Ser Arg
1 5 10 15

Lys Asp Phe Thr Leu Lys Ile Ser Arg Val Glu Thr Glu Asp Val Gly
20 25 30

Thr Tyr Tyr
35

<210> SEQ ID NO 91
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 91

Asp Arg Ala Ser Gly Val Pro Asp Arg Phe Ser Gly Ser Gly Ser Glu
1 5 10 15

Lys Asp Phe Thr Leu Ser Ile Ser Arg Val Glu Ala Glu Asp Val Gly
20 25 30

Thr Tyr Tyr
35

<210> SEQ ID NO 92
<211> LENGTH: 35
<212> TYPE: PRT
<213> ORGANISM: Artificial Sequence
<220> FEATURE:
<223> OTHER INFORMATION: Recombinantly produced polypeptide

<400> SEQUENCE: 92

```
Glu Arg Ala Ser Gly Val Pro Asp Arg Phe Ser Gly Ser Gly Ser Glu
1               5                   10                  15

Lys Asp Phe Thr Leu Lys Ile Ser Arg Val Glu Thr Glu Asp Val Gly
            20                  25                  30

Thr Tyr Tyr
        35
```

<210> SEQ ID NO 93
<211> LENGTH: 9
<212> TYPE: PRT
<213> ORGANISM: Artificial Sequence
<220> FEATURE:
<223> OTHER INFORMATION: Recombinantly produced polypeptide

<400> SEQUENCE: 93

```
Gly Gln Gly Thr Lys Val Asp Ile Lys
1               5
```

<210> SEQ ID NO 94
<211> LENGTH: 8
<212> TYPE: PRT
<213> ORGANISM: Artificial Sequence
<220> FEATURE:
<223> OTHER INFORMATION: Recombinantly produced polypeptide

<400> SEQUENCE: 94

```
Gly Asn Thr Leu Thr Thr Tyr Asp
1               5
```

<210> SEQ ID NO 95
<211> LENGTH: 8
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (7)..(7)
<223> OTHER INFORMATION: Xaa is Gln or Lys

<400> SEQUENCE: 95

```
Ile Ser His Glu Gly Asp Xaa Lys
1               5
```

<210> SEQ ID NO 96
<211> LENGTH: 36
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (17)..(17)
<223> OTHER INFORMATION: Xaa is Glu or Asp
<220> FEATURE:
<221> NAME/KEY: MISC_FEATURE
<222> LOCATION: (22)..(22)
<223> OTHER INFORMATION: Xaa is Glu or Asn
<220> FEATURE:
<221> NAME/KEY: MISC_FEATURE
<222> LOCATION: (23)..(23)
<223> OTHER INFORMATION: Xaa is Try or Tyr
<220> FEATURE:
<221> NAME/KEY: MISC_FEATURE
<222> LOCATION: (25)..(25)
<223> OTHER INFORMATION: Xaa is Glu or Val

<400> SEQUENCE: 96

```
Cys Ala Lys Gly Ser Lys His Arg Leu Arg Asp Tyr Ala Leu Tyr Asp
1               5                   10                  15

Xaa Asp Gly Ala Leu Xaa Xaa Ala Xaa Asp Val Asp Tyr Leu Ala Asn
            20                  25                  30

Leu Glu Phe Trp
        35


<210> SEQ ID NO 97
<211> LENGTH: 11
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (1)..(1)
<223> OTHER INFORMATION: Xaa is His or Gln
<220> FEATURE:
<221> NAME/KEY: MISC_FEATURE
<222> LOCATION: (4)..(4)
<223> OTHER INFORMATION: Xaa is Ile, Gln or Leu

<400> SEQUENCE: 97

Xaa Ser Leu Xaa His Gly Asp Arg Asn Asn Tyr
1               5                   10


<210> SEQ ID NO 98
<211> LENGTH: 3
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (2)..(2)
<223> OTHER INFORMATION: Xaa is Ala or Gly

<400> SEQUENCE: 98

Leu Xaa Ser
1


<210> SEQ ID NO 99
<211> LENGTH: 11
<212> TYPE: PRT
<213> ORGANISM: Artificial Sequence
<220> FEATURE:
<223> OTHER INFORMATION: Recombinantly produced polypeptide

<400> SEQUENCE: 99

Cys Met Gln Gly Arg Glu Ser Pro Trp Thr Phe
1               5                   10


<210> SEQ ID NO 100
<211> LENGTH: 25
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (2)..(2)
<223> OTHER INFORMATION: Xaa is Val or Ala
<220> FEATURE:
<221> NAME/KEY: MISC_FEATURE
<222> LOCATION: (9)..(9)
<223> OTHER INFORMATION: Xaa is Pro or Ala
<220> FEATURE:
<221> NAME/KEY: MISC_FEATURE
<222> LOCATION: (16)..(16)
<223> OTHER INFORMATION: Xaa is Thr or Ala
```

<400> SEQUENCE: 100

Gln Xaa Gln Leu Val Gln Ser Gly Xaa Glu Val Arg Lys Pro Gly Xaa
1               5                   10                  15

Ser Val Lys Val Ser Cys Lys Asn Pro
            20                  25

<210> SEQ ID NO 101
<211> LENGTH: 17
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (6)..(6)
<223> OTHER INFORMATION: Xaa is Ser or Gln
<220> FEATURE:
<221> NAME/KEY: MISC_FEATURE
<222> LOCATION: (13)..(13)
<223> OTHER INFORMATION: Xaa is Gln or Glu

<400> SEQUENCE: 101

Leu His Trp Val Arg Xaa Val Pro Gly Gln Gly Leu Xaa Trp Met Gly
1               5                   10                  15

Trp

<210> SEQ ID NO 102
<211> LENGTH: 37
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (3)..(3)
<223> OTHER INFORMATION: Xaa is Val or Ala
<220> FEATURE:
<221> NAME/KEY: MISC_FEATURE
<222> LOCATION: (5)..(5)
<223> OTHER INFORMATION: Xaa is Arg or Lys
<220> FEATURE:
<221> NAME/KEY: MISC_FEATURE
<222> LOCATION: (7)..(7)
<223> OTHER INFORMATION: Xaa is Lys or Gln
<220> FEATURE:
<221> NAME/KEY: MISC_FEATURE
<222> LOCATION: (8)..(8)
<223> OTHER INFORMATION: Xaa is Ala or Gly
<220> FEATURE:
<221> NAME/KEY: MISC_FEATURE
<222> LOCATION: (9)..(9)
<223> OTHER INFORMATION: Xaa is Lys or Arg
<220> FEATURE:
<221> NAME/KEY: MISC_FEATURE
<222> LOCATION: (11)..(11)
<223> OTHER INFORMATION: Xaa is Thr or Asp
<220> FEATURE:
<221> NAME/KEY: MISC_FEATURE
<222> LOCATION: (24)..(24)
<223> OTHER INFORMATION: Xaa is Gln or Gly

<400> SEQUENCE: 102

Val Ile Xaa Glu Xaa Phe Xaa Xaa Xaa Val Xaa Ile Asp Trp Asp Arg
1               5                   10                  15

Ser Thr Asn Thr Ala Tyr Leu Xaa Leu Ser Gly Leu Thr Ser Glu Asp
            20                  25                  30

Thr Ala Val Tyr Tyr
        35

<210> SEQ ID NO 103
<211> LENGTH: 10
<212> TYPE: PRT
<213> ORGANISM: Artificial Sequence
<220> FEATURE:
<223> OTHER INFORMATION: Recombinantly produced polypeptide

<400> SEQUENCE: 103

```
Gly Gln Gly Thr Ala Val Thr Val Ser Ser
1               5                   10
```

<210> SEQ ID NO 104
<211> LENGTH: 26
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (2)..(2)
<223> OTHER INFORMATION: Xaa is Phe or Ile
<220> FEATURE:
<221> NAME/KEY: MISC_FEATURE
<222> LOCATION: (9)..(9)
<223> OTHER INFORMATION: Xaa is His or Leu
<220> FEATURE:
<221> NAME/KEY: MISC_FEATURE
<222> LOCATION: (18)..(18)
<223> OTHER INFORMATION: Xaa is Ser or Pro
<220> FEATURE:
<221> NAME/KEY: MISC_FEATURE
<222> LOCATION: (26)..(26)
<223> OTHER INFORMATION: Xaa is Ser or Asp

<400> SEQUENCE: 104

```
Asp Xaa Val Leu Thr Gln Ser Pro Xaa Ser Leu Ser Val Thr Pro Gly
1               5                   10                  15

Glu Xaa Ala Ser Ile Ser Cys Lys Ser Xaa
            20                  25
```

<210> SEQ ID NO 105
<211> LENGTH: 17
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 105

```
Leu Ala Trp Tyr Xaa Gln Lys Pro Gly Xaa Ser Pro Gln Leu Leu Xaa
1               5                   10                  15

Asp
```

<210> SEQ ID NO 106
<211> LENGTH: 35
<212> TYPE: PRT
<213> ORGANISM: Artificial Sequence
<220> FEATURE:
<223> OTHER INFORMATION: Recombinantly produced polypeptide
<220> FEATURE:
<221> NAME/KEY: MISC_FEATURE
<222> LOCATION: (1)..(1)
<223> OTHER INFORMATION: Xaa is Glu or Asp
<220> FEATURE:
<221> NAME/KEY: MISC_FEATURE
<222> LOCATION: (16)..(16)
<223> OTHER INFORMATION: Xaa is Glu or Arg
<220> FEATURE:
<221> NAME/KEY: MISC_FEATURE
<222> LOCATION: (22)..(22)
<223> OTHER INFORMATION: Xaa is Lys or Ser
<220> FEATURE:
<221> NAME/KEY: MISC_FEATURE
<222> LOCATION: (24)..(24)
<223> OTHER INFORMATION: Xaa is Ser or Asp
<220> FEATURE:
<221> NAME/KEY: MISC_FEATURE
<222> LOCATION: (28)..(28)
<223> OTHER INFORMATION: Xaa is Thr or Ala

<400> SEQUENCE: 106

```
Xaa Arg Ala Ser Gly Val Pro Asp Arg Phe Ser Gly Ser Gly Ser Xaa
1               5                   10                  15

Lys Asp Phe Thr Leu Xaa Ile Xaa Arg Val Glu Xaa Glu Asp Val Gly
            20                  25                  30

Thr Tyr Tyr
        35
```

<210> SEQ ID NO 107
<211> LENGTH: 9
<212> TYPE: PRT
<213> ORGANISM: Artificial Sequence
<220> FEATURE:
<223> OTHER INFORMATION: Recombinantly produced polypeptide

<400> SEQUENCE: 107

```
Gly Gln Gly Thr Lys Val Asp Ile Lys
1               5
```

<210> SEQ ID NO 108
<211> LENGTH: 330
<212> TYPE: PRT
<213> ORGANISM: Artificial Sequence
<220> FEATURE:
<223> OTHER INFORMATION: Recombinantly produced polypeptide

<400> SEQUENCE: 108

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 109
<211> LENGTH: 108
<212> TYPE: PRT
<213> ORGANISM: Artificial Sequence
<220> FEATURE:
<223> OTHER INFORMATION: Recombinantly produced polypeptide

<400> SEQUENCE: 109

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Gly
            100                 105
```

<210> SEQ ID NO 110
<211> LENGTH: 330
<212> TYPE: PRT
<213> ORGANISM: Artificial Sequence
<220> FEATURE:
<223> OTHER INFORMATION: Recombinantly produced polypeptide

<400> SEQUENCE: 110

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Leu His Glu Ala Leu His Ser His Tyr Thr
305 310 315 320

Gln Lys Ser Leu Ser Leu Ser Pro Gly Lys
325 330

<210> SEQ ID NO 111
<211> LENGTH: 860
<212> TYPE: PRT
<213> ORGANISM: Artificial Sequence
<220> FEATURE:
<223> OTHER INFORMATION: Recombinantly produced polypeptide

<400> SEQUENCE: 111

Met Arg Val Met Gly Ile Gln Arg Asn Cys Gln His Leu Phe Arg Trp
1 5 10 15

Gly Thr Met Ile Leu Gly Met Ile Ile Ile Cys Ser Ala Ala Glu Asn
20 25 30

```
Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Glu Val Met Ile Arg
            260                 265                 270

Ser Glu Asn Ile Thr Asn Asn Ala Lys Asn Ile Leu Val Gln Phe Asn
        275                 280                 285

Thr Pro Val Gln Ile Asn Cys Thr Arg Pro Asn Asn Asn Thr Arg Lys
    290                 295                 300

Ser Ile Arg Ile Gly Pro Gly Gln Ala Phe Tyr Ala Thr Gly Asp Ile
305                 310                 315                 320

Ile Gly Asp Ile Arg Gln Ala His Cys Thr Val Ser Lys Ala Thr Trp
                325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
        355                 360                 365

Val Thr Thr His Ser Phe Asn Cys Gly Gly Glu Phe Phe Tyr Cys Asn
    370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
                405                 410                 415

Ile Lys Gln Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly
        435                 440                 445
```

```
Leu Ile Leu Thr Arg Asp Gly Gly Ser Thr Asn Ser Thr Thr Glu Thr
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Arg Ala Lys Arg Arg Val Val Gly Arg Glu Lys Arg Ala Val Gly Ile
            500                 505                 510

Gly Ala Val Phe Leu Gly Phe Leu Gly Ala Ala Gly Ser Thr Met Gly
        515                 520                 525

Ala Ala Ser Met Thr Leu Thr Val Gln Ala Arg Asn Leu Leu Ser Gly
    530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Asn Val Pro Trp Asn
        595                 600                 605

Ser Ser Trp Ser Asn Arg Asn Leu Ser Glu Ile Trp Asp Asn Met Thr
    610                 615                 620

Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Glu Lys Asn Glu Gln Asp
                645                 650                 655

Leu Leu Ala Leu Asp Lys Trp Ala Ser Leu Trp Asn Trp Phe Asp Ile
            660                 665                 670

Ser Asn Trp Leu Trp Tyr Ile Lys Ile Phe Ile Met Ile Val Gly Gly
        675                 680                 685

Leu Ile Gly Leu Arg Ile Val Phe Ala Val Leu Ser Val Ile His Arg
    690                 695                 700

Val Arg Gln Gly Tyr Ser Pro Leu Ser Phe Gln Thr His Thr Pro Asn
705                 710                 715                 720

Pro Arg Gly Leu Asp Arg Pro Glu Arg Ile Glu Glu Glu Asp Gly Glu
                725                 730                 735

Gln Asp Arg Gly Arg Ser Thr Arg Leu Val Ser Gly Phe Leu Ala Leu
            740                 745                 750

Ala Trp Asp Asp Leu Arg Ser Leu Cys Leu Phe Cys Tyr His Arg Leu
        755                 760                 765

Arg Asp Phe Ile Leu Ile Ala Ala Arg Ile Val Glu Leu Leu Gly His
    770                 775                 780

Ser Ser Leu Lys Gly Leu Arg Leu Gly Trp Glu Gly Leu Lys Tyr Leu
785                 790                 795                 800

Trp Asn Leu Leu Ala Tyr Trp Gly Arg Glu Leu Lys Ile Ser Ala Ile
                805                 810                 815

Asn Leu Phe Asp Thr Ile Ala Ile Ala Val Ala Glu Trp Thr Asp Arg
            820                 825                 830

Val Ile Glu Ile Gly Gln Arg Leu Cys Arg Ala Phe Leu His Ile Pro
        835                 840                 845

Arg Arg Ile Arg Gln Gly Leu Glu Arg Ala Leu Leu
    850                 855                 860
```

<210> SEQ ID NO 112
<211> LENGTH: 860
<212> TYPE: PRT
<213> ORGANISM: Artificial Sequence
<220> FEATURE:
<223> OTHER INFORMATION: Recombinantly produced polypeptide

<400> SEQUENCE: 112

```
Met Arg Val Met Gly Ile Gln Arg Asn Cys Gln His Leu Phe Arg Trp
1               5                   10                  15

Gly Thr Met Ile Leu Gly Met Ile Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Glu Val Met Ile Arg
            260                 265                 270

Ser Glu Asn Ile Thr Asn Asn Ala Lys Asn Ile Leu Val Gln Phe Asn
        275                 280                 285

Thr Pro Val Gln Ile Asn Cys Thr Arg Pro Asn Asn Asn Thr Arg Lys
    290                 295                 300

Ser Ile Arg Ile Gly Pro Gly Gln Ala Phe Tyr Ala Thr Gly Asp Ile
305                 310                 315                 320

Ile Gly Asp Ile Arg Gln Ala His Cys Asn Val Ser Lys Ala Thr Trp
                325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
        355                 360                 365

Val Thr Thr His Ser Phe Asn Cys Gly Gly Glu Phe Phe Tyr Cys Asn
```

```
    370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
                405                 410                 415

Ile Lys Gln Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly
        435                 440                 445

Leu Ile Leu Thr Arg Asp Gly Gly Ser Thr Asn Ser Thr Thr Glu Thr
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Arg Ala Lys Arg Arg Val Val Gly Arg Glu Lys Arg Ala Val Gly Ile
            500                 505                 510

Gly Ala Val Phe Leu Gly Phe Leu Gly Ala Ala Gly Ser Thr Met Gly
        515                 520                 525

Ala Ala Ser Met Thr Leu Thr Val Gln Ala Arg Asn Leu Leu Ser Gly
    530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Asn Val Pro Trp Asn
        595                 600                 605

Ser Ser Trp Ser Asn Arg Asn Leu Ser Glu Ile Trp Asp Asn Met Thr
    610                 615                 620

Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Glu Lys Asn Glu Gln Asp
                645                 650                 655

Leu Leu Ala Leu Asp Lys Trp Ala Ser Leu Trp Asn Trp Phe Asp Ile
            660                 665                 670

Ser Asn Trp Leu Trp Tyr Ile Lys Ile Phe Ile Met Ile Val Gly Gly
        675                 680                 685

Leu Ile Gly Leu Arg Ile Val Phe Ala Val Leu Ser Val Ile His Arg
    690                 695                 700

Val Arg Gln Gly Tyr Ser Pro Leu Ser Phe Gln Thr His Thr Pro Asn
705                 710                 715                 720

Pro Arg Gly Leu Asp Arg Pro Glu Arg Ile Glu Glu Glu Asp Gly Glu
                725                 730                 735

Gln Asp Arg Gly Arg Ser Thr Arg Leu Val Ser Gly Phe Leu Ala Leu
            740                 745                 750

Ala Trp Asp Asp Leu Arg Ser Leu Cys Leu Phe Cys Tyr His Arg Leu
        755                 760                 765

Arg Asp Phe Ile Leu Ile Ala Ala Arg Ile Val Glu Leu Leu Gly His
    770                 775                 780

Ser Ser Leu Lys Gly Leu Arg Leu Gly Trp Glu Gly Leu Lys Tyr Leu
785                 790                 795                 800
```

Trp Asn Leu Leu Ala Tyr Trp Gly Arg Glu Leu Lys Ile Ser Ala Ile
805 810 815

Asn Leu Phe Asp Thr Ile Ala Ile Ala Val Ala Glu Trp Thr Asp Arg
820 825 830

Val Ile Glu Ile Gly Gln Arg Leu Cys Arg Ala Phe Leu His Ile Pro
835 840 845

Arg Arg Ile Arg Gln Gly Leu Glu Arg Ala Leu Leu
850 855 860

<210> SEQ ID NO 113
<211> LENGTH: 634
<212> TYPE: PRT
<213> ORGANISM: Artificial Sequence
<220> FEATURE:
<223> OTHER INFORMATION: Recombinantly produced polypeptide

<400> SEQUENCE: 113

Ala Glu Asn Leu Trp Val Thr Val Tyr Tyr Gly Val Pro Val Trp Lys
1 5 10 15

Asp Ala Glu Thr Thr Leu Phe Cys Ala Ser Asp Ala Lys Ala Tyr Glu
20 25 30

Thr Glu Lys His Asn Val Trp Ala Thr His Ala Cys Val Pro Thr Asp
35 40 45

Pro Asn Pro Gln Glu Ile His Leu Glu Asn Val Thr Glu Glu Phe Asn
50 55 60

Met Trp Lys Asn Asn Met Val Glu Gln Met His Thr Asp Ile Ile Ser
65 70 75 80

Leu Trp Asp Gln Ser Leu Lys Pro Cys Val Lys Leu Thr Pro Leu Cys
85 90 95

Val Thr Leu Gln Cys Thr Asn Val Thr Asn Asn Ile Thr Asp Asp Met
100 105 110

Arg Gly Glu Leu Lys Asn Cys Ser Phe Asn Met Thr Thr Glu Leu Arg
115 120 125

Asp Lys Lys Gln Lys Val Tyr Ser Leu Phe Tyr Arg Leu Asp Val Val
130 135 140

Gln Ile Asn Glu Asn Gln Gly Asn Arg Ser Asn Asn Ser Asn Lys Glu
145 150 155 160

Tyr Arg Leu Ile Asn Cys Asn Thr Ser Ala Ile Thr Gln Ala Cys Pro
165 170 175

Lys Val Ser Phe Glu Pro Ile Pro Ile His Tyr Cys Ala Pro Ala Gly
180 185 190

Phe Ala Ile Leu Lys Cys Lys Asp Lys Lys Phe Asn Gly Thr Gly Pro
195 200 205

Cys Pro Ser Val Ser Thr Val Gln Cys Thr His Gly Ile Lys Pro Val
210 215 220

Val Ser Thr Gln Leu Leu Leu Asn Gly Ser Leu Ala Glu Glu Glu Val
225 230 235 240

Met Ile Arg Ser Glu Asn Ile Thr Asn Asn Ala Lys Asn Ile Leu Val
245 250 255

Gln Phe Asn Thr Pro Val Gln Ile Asn Cys Thr Arg Pro Asn Asn Asn
260 265 270

Thr Arg Lys Ser Ile Arg Ile Gly Pro Gly Gln Ala Phe Tyr Ala Thr
275 280 285

Gly Asp Ile Ile Gly Asp Ile Arg Gln Ala His Cys Asn Val Ser Lys
290 295 300

Ala Thr Trp Asn Glu Thr Leu Gly Lys Val Val Lys Gln Leu Arg Lys
305 310 315 320

His Phe Gly Asn Asn Thr Ile Ile Arg Phe Ala Asn Ser Ser Gly Gly
325 330 335

Asp Leu Glu Val Thr Thr His Ser Phe Asn Cys Gly Gly Glu Phe Phe
340 345 350

Tyr Cys Asn Thr Ser Gly Leu Phe Asn Ser Thr Trp Ile Ser Asn Thr
355 360 365

Ser Val Gln Gly Ser Asn Ser Thr Gly Ser Asn Asp Ser Ile Thr Leu
370 375 380

Pro Cys Arg Ile Lys Gln Ile Ile Asn Met Trp Gln Arg Ile Gly Gln
385 390 395 400

Ala Met Tyr Ala Pro Pro Ile Gln Gly Val Ile Arg Cys Val Ser Asn
405 410 415

Ile Thr Gly Leu Ile Leu Thr Arg Asp Gly Gly Ser Thr Asn Ser Thr
420 425 430

Thr Glu Thr Phe Arg Pro Gly Gly Gly Asp Met Arg Asp Asn Trp Arg
435 440 445

Ser Glu Leu Tyr Lys Tyr Lys Val Val Lys Ile Glu Pro Leu Gly Val
450 455 460

Ala Pro Thr Arg Cys Lys Arg Arg Val Val Gly Arg Arg Arg Arg Arg
465 470 475 480

Arg Ala Val Gly Ile Gly Ala Val Phe Leu Gly Phe Leu Gly Ala Ala
485 490 495

Gly Ser Thr Met Gly Ala Ala Ser Met Thr Leu Thr Val Gln Ala Arg
500 505 510

Asn Leu Leu Ser Gly Ile Val Gln Gln Gln Ser Asn Leu Leu Arg Ala
515 520 525

Pro Glu Ala Gln Gln His Leu Leu Lys Leu Thr Val Trp Gly Ile Lys
530 535 540

Gln Leu Gln Ala Arg Val Leu Ala Val Glu Arg Tyr Leu Arg Asp Gln
545 550 555 560

Gln Leu Leu Gly Ile Trp Gly Cys Ser Gly Lys Leu Ile Cys Cys Thr
565 570 575

Asn Val Pro Trp Asn Ser Ser Trp Ser Asn Arg Asn Leu Ser Glu Ile
580 585 590

Trp Asp Asn Met Thr Trp Leu Gln Trp Asp Lys Glu Ile Ser Asn Tyr
595 600 605

Thr Gln Ile Ile Tyr Gly Leu Leu Glu Glu Ser Gln Asn Gln Gln Glu
610 615 620

Lys Asn Glu Gln Asp Leu Leu Ala Leu Asp
625 630

<210> SEQ ID NO 114
<211> LENGTH: 666
<212> TYPE: PRT
<213> ORGANISM: Artificial Sequence
<220> FEATURE:
<223> OTHER INFORMATION: Recombinantly produced polypeptide

<400> SEQUENCE: 114

Met Asp Ala Met Lys Arg Gly Leu Cys Cys Val Leu Leu Leu Cys Gly
1 5 10 15

Ala Val Phe Val Ser Pro Ser Gln Glu Ile His Ala Arg Phe Arg Arg
20 25 30

```
Ala Glu Asn Leu Trp Val Thr Val Tyr Tyr Gly Val Pro Val Trp Lys
        35                  40                  45

Asp Ala Glu Thr Thr Leu Phe Cys Ala Ser Asp Ala Lys Ala Tyr Glu
    50                  55                  60

Thr Glu Lys His Asn Val Trp Ala Thr His Ala Cys Val Pro Thr Asp
65                  70                  75                  80

Pro Asn Pro Gln Glu Ile His Leu Glu Asn Val Thr Glu Glu Phe Asn
                85                  90                  95

Met Trp Lys Asn Asn Met Val Glu Gln Met His Thr Asp Ile Ile Ser
            100                 105                 110

Leu Trp Asp Gln Ser Leu Lys Pro Cys Val Lys Leu Thr Pro Leu Cys
        115                 120                 125

Val Thr Leu Gln Cys Thr Asn Val Thr Asn Asn Ile Thr Asp Asp Met
    130                 135                 140

Arg Gly Glu Leu Lys Asn Cys Ser Phe Asn Met Thr Thr Glu Leu Arg
145                 150                 155                 160

Asp Lys Lys Gln Lys Val Tyr Ser Leu Phe Tyr Arg Leu Asp Val Val
                165                 170                 175

Gln Ile Asn Glu Asn Gln Gly Asn Arg Ser Asn Asn Ser Asn Lys Glu
            180                 185                 190

Tyr Arg Leu Ile Asn Cys Asn Thr Ser Ala Ile Thr Gln Ala Cys Pro
        195                 200                 205

Lys Val Ser Phe Glu Pro Ile Pro Ile His Tyr Cys Ala Pro Ala Gly
    210                 215                 220

Phe Ala Ile Leu Lys Cys Lys Asp Lys Lys Phe Asn Gly Thr Gly Pro
225                 230                 235                 240

Cys Pro Ser Val Ser Thr Val Gln Cys Thr His Gly Ile Lys Pro Val
                245                 250                 255

Val Ser Thr Gln Leu Leu Leu Asn Gly Ser Leu Ala Glu Glu Glu Val
            260                 265                 270

Met Ile Arg Ser Glu Asn Ile Thr Asn Asn Ala Lys Asn Ile Leu Val
        275                 280                 285

Gln Phe Asn Thr Pro Val Gln Ile Asn Cys Thr Arg Pro Asn Asn Asn
    290                 295                 300

Thr Arg Lys Ser Ile Arg Ile Gly Pro Gly Gln Ala Phe Tyr Ala Thr
305                 310                 315                 320

Gly Asp Ile Ile Gly Asp Ile Arg Gln Ala His Cys Asn Val Ser Lys
                325                 330                 335

Ala Thr Trp Asn Glu Thr Leu Gly Lys Val Val Lys Gln Leu Arg Lys
            340                 345                 350

His Phe Gly Asn Asn Thr Ile Ile Arg Phe Ala Asn Ser Ser Gly Gly
        355                 360                 365

Asp Leu Glu Val Thr Thr His Ser Phe Asn Cys Gly Gly Glu Phe Phe
    370                 375                 380

Tyr Cys Asn Thr Ser Gly Leu Phe Asn Ser Thr Trp Ile Ser Asn Thr
385                 390                 395                 400

Ser Val Gln Gly Ser Asn Ser Thr Gly Ser Asn Asp Ser Ile Thr Leu
                405                 410                 415

Pro Cys Arg Ile Lys Gln Ile Ile Asn Met Trp Gln Arg Ile Gly Gln
            420                 425                 430

Ala Met Tyr Ala Pro Pro Ile Gln Gly Val Ile Arg Cys Val Ser Asn
        435                 440                 445
```

-continued

```
Ile Thr Gly Leu Ile Leu Thr Arg Asp Gly Gly Ser Thr Asn Ser Thr
    450                 455                 460

Thr Glu Thr Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Arg Cys Lys Arg Arg Val Val Gly Arg Arg Arg Arg Arg
            500                 505                 510

Arg Ala Val Gly Ile Gly Ala Val Phe Leu Gly Phe Leu Gly Ala Ala
        515                 520                 525

Gly Ser Thr Met Gly Ala Ala Ser Met Thr Leu Thr Val Gln Ala Arg
    530                 535                 540

Asn Leu Leu Ser Gly Ile Val Gln Gln Gln Ser Asn Leu Leu Arg Ala
545                 550                 555                 560

Pro Glu Ala Gln Gln His Leu Leu Lys Leu Thr Val Trp Gly Ile Lys
                565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Cys Thr
        595                 600                 605

Asn Val Pro Trp Asn Ser Ser Trp Ser Asn Arg Asn Leu Ser Glu Ile
    610                 615                 620

Trp Asp Asn Met Thr Trp Leu Gln Trp Asp Lys Glu Ile Ser Asn Tyr
625                 630                 635                 640

Thr Gln Ile Ile Tyr Gly Leu Leu Glu Glu Ser Gln Asn Gln Gln Glu
                645                 650                 655

Lys Asn Glu Gln Asp Leu Leu Ala Leu Asp
            660                 665
```

ANTIBODIES CAPABLE OF BINDING HIV GP120 AND METHODS OF USE THEREOF

This application is the U.S. national phase of International Application No. PCT/US2020/057816, filed Oct. 29, 2020, which designated the U.S. and claims the benefit of priority of U.S. Provisional Application No. 62/927,239, filed Oct. 29, 2019, each of which is incorporated by reference in its entirety.

GOVERNMENT INTEREST

The invention was made with government support under Grant No. AID-OAA-A-16-00032 awarded by the USAID and Grant No. AI 144462 awarded by the NIH. The U.S. government has certain rights in the invention.

FIELD OF THE INVENTION

The field of the invention generally relates to anti-HIV Env antibodies and their use in the treatment or prevention of HIV/AIDS.

REFERENCE TO SEQUENCE LISTING SUBMITTED ELECTRONICALLY

The content of the electronically submitted sequence listing (Name: 6765_0510_Sequence_Listing.txt; Size: 92.8 kilobytes; and Date of Creation: Apr. 22, 2022) filed with the application is incorporated herein by reference in its entirety.

BACKGROUND

In 2015, there were approximately 2.1 million new human immunodeficiency virus (HIV) infections, over 36.7 million people living with HIV, and 1.1 million acquired immune deficiency syndrome (AIDS) related deaths. unaids.org/en/resources/fact-sheet (accessed on Jun. 29, 2017) While great progress has been made in the treatment of HIV/AIDS, all individuals living with HIV will have to be treated with anti-retroviral therapy (ART) for the rest of their lives since drug therapy is unable to clear latent viral reservoirs that exist in resting CD4+ T cells at a frequency of about $1/10^6$ cells. See, Eriksson, S. 2013. *PLoS Pathog* 9:e1003174.

HIV isolates can be classified into different groups and clades based on genotype and geographic location. For example, the population episensus (i.e., epitope based consensus sequence) antigen is central to the B clade epidemic in the United States while the population episensus antigen is central to the HIV C clade epidemic in South Africa. Broadly neutralizing anti-Env antibodies, for example PGDM1400 can neutralize more than one HIV isolate. U.S. Pat. Appl. Pub No. 20150361160.

Until a vaccine is discovered, many agree that a single product or approach will not completely halt new HIV infections. Accordingly, the use of HIV broadly neutralizing antibodies (bnAbs) has the potential to complement existing prevention methods by addressing important shortfalls or gaps in current product profiles. To achieve the goal of making bnAbs affordable and feasible products for widespread use in HIV prevention efforts, maximizing the potency of current and future bnAb candidates represents a promising and inadequately explored opportunity.

Thus, there remains a need for the development of broadly neutralizing antibodies that can be used in the treatment and prevention of HIV.

BRIEF SUMMARY

In one aspect, provided herein are enhanced engineered anti-HIV Env antibodies that were derived from the PGDM1400 parent antibody using directed-evolution and yeast display.

In one aspect, provided herein are pharmaceutical compositions comprising the enhanced engineered anti-HIV Env antibodies disclosed herein.

In one aspect, provided herein are isolated polynucleotides encoding the enhanced engineered anti-HIV Env antibodies disclosed herein.

In one aspect, provided herein are methods of producing the enhanced engineered anti-HIV Env antibodies disclosed herein.

In one aspect, provided herein are methods of neutralizing an HIV virus, comprising contacting the virus with the enhanced engineered anti-HIV Env antibodies disclosed herein.

In one aspect, provided herein are methods of reducing the likelihood of HIV infection in a subject exposed to HIV comprising administering to the subject the enhanced engineered anti-HIV Env antibodies disclosed herein.

In one aspect, provided herein are methods of treating HIV/AIDS comprising administering to a subject in need thereof the enhanced engineered anti-HIV Env antibodies disclosed herein.

In one aspect, provided herein are methods of reducing viral load comprising administering to a subject in need thereof the enhanced engineered anti-HIV Env antibodies disclosed herein.

In one aspect, provided herein are methods of producing an engineered variant of PGDM1400.

In some embodiments, the disclosure provides:

[1.] An antibody or antigen binding fragment thereof capable of binding HIV gp120, wherein the antibody or antigen binding fragment thereof comprises a VH and a VL, wherein the VH comprises a VH CDR1, VH CDR2, and VH CDR3, and the VL comprises a VL CDR1, VL CDR2, and VL CDR3, wherein a) the VH CDR1 comprises the sequence of SEQ ID NO: 94;

b) the VH CDR2 comprises the sequence of SEQ ID NO: 95;

c) the VH CDR3 comprises the sequence of SEQ ID NO 96;

d) the VL CDR1 comprises the sequence of SEQ ID NO: 97;

e) the VL CDR2 comprises the sequence of SEQ ID NO: 98; and f) the VL CDR3 comprises the sequence of SEQ ID NO: 99;

wherein at least one of the VH CDR1, VH CDR2, VH CDR3, VL CDR1, VL CDR2, and VL CDR3 comprises a different amino acid sequence than the corresponding CDR of the PGDM1400 antibody.

[2.] The antibody or antigen binding fragment thereof of [1], wherein the VH CDR1 comprises SEQ ID NO: 37; the VH CDR2 comprises the sequence of SEQ ID NO: 38 or 39; the VH CDR3 comprises the sequence of 31-35; the VL CDR1 comprises the sequence of SEQ ID NO: 41-44; the VL CDR2 comprises the sequence of SEQ ID NO: 45 or 46; and/or the VL CDR3 comprises the sequence of SEQ ID NO: 30.

[3.] The antibody or antigen binding fragment thereof of [1], wherein a) the VH CDR1, VH CDR2, and VH CDR3 comprises the sequence of SEQ ID NO: 37, 38, and 31; SEQ ID NO: 37, 38, and 32; SEQ ID NO: 37, 38, and 33; SEQ ID NO: 37, 38, and 34; SEQ ID NO: 37, 38, and 35; and SEQ ID NO: 37, 39, and 31, respectively; and/or b) the VL CDR1, VL CDR2 and VLCDR3 comprises the sequence of SEQ ID NO: 41, 46, and 30, respectively; SEQ ID NO: 42, 45, and 30, respectively; SEQ ID NO: 41, 45, and 30, respectively; SEQ ID NO: 43, 45, and 30, respectively; SEQ ID NO: 43, 46, and 30, respectively; SEQ ID NO: 44, 45, and 30, respectively.

[4.] The antibody or antigen binding fragment thereof of [1], wherein the VH CDR1, VH CDR2, VH CDR3, VL CDR1, VL CDR2, and VL CDR3 comprises the sequence of SEQ ID NO: 36, 38, 29, 41, 46, and 30, respectively; SEQ ID NO: 36, 38, 29, 42, 45, and 30, respectively; SEQ ID NO: 36, 38, 29, 41, 45, and 30, respectively; SEQ ID NO: 36, 38, 29, 43, 45, and 30, respectively; SEQ ID NO: 36, 38, 29, 43, 46, and 30, respectively; SEQ ID NO: 36, 38, 29, 44, 45, and 30, respectively; SEQ ID NO: 37, 38, 31, 40, 45, and 30, respectively; SEQ ID NO: 37, 38, 31, 41, 46, and 30, respectively; SEQ ID NO: 37, 38, 31, 42, 45, and 30, respectively; SEQ ID NO: 37, 38, 31, 41, 45, and 30, respectively; SEQ ID NO: 37, 38, 31, 43, 45, and 30, respectively; SEQ ID NO: 37, 38, 31, 43, 46, and 30, respectively; SEQ ID NO: 37, 38, 31, 44, 45, and 30, respectively; SEQ ID NO: 37, 38, 32, 40, 45, and 30, respectively; SEQ ID NO: 37, 38, 32, 41, 46, and 30, respectively; SEQ ID NO: 37, 38, 32, 42, 45, and 30, respectively; SEQ ID NO: 37, 38, 32, 41, 45, and 30, respectively; SEQ ID NO: 37, 38, 32, 43, 45, and 30, respectively; SEQ ID NO: 37, 38, 32, 43, 46, and 30, respectively; SEQ ID NO: 37, 38, 32, 44, 45, and 30, respectively; SEQ ID NO: 37, 38, 33, 40, 45, and 30, respectively; SEQ ID NO: 37, 38, 33, 41, 46, and 30, respectively; SEQ ID NO: 37, 38, 33, 42, 45, and 30, respectively; SEQ ID NO: 37, 38, 33, 41, 45, and 30, respectively; SEQ ID NO: 37, 38, 33, 43, 45, and 30, respectively; SEQ ID NO: 37, 38, 33, 43, 46, and 30, respectively; SEQ ID NO: 37, 38, 33, 44, 45, and 30, respectively; SEQ ID NO: 37, 38, 34, 40, 45, and 30, respectively; SEQ ID NO: 37, 38, 34, 41, 46, and 30, respectively; SEQ ID NO: 37, 38, 34, 42, 45, and 30, respectively; SEQ ID NO: 37, 38, 34, 41, 45, and 30, respectively; SEQ ID NO: 37, 38, 34, 43, 45, and 30, respectively; SEQ ID NO: 37, 38, 34, 43, 46, and 30, respectively; SEQ ID NO: 37, 38, 34, 44, 45, and 30, respectively; SEQ ID NO: 37, 38, 35, 40, 45, and 30, respectively; SEQ ID NO: 37, 38, 35, 41, 46, and 30, respectively; SEQ ID NO: 37, 38, 35, 42, 45, and 30, respectively; SEQ ID NO: 37, 38, 35, 41, 45, and 30, respectively; SEQ ID NO: 37, 38, 35, 43, 45, and 30, respectively; SEQ ID NO: 37, 38, 35, 43, 46, and 30, respectively; SEQ ID NO: 37, 38, 35, 44, 45, and 30, respectively; SEQ ID NO: 37, 39, 31, 40, 45, and 30, respectively; SEQ ID NO: 37, 39, 31, 41, 46, and 30, respectively; SEQ ID NO: 37, 39, 31, 42, 45, and 30, respectively; SEQ ID NO: 37, 39, 31, 41, 45, and 30, respectively; SEQ ID NO: 37, 39, 31, 43, 45, and 30, respectively; SEQ ID NO: 37, 39, 31, 43, 46, and 30, respectively; SEQ ID NO: 37, 39, 31, 44, 45, and 30, respectively; SEQ ID NO: 37, 39, 34, 40, 45, and 30, respectively; SEQ ID NO: 37, 39, 34, 41, 46, and 30, respectively; SEQ ID NO: 37, 39, 34, 42, 45, and 30, respectively; SEQ ID NO: 37, 39, 34, 41, 45, and 30, respectively; SEQ ID NO: 37, 39, 34, 43, 45, and 30, respectively; SEQ ID NO: 37, 39, 34, 43, 46, and 30, respectively; SEQ ID NO: 37, 39, 34, 44, 45, and 30, respectively.

[5.] The antibody or antigen binding fragment thereof of any one of [1] to [4], wherein the VH further comprises a VH FR1, VH FR2, VH FR3, and VH FR4, wherein (i) the VH FR1 comprises the sequence of SEQ ID NO: 100;

(ii) the VH FR2 comprises the sequence of SEQ ID NO: 101;

(iii) the VH FR3 comprises the sequence of SEQ ID NO: 102; and/or (iv) the VH FR4 comprises the sequence of SEQ ID NO: 104.

[6.] The antibody or antigen binding fragment thereof of [5], wherein the VH FR1 comprises the sequence of SEQ ID NO: 47-53; the VH FR2 comprises the sequence of SEQ ID NO: 54-57; the VH FR3 comprises the sequence of SEQ ID NO: 58-65; and/or the VH FR4 comprises the sequence of SEQ ID NO: 66.

[7.] The antibody or antigen binding fragment thereof of [5], wherein the VH FR1, VH FR2, VH FR3, and VH FR4 comprises the sequence of SEQ ID NO: 47, 54, 58, and 66, respectively; SEQ ID NO: 48, 55, 59, and 66, respectively; SEQ ID NO: 49, 56, 60, and 66, respectively; SEQ ID NO: 50, 55, 61, and 66, respectively; SEQ ID NO: 51, 55, 62, and 66, respectively; SEQ ID NO: 52, 56, 63, and 66, respectively; SEQ ID NO: 50, 54, 59, and 66, respectively; SEQ ID NO: 53, 55, 64, and 66, respectively; SEQ ID NO: 52, 55, 65, and 66, respectively; SEQ ID NO: 53, 57, 61, and 66, respectively; SEQ ID NO: 51, 55, 59, and 66, respectively.

[8.] The antibody or antigen binding fragment thereof of any one of [1] to [7], wherein the VL further comprises a VL FR1, VL FR2, VL FR3, and VL FR4, wherein (i) the VL FR1 comprises the sequence of SEQ ID NO: 104;

(ii) the VL FR2 comprises the sequence of SEQ ID NO: 105;

(iii) the VL FR3 comprises the sequence of SEQ ID NO: 106; and/or (iv) the VL FR4 comprises the sequence of SEQ ID NO: 107.

[9.] The antibody or antigen binding fragment thereof of [8], wherein the VL FR1 comprises the sequence of SEQ ID NO: 67-74; the VL FR2 comprises the sequence of SEQ ID NO: 75-81; the VL FR3 comprises the sequence of SEQ ID NO: 82-92; and/or the VL FR4 comprises the sequence of SEQ ID NO: 93.

[10.] The antibody or antigen binding fragment thereof of [9], wherein the VL FR1, VL FR2, VL FR3, and VL FR4 comprises the sequence of SEQ ID NO: 67, 75, 82, and 93, respectively; SEQ ID NO: 68, 76, 83, and 93, respectively; SEQ ID NO: 69, 77, 84, and 93, respectively; SEQ ID NO: 70, 78, 85, and 93, respectively; SEQ ID NO: 71, 79, 86, and 93, respectively; SEQ ID NO: 72, 80, 87, and 93, respectively; SEQ ID NO: 68, 76, 88, and 93, respectively; SEQ ID NO: 69, 78, 89, and 93, respectively; SEQ ID NO: 69, 79, 89, and 93, respectively; SEQ ID NO: 69, 80, 90, and 93, respectively; SEQ ID NO: 73, 80, 91, and 93, respectively; SEQ ID NO: 68, 80, 88, and 93, respectively; SEQ ID NO: 74, 79, 88, and 93, respectively; SEQ ID NO: 69, 78, 92, and 93, respectively; SEQ ID NO: 74, 76, 91, and 93, respectively; SEQ ID NO: 74, 80, 91, and 93, respectively; SEQ ID NO: 69, 81, 85, and 93, respectively.

[11.] The antibody or antigen binding fragment thereof of any one of [1] to [10], wherein the VH framework regions comprise one or more of A at H2, Q at H3, V at H5, A at H9, A at H16, N at H24, Q at H39, E at H46, E at H56, A at H58, K at H60, QGR at H62-H64, D at H66, G at H, and 81E at H85, wherein the VH framework residues are numbered according to Kabat.

[12.] The antibody or antigen binding fragment thereof of [11], wherein the VH framework regions comprise two or more, three or more, four or more, or five or more of a A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat.

[13.] The antibody or antigen binding fragment thereof of [12], wherein the VH framework regions comprise a A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat.

[14.] The antibody or antigen binding fragment thereof of [12], wherein the VH framework regions comprise one or more of a Q at H3, V at H5, N at H24, and E at H85, wherein the VH framework residues are numbered according to Kabat.

[15.] The antibody or antigen binding fragment thereof of [12], wherein the VH framework regions comprise Q at H3, V at H5, N at H24, and E at H85, wherein the VH framework residues are numbered according to Kabat.

[16.] The antibody or antigen binding fragment thereof of [12], wherein the VH framework regions comprise one or more of a A at H2, Q at H3, V at H5, N at H24, Q at H39, and E at H85, wherein the VH framework residues are numbered according to Kabat.

[17.] The antibody or antigen binding fragment thereof of [12], wherein the VH framework regions comprise A at H2, Q at H3, V at H5, N at H24, Q at H39, and E at H85, wherein the VH framework residues are numbered according to Kabat.

[18.] The antibody or antigen binding fragment thereof of any one of [1] to [17], wherein the VH has at least about 70%, at least about 75%, at least about 80%, at least about 90%, or at least about 95% sequence identity to SEQ ID NO: 1.

[19.] The antibody or antigen binding fragment thereof of any one of [1] to [17], wherein the VH has at least about 70%, at least about 75%, at least about 80%, at least about 90%, or at least about 95% sequence identity to SEQ ID NO: 3-12.

[20.] The antibody or antigen binding fragment thereof of any one of [1] to [18], wherein the VL framework regions comprise one or more of a I at L2, L at L9, P at L18, D at L26, L at L37, K or Q at L42, L at L48, D at L49, E or D at L53, E or R at L68, S at L74, D at L76, and A at L80], wherein the VL framework residues are numbered according to Kabat.

[21.] The antibody or antigen binding fragment thereof of [20], wherein the VL framework regions comprise two or more, three or more, four or more, or five or more of a I at L2, L at L9, P at L18, D at L26, L at L37, K or Q at L42, L at L48, D at L49, E or D at L53, E or R at L68, S at L74, D at L76, and A at L80], wherein the VL framework residues are numbered according to Kabat.

[22.] The antibody or antigen binding fragment thereof of [20], wherein the VL framework regions comprise a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat.

[23.] The antibody or antigen binding fragment thereof of [20], wherein the VL framework regions comprise one or more of a I at L2, L at L9, D at L26, E at L53, R at L68, D at L76, and A at L80], wherein the VL framework residues are numbered according to Kabat.

[24.] The antibody or antigen binding fragment thereof of [20], wherein the VL framework regions comprise a I at L2, L at L9, D at L26, E at L53, R at L68, D at L76, and A at L80, wherein the VL framework residues are numbered according to Kabat.

[25.] The antibody or antigen binding fragment thereof of [20], wherein the VL framework regions comprise one or more of L at L9, E at L53, R at L68, S at L74, D at L76, and A at L80, wherein the VL framework residues are numbered according to Kabat.

[26.] The antibody or antigen binding fragment thereof of [20], wherein the VL framework regions comprise a L at L9, E at L53, R at L68, S at L74, D at L76, and A at L80, wherein the VL framework residues are numbered according to Kabat.

[27.] The antibody or antigen binding fragment thereof of [20], wherein the VL framework regions comprise a one or more of I at L2, L at L9, L at L48, E at L53, E at L68, wherein the VL framework residues are numbered according to Kabat.

[28.] The antibody or antigen binding fragment thereof of [20], wherein the VL framework regions comprise a I at L2, L at L9, L at L48, E at L53, E at L68, wherein the VL framework residues are numbered according to Kabat.

[29.] The antibody or antigen binding fragment thereof of [20], wherein the VL framework regions comprise a one or more of D at L49, E or D at L53, E or R at L68, wherein the VL framework residues are numbered according to Kabat.

[30.] The antibody or antigen binding fragment thereof of [20], wherein the VL framework regions comprise a D at L49, E or D at L53, E or R at L68, wherein the VL framework residues are numbered according to Kabat.

[31.] The antibody or antigen binding fragment thereof of any one of [1] to [30], wherein the VL has at least about 70%, at least about 75%, at least about 80%, at least about 90%, or at least about 95% sequence identity to SEQ ID NO: 2.

[32.] The antibody or antigen binding fragment thereof of any one of [1] to [30], wherein the VL has at least about 70%, at least about 75%, at least about 80%, at least about 90%, or at least about 95% sequence identity to SEQ ID NO: 13-28.

[33.] The antibody or antigen binding fragment thereof of any one of [1] to [32], wherein the VL comprises SEQ ID NO: 13-28.

[34.] The antibody or antigen binding fragment thereof of any one of [1] to [33], wherein the VH comprises SEQ ID NO: 3-12.

[35.] An antibody or antigen binding fragment thereof capable of binding to HIV gp120, wherein the antibody or antigen binding fragment thereof comprises a VH CDR1, VH CDR2, VH CDR3, VL CDR1, VL CDR2, VL CDR3, and VH and VL framework regions, wherein a) the VH CDR1 comprises the sequence of SEQ ID NO: 94;

b) the VH CDR2 comprises the sequence of SEQ ID NO: 95;

c) the VH CDR3 comprises the sequence of SEQ ID NO: 96;

d) the VL CDR1 comprises the sequence of SEQ ID NO: 97;

e) the VL CDR2 comprises the sequence of SEQ ID NO: 98; and f) the VL CDR3 comprises the sequence of SEQ ID NO: 99;

and wherein the VH and VL framework regions comprise one or more of a A at H2, Q at H3, V at H5, A at H9, A at H16, N at H24, Q at H39, E at H46, E at H56, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80, wherein the VH and VL framework residues are numbered according to Kabat.

[36.] The antibody or antigen binding fragment thereof of [35], wherein the VH and VL framework regions comprise two or more, three or more, four or more, or five or more of A at H2, Q at H3, V at H5, A at H9, A at H16, N at H24, Q at H39, E at H46, E at H56, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80.

[37.] The antibody or antigen binding fragment thereof of [35], wherein the VH and VL framework regions comprise a A at H2, Q at H3, V at H5, A at H9, A at H16, N at H24, Q at H39, E at H46, E at H56, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80.

[38.] The antibody or antigen binding fragment of [35], wherein the VH and VL framework regions comprise one or more of a Q at H3, V at H5, N at H24, E at H85, D at L49, E or D at L53, and E or R at L68.

[39.] The antibody or antigen binding fragment of [35], wherein the VH and VL framework regions comprise one or more of a A at H2, Q at H3, V at H5, N at H24, Q at H39, E at H85, I at L2, L at L9, D at L26, E at L53, R at L68, D at L76, and A at L80.

[40.] The antibody or antigen binding fragment of [35], wherein the VH and VL framework regions comprise one or more of a A at H2, Q at H3, V at H5, N at H24, Q at H39, E at H85, L at L9, E at L53, R at L68, S at L74, D at L76, and A at L80.

[41.] The antibody or antigen binding fragment of [35], wherein the VH and VL framework regions comprise one or more of a A at H2, Q at H3, V at H5, N at H24, Q at H39, E at H85, I at L2, L at L9, L at L48, E at L53, and E at L68.

[42.] The antibody or antigen binding fragment thereof of any one of [35] to [41], wherein the VH comprises the amino acid sequence of SEQ ID NO: 3-12.

[43.] The antibody or antigen binding fragment thereof of any one of [35] to [42], wherein the VL comprises the amino acid sequence of SEQ ID NO: 13-28.

[44.] An antibody or antigen binding fragment thereof capable of binding to HIV gp120, wherein the antibody comprises a VH having at least about 70%, at least about 75%, at least about 80%, or at least about 90% sequence identity to SEQ ID NO: 1 and a VL having at least about 70%, at least about 75%, at least about 80%, or at least about 90% sequence identity SEQ ID NO: 2, wherein (i) the VH comprises one or more of a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104, wherein the VH residues are numbered according to Kabat; and (ii) the VL comprises one or more of a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80, wherein the VL residues are numbered according to Kabat.

[45.] The antibody or antigen binding fragment thereof of [44], wherein (i) the VH comprises two or more, three or more, four or more, or five or more of a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104, wherein the VH residues are numbered according to Kabat; and (ii) the VL comprises two or more, three or more, four or more, or five or more of a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80, wherein the VL residues are numbered according to Kabat.

[46.] The antibody or antigen binding fragment thereof of [44], wherein (i) the VH comprises a Q at H3, V at H5, N at H24, T at H30, E at H85, and A at H104, wherein the VH residues are numbered according to Kabat; and (ii) the VL comprises a D at L49, E or D at L53, and E or R at L68, wherein the VL residues are numbered according to Kabat.

[47.] The antibody or antigen binding fragment thereof of any one of [44] to [46], wherein (a) the VH CDR1 comprises the sequence of SEQ ID NO: 94;

(b) the VH CDR2 comprises the sequence of SEQ ID NO: 95;

(c) the VH CDR3 comprises the sequence of SEQ ID NO: 96;

(d) the VL CDR1 comprises the sequence of SEQ ID NO: 97;

(e) the VL CDR2 comprises the sequence of SEQ ID NO: 98; and (f) the VL CDR3 comprises the sequence of SEQ ID NO: 99.

[48.] The antibody or antigen binding fragment thereof of any one of [44] to [47], wherein the VH comprises the amino acid sequence of SEQ ID NO: 3-12.

[49.] The antibody or antigen binding fragment thereof of any one of [44] to [48], wherein the VL comprises the amino acid sequence of SEQ ID NO: 13-28.

[50.] An antibody or antigen binding fragment thereof capable of binding to HIV gp120, wherein the antibody comprises a VH having at least about 70%, at least about 75%, at least about 80%, or at least about 90% sequence identity to SEQ ID NO: 1 and a VL having at least about 70%, at least about 75%, at least about 80%, or at least about 90% sequence identity SEQ ID NO: 2, wherein the VH comprises one or more of a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104, wherein the VH residues are numbered according to Kabat.

[51.] The antibody or antigen binding fragment thereof of [50], wherein the VH comprises two or more, three or more, four or more, or five or more of a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104.

[52.] The antibody or antigen binding fragment thereof of [50], wherein the VH comprises a Q at H3, V at H5, N at H24, T at H30, E at H85, and A at H104.

[53.] The antibody or antigen binding fragment thereof of [50], wherein the VH comprises a A at H2, Q at H3, V at H5, N at H24, T at H30, Q at H39, E at H85, E at H100H, and A at H104.

[54.] The antibody or antigen binding fragment thereof of any one of [50] to [53], wherein the VL comprises one or more of a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80, wherein the VL residues are numbered according to Kabat.

[55.] The antibody or antigen binding fragment thereof of [54], wherein the VL comprises one or more of a D at L49, E or D at L53, and E or R at L68.

[56.] The antibody or antigen binding fragment thereof of [54], wherein the VL comprises one or more of a I at L2, L at L9, D at L26, Q at L27C, E at L53, R at L68, D at L76, and A at L80.

[57.] The antibody or antigen binding fragment thereof of [54], wherein the VL comprises one or more of a L at L9, Q at L27, E at L53, R at L68, S at L74, D at L76, and A at L80.

[58.] The antibody or antigen binding fragment thereof of [54], wherein the VL comprises one or more of a I at L2, L at L9, Q at L27C, L at L48, E at L53, and E at L68.

[59.] The antibody or antigen binding fragment thereof of any one of [50] to [58], wherein the VH comprises a VH CDR3 comprising the sequence of SEQ ID NO: 96.

[60.] The antibody or antigen binding fragment thereof of any one of [50] to [59], wherein the VH comprises
- (a) a VH CDR1 comprising the sequence of SEQ ID NO: 94;
- (b) a VH CDR2 comprising the sequence of SEQ ID NO: 95; and
- (c) a VH CDR3 comprising the sequence of SEQ ID NO: 96.

[61.] The antibody or antigen binding fragment thereof of any one of [50] to [60], wherein the VL comprises
- (a) a VL CDR1 comprising the sequence of SEQ ID NO: 97;
- (b) a VL CDR2 comprising the sequence of SEQ ID NO: 98; and
- (c) a VL CDR3 comprising the sequence of SEQ ID NO: 99.

[62.] The antibody or antigen binding fragment thereof of any one of [50] to [61], wherein the VL is SEQ ID NO: 13-28.

[63.] The antibody or antigen binding fragment thereof of any one of [50] to [62], wherein the VH comprises SEQ ID NO: 3-12.

[64.] The antibody or antigen binding fragment thereof of any one of [1] to [63], wherein at least one of the VH CDR1, VH CDR2, VH CDR3, VL CDR1, VL CDR2, and VL CDR3 comprises a different amino acid sequence than the corresponding CDR of the PGDM1400 antibody.

[65.] The antibody or antigen binding fragment thereof of any one of [1] to [64], which is not PGDM1400 or an antigen binding fragment thereof.

[66.] An antibody or antigen binding fragment thereof capable of binding to HIV gp120, wherein the antibody comprises
- (i) a VH comprising the amino acid sequence of SEQ ID NO: 3-12; and
- (ii) a VL comprising the amino acid sequence of SEQ ID NO: 13-28.

[67.] An antibody or antigen binding fragment thereof capable of binding to HIV gp120, wherein the antibody comprises
- (i) a VH comprising the amino acid sequence of SEQ ID NO: 9 and a VL comprising the amino acid sequence of SEQ ID NO: 17;
- (ii) a VH comprising the amino acid sequence of SEQ ID NO: 9 and a VL comprising the amino acid sequence of SEQ ID NO: 21; or
- (iii) a VH comprising the amino acid sequence of SEQ ID NO: 9 and a VL comprising the amino acid sequence of SEQ ID NO: 25.

[68.] The antibody or antigen binding fragment thereof of any one of [1] to [67], which is capable of competing with PGDM1400 for binding to HIV gp120.

[69.] The antibody or antigen binding fragment thereof of any one of [1] to [67], which binds to the same epitope of HIV gp120 as PGDM1400.

[70.] The antibody or antigen binding fragment thereof of any one of [1] to [69], wherein the HIV gp120 is BG505 gp120.

[71.] The antibody or antigen binding fragment thereof of any one of [1] to [70] that is a broadly neutralizing antibody.

[72.] The antibody or antigen binding fragment thereof of any one of [1] to [70] capable of neutralizing at least two cross-clade isolates of HIV.

[73.] The antibody or antigen binding fragment thereof of any one of [1] to [70] capable of neutralizing at least about 50%, 60%, 70%, 80%, 90%, or 100% of cross-clade HIV isolates in the 116-member indicator virus panel.

[74.] The antibody or antigen binding fragment thereof of any one of [1] to [70] capable of neutralizing at least about 50%, 60%, 70%, 80%, 90%, or 100% of cross-clade PGDM1400 resistant HIV isolates in the 30-member indicator virus panel.

[75.] The antibody or antigen binding fragment thereof of any one of [72] to [74], wherein the antibody or antigen binding fragment thereof is capable of neutralizing the cross-clade HIV isolates with a median IC50 equal to or less than about 0.1 μg/ml, 0.05 μg/ml, 0.025 g/ml, 0.01 μg/ml, or 0.005 μg/ml.

[76.] The antibody or antigen binding fragment thereof of any one of [1] to [75], wherein the antibody is a recombinant antibody, a chimeric antibody, a bispecific antibody, or a trispecific antibody.

[77.] The antibody or antigen binding fragment thereof of any one of [1] to [75], wherein the antibody is a bispecific antibody.

[78.] The antibody or antigen binding fragment thereof of any one of [1] to [75], wherein the antibody is a trispecific antibody.

[79.] The antibody or antigen binding fragment thereof of any one of [1] to [78], wherein the antibody fragment comprises a single-chain Fv (scFv), F(ab) fragment, F(ab')2 fragment, or an isolated VH domain.

[80.] The antibody or antigen binding fragment thereof of any one of [1] to [79], further comprising a heavy and/or light chain constant region.

[81.] The antibody or antigen binding fragment thereof of any one of [1] to [80], further comprising a human heavy and/or light chain constant region.

[82.] The antibody or antigen binding fragment thereof of [81], wherein the heavy chain constant region is human immunoglobulin IgG1, IgG2, IgG3, IgG4, IgA1, or IgA2 constant region.

[83.] The antibody or antigen binding fragment thereof of any one of [80] to [82], wherein the heavy chain constant region comprises a native amino acid sequence.

[84.] The antibody or antigen binding fragment thereof of any one of [80] to [82], wherein the heavy chain constant region comprises a variant amino acid sequence.

[85.] A pharmaceutical composition comprising the antibody or antigen binding fragment thereof of any one of [1] to [84] and a pharmaceutically acceptable excipient.

[86.] An isolated polynucleotide encoding the antibody or antigen binding fragment thereof of any one of [1] to [84].

[87.] The isolated polynucleotide of [86], which is a DNA.

[88.] The isolated polynucleotide of [86], which is an mRNA.

[89.] The isolated polynucleotide of [88], wherein the mRNA comprises a modified nucleotide.

[90.] An isolated vector comprising the polynucleotide of [86].

[91.] The isolated vector of [90], wherein the vector is a viral vector.

[92.] A recombinant virus comprising the polynucleotide of [86].

[93.] The recombinant virus of [92], which is a recombinant adeno-associated virus (AAV).

[94.] A host cell comprising the polynucleotide of [86] or the vector of [92].

[95.] The host cell of [94], which is *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, or human cell in tissue culture.

[96.] A method of producing the antibody or antigen binding fragment thereof of any one of [1] to [84] comprising culturing the host cell of [94] or [95] so that the antibody or antigen binding fragment thereof is expressed and the antibody or antigen binding fragment thereof is produced.

[97.] A method of neutralizing an HIV virus comprising contacting the virus with a sufficient amount of the antibody or antigen binding fragment thereof of any one of [1] to [84].

[98.] A method of reducing the likelihood of HIV infection in a subject exposed to HIV comprising administering to the subject a therapeutically sufficient amount of the antibody or antigen binding fragment thereof of any one of [1] to [84].

[99.] A method of treating HIV/AIDS comprising administering to a subject in need thereof a therapeutically sufficient amount of the antibody or antigen binding fragment thereof of any one of [1] to [84].

[100.] A method of reducing viral load comprising administering to a subject in need thereof a therapeutically sufficient amount of the antibody or antigen binding fragment thereof of any one of [1] to [84].

[101.] The method of [98] to [100], wherein the administering to the subject is by at least one mode selected from oral, parenteral, subcutaneous, intramuscular, intravenous, vaginal, rectal, buccal, sublingual, and transdermal.

[102.] The method of any one of [98] to [101], further comprising administering at least one additional therapeutic agent.

[103.] The method of [102], wherein the additional therapeutic agent is an antiretroviral agent, a reservoir activator, or a second antibody.

[104.] The method of [102], wherein the additional therapeutic agent comprises a broadly neutralizing antibody.

[105.] The method of [102], wherein the additional therapeutic agent comprises two broadly neutralizing antibodies.

[106.] The method of [102], wherein the additional therapeutic agent comprises three broadly neutralizing antibodies.

[107.] A method of producing an engineered variant of PGDM1400 comprising (i) substituting one or more amino acid residues of the PGDM1400 VH to a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104, wherein the VH residues are numbered according to Kabat; and/or (ii) substituting one or more amino acid residues of the PGDM1400 VL to a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80, wherein the VL residues are numbered according to Kabat.

BRIEF DESCRIPTION OF THE DRAWINGS

FIG. 1. Neutralization breadth of ePGDM9 (i.e., ePDGM1400v9-LS), and PGDM1400 antibodies on a 100 member clade C virus panel at different IC50 and IC80 cutoffs.

DETAILED DESCRIPTION

Provided herein are anti-HIV Env antibodies that were derived from the PGDM1400 parent antibody using directed-evolution and yeast display. In one embodiment, an antibody disclosed herein possesses one or more improved properties, for example, higher binding affinity to target antigen, increased median neutralization $IC_{50}$ potency, and increased breadth of neutralization compared to PGDM1400. Due to their significantly improved properties, in one embodiment, antibodies disclosed herein confer sterilizing immunity at lower doses and consequently both reduce the cost per dose and increase the number of doses that can be produced by a manufacturer. Thus the improved antibodies disclosed herein can achieve substantially decreased cost of goods and significantly increased numbers of people who can be protected against HIV.

One aspect of the present disclosure relates to improved anti-HIV Env antibodies, and to nucleotide sequences encoding, compositions comprising, and kits comprising thereof. In another aspect, it relates to methods of treatment and prevention of HIV using an antibody disclosed herein. In another aspect, it relates to methods of diagnosing and monitoring of HIV infection using an antibody disclosed herein.

I. Definitions

To facilitate an understanding of the present invention, a number of terms and phrases are defined below.

The terms "human immunodeficiency virus" or "HIV," as used herein, refer generally to a retrovirus that is the causative agent for acquired immunodeficiency syndrome (AIDS), variants thereof (e.g., simian acquired immunodeficiency syndrome, SAIDS), and diseases, conditions, or opportunistic infections associated with AIDS or its variants, and includes HIV-Type 1 (HIV-1) and HIV-Type 2 (HIV-2) of any clade or strain therein, related retroviruses (e.g., simian immunodeficiency virus (SIV)), and variants thereof (e.g., engineered retroviruses, e.g., chimeric HIV viruses, e.g., simian-human immunodeficiency viruses (SHIVs)). In one embodiment, an HIV virus is an HIV-Type-1 virus. Previous names for HIV include human T-lymphotropic virus-III (HTLV-III), lymphadenopathy-associated virus (LAV), and AIDS-associated retrovirus (ARV).

As used herein, the term "clade" refers to related human immunodeficiency viruses (HIVs) classified according to their degree of genetic similarity. There are currently four known groups of HIV-1 isolates: M, N, O, and P. Group M (major strains) viruses are responsible for the majority of the global HIV epidemic. The other three groups, i.e., N, O and P are quite uncommon and only occur in Cameroon, Gabon and Equatorial Guinea. In one embodiment, an HIV virus is a Group M HIV virus. Within group M there are known to be at least nine genetically distinct subtypes or clades of HIV-1: subtypes or clades A, B, C, D, F, G, H, J and K. Additionally, different subtypes can combine genetic material to form a hybrid virus, known as a 'circulating recombinant form' (CRFs). Subtype/clade B is the dominant HIV subtype in the Americas, Western Europe and Australasia. Subtype/clade C is very common in the high AIDS prevalence countries of Southern Africa, as well as in the horn of Africa and India. Just under half of all people living with HIV have subtype C. In certain exemplary embodiments, methods described herein can be used to treat a subject (e.g., a human) infected with HIV (e.g., HIV-1) or to block or prevent HIV (e.g., HIV-1) infection in subject (e.g., a human) at risk of HIV transmission. The HIV may be of two, three, four, five, six, seven, eight, nine, ten, or more clades and/or two or more groups of HIV.

Acquired immune deficiency syndrome ("AIDS") is a disease caused by the human immunodeficiency virus, or HIV.

As used herein, the term "envelope glycoprotein" or "Env" refers to the glycoprotein that is expressed on the surface of the envelope of HIV virions and the surface of the plasma membrane of HIV infected cells. "Envelope glycoprotein" or "Env" encompass, but are not limited to, native Env, an isoform of Env, or a variant of Env (e.g., SOSIP) derived from an HIV isolate, for example, BG505. Env is the sole virally encoded gene product on the surface of the virus and, as such, is the only target of neutralizing antibodies. Env is a trimer of heterodimers composed of two non-covalently associated subunits: the receptor-binding gp120 and the fusion machinery-containing gp41. Each subunit is derived from a gp160 precursor glycoprotein following cleavage by cellular furins. HIV-1 gp120 binds the CD4 molecule on the surface of human target T cells to initiate the viral entry process, and following co-receptor engagement, fusion is mediated by gp41. gp140 env is the uncleaved ectodomain of gp160. In one embodiment, Env is a BG505 Env polypeptide. UniProtKB accession number Q2N0S5-1, Q2N0S6-1, and Q2N0S7-1 provide BG505 env gp160 polypeptide sequences. In one embodiment, BG505 Env is BG505.W6M.ENV.C2 Env comprising the amino acid sequence of SEQ ID NO: 111 (MRVMGIQRNCQHL-FRWGTMILGMIIICSAAENLWVTVYYGVPVWK-DAETTLFCASDA KAYETEKHNVWATHACVPTDPNP QEIHLENVTEEFNMWKNNMVEQMHTDIISLWDQSL KPCVKLTPLCVTLQCTNVTN-NITDDMRGELKNCSFNMTTELRDKKQKVYS-LFYRLDVV QINENQGNRSNNSNKEYRLINCNT-SAITQACPKVSFEPIPIHYCAPAGFAILKCKDKKFNG TGPCPSVSTVQCTHGIKPVVSTQLLLNGS-LAEEEVMIRSENITNNAKNILVQFNTPVQINC TRPNNNTRKSIRIGPGQAFYATGDIIGDIRQAHCTV-SKATWNETLGKVVKQLRKHFGNNT IIR-FANSSGGDLEVTTHSFNCGGEFFYCNTSGLFNSTWIS-NTSVQGSNSTGSNDSITLPCRI KQIINMWQRIGQAMYAPPIQGVIRCVSNITGLIL-TRDGGSTNSTTETFRPGGGDMRDNWR SELYKYKVVKIEPLGVAPTRAKRRVVGREKRAV-GIGAVFLGFLGAAGSTMGAASMTLT VQARNLLS-GIVQQQSNLLRAIEAQQHLLKLTVWGIKQLQARV-LAVERYLRDQQLLGIWG CSGKLICTTNVPWNSSWSNRNL-SEIWDNMTWLQWDKEIS-NYTQIIYGLLEESQNQQEKN EQDLLALDK-WASLWNWFDISNWLWYIKIFIMIVGGLIGLRIVFAVLS VIHRVRQGYSPLS FQTHTPNPRGLDR-PERIEEEDGEQDRGRSTRLVSGFLALAWD-DLRSLCLFCYHRLRDFILI AARIVELLGH-SSLKGLRLGWEGLKYLWNLLAYWGRELKISAINLFD-TIAIAVAEWTDRVI EIGQRLCRAFLHIPRRIRQGLERALL). In one embodiment, BG505 Env is a variant of BG505.W6M.ENV.C2 Env comprising the T330N substitution (SEQ ID NO: 112 (MRVMGIQRNCQHLFRWGTMILGMIIICSAAE-NLWVTVYYGVPVWKDAETTLFCASDA KAY-ETEKHNVWATHACVPTDPNPQEIHLENVTEEFNMW-KNNMVEQMHTDIISLWDQSL KPCVKLTPLCVTLQCTNVTN-NITDDMRGELKNCSFNMTTELRDKKQKVYS-LFYRLDVV QINENQGNRSNNSNKEYRLINCNT-SAITQACPKVSFEPIPIHYCAPAGFAILKCKDKKFNG TGPCPSVSTVQCTHGIKPVVSTQLLLNGS-LAEEEVMIRSENITNNAKNILVQFNTPVQINC TRPNNNTRKSIRIGPGQAFYATGDIIGDIRQAHCNVSKATWNETLGKVVKQLRKHFGNN TIIRFANSSGGDLEVTTHSFNCGGEFFYCNTSGLFNSTWISNTSVQGSNSTGSNDSITLPCRI KQIINMWQRIGQAMYAPPIQGVIRCVSNITGLILTRDGGSTNSTTETFRPGGGDMRDNWR SELYKYKVVKIEPLGVAPTRAKRRVVGREKRAVGIGAVFLGFLGAAGSTMGAASMTLT VQARNLLSGIVQQQSNLLRAIEAQQHLLKLTVWGIKQLQARVLAVERYLRDQQLLGIWG CSGKLICTTNVPWNSSWSNRNLSEIWDNMTWLQWDKEISNYTQIIYGLLEESQNQQEKN EQDLLALDKWASLWNWFDISNWLWYIKIFIMIVGGLIGLRIVFAVLSVIHRVRQGYSPLS FQTHTPNPRGLDRPERIEEEDGEQDRGRSTRLVSGFLALAWDDLRSLCLFCYHRLRDFILI AARIVELLGHSSLKGLRLGWEGLKYLWNLLAYWGRELKISAINLFDTIAIAVAEWTDRVI EIGQRLCRAFLHIPRRIRQGLERALL)).

The term "well-ordered Env trimer" or "well-ordered trimer" as used herein refers to an envelope glycoprotein trimer comprising three cleaved gp140 polypeptides that closely mimics the quaternary structure of the Env ectodomain on the surface of the envelope of HIV or SIV virions and the surface of the plasma membrane of HIV or SIV infected cells. In one embodiment, the gp120 and gp41 ectodomain is linked by a covalent linkage, for example, a disulfide bond. In one embodiment, the gp140 polypeptide comprises one or more mutations to promote trimer formation. In one embodiment, the gp140 polypeptide comprises one or more mutations to promote disulfide formation. In one embodiment, the well-ordered trimer is an SOSIP gp140 trimer. Well-ordered SOSIP trimers have been disclosed in US Patent Appl. Pub. No. 2014/0212458, Sanders, R. W. et al., *PLoS Pathog.* 9, e1003618 (2013) and Guenaga J., et al., Immunity 46(5):792-803.e3 (2017), each of which is incorporated by reference herein in its entirety. In one embodiment, a well ordered trimer is formed from a clade A Env. In one embodiment, a well ordered trimer is formed from a clade B Env. In one embodiment, a well ordered trimer is formed from a clade C Env. In one embodiment, a well ordered trimer is formed from a circulating recombinant form Env. In one embodiment, a well ordered trimer is BG505 SOSIP. In one embodiment, a well ordered trimer is BG505 SOSIP.664. In one embodiment, BG505 SOSIP.664 comprises the amino acid sequence of SEQ ID NO: 113 (AENLWVTVYYGVPVWKDAETTLFCASDAKAYETEKHNVWATHACVPTDPNPQEIHLE NVTEEFNMWKNNMVEQMHTDIISLWDQSLKPCVKLTPLCVTLQCTNVTNNITDDMRGE LKNCSFNMTELRDKKQKVYSLFYRLDVVQINENQGNRSNNSNKEYRLINCNTSAITQA CPKVSFEPIPIHYCAPAGFAILKCKDKKFNGTGPCPSVSTVQ CTHGIKPVVSTQLLLNGSL AEEEVMIRSENITNNAKNILVQFNTPVQINCTRPNNNTRKSIRIGPGQAFYATGDIIGDIRQ AHCNVSKATWNETLGKVVKQLRKHFGNNTII RFANSSGGDLEVTTHSFNCGGEFFYCNT SGLFNSTWISNTSVQGSNSTGSNDSITLPCRIKQIINMWQRIGQAMYAPPIQGVIRCVSNIT GLILTRDGGSTNSTTETFRPGGGDMRDNWRSELYKYKVVKIEPLGVAPTRCKRRVVGRR RRRRAVGIGAVFLGFLGAAGSTMGAASMTLTVQARNLLSGIVQQQSNLLRAPEAQQHLL KLTVWGIKQLQARVLAVERYLRDQQLLGIWGCSGKLICCTNVPWNSSWSNRNLSEIWD NMTWLQWDKEISNYTQIIYGLLEESQNQQEKNEQDLLALD). In one embodiment, a nascent BG505 SOSIP.664 further comprises a leader sequence, wherein the nascent BC505 SOSIP.664 comprises the amino acid sequence of SEQ ID NO: 114 (MDAMKRGLCCVLLLCGAVFVSPSQEIHARFRRAENLWVTVYYGVPVWKDAETLFCA SDAKAYETEKHNVWATHACVPTDPNPQEIHLENVTEEFNMWKNNMVEQMHTDIISLW DQSLKPCVKLTPLCVTLQCTNVTNNITDDMRGELKNCSFNMTTELRDKKQKVYSLFYRL DVVQINENQGNRSNNSNKEYRLINCNTSAITQACPKVSFEPIPIHYCAPAGFAILKCKDKK FNGTOPCPSVSTVQCTHGIKPVVSTQLLLNGSLAEEEVMIRSENITNNAKNILVQFNTPVQ INCTRPNNNTRKSIRIGPGQAFYATGDIIGDIRQAHCNVSKATWNETLGKVVKQLRKHFG NNTIIRFANSSGGDLEVTTHSFNGGGEFFYCNTSGLFNSTWISNTSVQGSNSTGSNDSITLP CRIKQIINMWQRIGQAMYAPPIQGVIRCVSNITGLILTRDXGSTNSTTETFRPGGGDMRDN WRSELYKYKVVKIEPLGVAPTRCKRRVVGRRRRRRAVGIGAVFLGFLGAAGSTMGAAS MTLTVQARNLLSGIVQQQSNLLRAPEAQQHLLKLTVWGIKQLQARVLAVERYLRDQQL LGIWGCSGKLICCTNVPWNSSWSNRNLSEIWDNMTWLQWDKEISNYTQIIYGLLEESQN QQEKNEQDLLALD). In one embodiment, a well ordered trimer is BG505 SOSIP as disclosed in International Application No. PCT/US2018/041729, filed Jul. 12, 2018, which is incorporated herein by reference in its entirety for all purposes. In one embodiment, a well-ordered Env trimer is a native flexibly linked (NFL) trimer as described in Sharna, et al., Cell Reports. 11(4):539-50 (2015). In one embodiment, a well-ordered Env trimer is a DS-SOSIP as described in Chuang, et al., J. Virology. 91(10), pii: e02268-16 (2017). In one embodiment, a well ordered trimer is formed from a SIV Env. In one embodiment, a well ordered trimer is an SIV Env SOSIP. In one embodiment, a well ordered trimer is formed from an Env comprising a mutation (e.g., substitution or deletion) in the CD4 binding site. In one embodiment, a well ordered trimer is formed from an Env comprising a mutation (e.g., substitution or deletion) in the CD4 binding site wherein the mutation reduces or disrupts the binding between Env and CD4. In one embodiment, a well ordered trimer is a CRF or C108 SOSIP. See, e.g., Andrabi et al, Immunity 43(5): 959-973 (2015). In some embodiments, the gp120 and gp41 ectodomain is linked by a peptide linker, for example, a Gly-Ser linker, as described in Georgiev I S, et al., J. Virology 89(10): 5318-5329 (2015). In some embodiments, the well-ordered Env trimer is stable.

The term "antibody" means an immunoglobulin molecule (or a group of immunoglobulin molecules) that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), affybodies, Fab fragments, $F(ab')_2$ fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclasses (isotypes) thereof (e.g. IgG1, IgG2, IgG3, IgG4, IgA1 and IgA2), of immunoglobulin molecule, based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated or fused to other molecules such as toxins, radioisotopes, other polypeptides etc.

As used herein, the terms "antigen-binding domain," "antigen-binding region," "antigen-binding site," and similar terms refer to the portion of antibody molecules which comprises the amino acid residues that confer on the antibody molecule its specificity for the antigen (e.g., HIV Env). The antigen-binding region can be derived from any animal species, such as mouse and humans.

As used herein, the terms "variable region" or "variable domain" are used interchangeably and are common in the art. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen (e.g., HIV Env). In certain embodiments, the variable region comprises 3 CDRs (CDR1, CDR2, and CDR3) and 4 framework regions (FR1, FR2, FR3, and FR4) in the order of FR1-CDR1-FR2-CDR2-FR3-CDR3-FR4 from the N terminus to the C terminus. In certain embodiments, the variable region is a human variable region. In certain embodiments, the variable region comprises human CDRs and human framework regions (FRs). In certain embodiments, the variable region comprises CDRs and framework regions (FRs) wherein one or more of the CDRs were modified by a substitution, deletion, or insertion relative to the CDRs of a parental antibody. In certain embodiments, the variable region comprises CDRs and framework regions (FRs) wherein one or more of the FRs were modified by a substitution, deletion, or insertion relative to the FRs of a parental antibody. In certain embodiments, the variable region comprises CDRs and framework regions (FRs) wherein one or more of the CDRs and one or more of the FRs were modified by a substitution, deletion, or insertion relative to the CDRs and FRs of a parental antibody. In certain embodiments, the parental antibody is PGDM1400. In certain embodiments, the variable region comprises human CDRs and primate (e.g., non-human primate) framework regions (FRs).

A skilled artisan understands that there are at several techniques for determining CDRs. One approach is based on cross-species sequence variability (i.e., Kabat et al., *Sequences of Proteins of Immunological Interest*, (5th ed., 1991, National Institutes of Health, Bethesda Md.) ("Kabat"). Another approach is based on crystallographic studies of antigen-antibody complexes (Al-lazikani et al, *J. Molec. Biol.* 273:927-948 (1997)) ("Chothia"). In addition, combinations of these two approaches are sometimes used in the art to determine CDRs. In some embodiments, the CDR sequences are identified according to Kabat. In some embodiments, the CDR sequences are identified according to Chothia. It is understood that the identification of CDRs in a variable region also identifies the FRs as the sequences flanking the CDRs.

The Kabat numbering system is generally used when referring to a residue in the variable domain (approximately residues 1-107 of the light chain and residues 1-113 of the heavy chain) (e.g., Kabat et al., *Sequences of Immunological Interest*. (5th Ed., 1991, National Institutes of Health, Bethesda, Md.) ("Kabat").

The amino acid position numbering as in Kabat, refers to the numbering system used for heavy chain variable domains or light chain variable domains of the compilation of antibodies in Kabat et al. (*Sequences of Immunological Interest*. (5th Ed., 1991, National Institutes of Health, Bethesda, Md.), "Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. In some embodiments, the CDR sequences are identified according to Kabat. In some embodiments, the CDR sequences are identified according to Chotia. In some embodiments, the CDR sequences are identified according to AbM. In some embodiments, the VH CDR3 sequence is identified according to Kabat. In some embodiments, the VH CDR3 sequence is identified according to Chotia. In some embodiments, the VH CDR3 sequence is identified according to AbM.

| Loop | Kabat | AbM | Chothia |
|---|---|---|---|
| L1 | L24-134 | L24-134 | L24-134 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The terms 'VL' and "VL domain" are used interchangeably to refer to the light chain variable region of an antibody.

The terms "VH" and "VH domain" are used interchangeably to refer to the heavy chain variable region of an antibody.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "polyclonal antibody" describes a composition of different (diverse) antibody molecules which are capable of binding to or reacting with several different specific antigenic determinants on the same or on different antigens. Usually, the variability of a polyclonal antibody is located in the so-called variable regions of the polyclonal antibody, in particular in the CDR regions. In the present disclosure a mixture of two or more polyclonal antibodies (a polycomposition) is produced in one mixture from a polyclonal polycomposition cell line, which is produced from two or more parental polyclonal cell lines each expressing antibody molecules which are capable of binding to a distinct target, but it may also be a mixture of two or more polyclonal antibodies produced separately. A mixture of monoclonal antibodies providing the same antigen/epitope coverage as a polyclonal antibody described herein will be considered as an equivalent of a polyclonal antibody. When stating that a member of a polyclonal antibody binds to an antigen, it is herein meant to be binding with a binding constant below 100 nM, preferably below 10 nM, even more preferred below 1 nM.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g., mouse) with the desired specificity, affinity, and capability while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following. In certain embodiments, an anti-HIV Env antibody disclosed herein binds to HIV gp120 with a Kd of at least about 0.1 μM or less, at least about 0.01 μM or less, at least about 1 nM or less, or at least about 0.1 nM or less. In certain embodiments, an anti-HIV Env antibody disclosed herein binds to HIV gp120 with a Kd of at least about 0.01 μM or less. In certain embodiments, the HIV gp120 is BG505 gp120.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that immunospecifically bind to an antigen bind to the antigen with a Kd that is at least 2 logs, 2.5 logs, 3 logs, or 4 logs lower than the Kd when the molecules bind non-specifically to another antigen. In one example, the antibody may specifically bind to the BG505 SOSIP Env trimer. The antibody may bind to BG505 SOSIP trimer with a Kd at least 2 logs, 2.5 logs, 3 logs, or 4 logs lower than Kd of binding to other viral or non-viral polypeptides. An antibody that specifically binds to Env encompass, but are not limited to, antibodies that specifically bind to native Env, an isoform of Env, or a variant of Env (e.g., SOSIP) derived from an HIV isolate, for example, BG505. In one embodiment, the antibody specifically binds to BG505 Env. In one embodiment, the antibody or fusion polypeptide specifically binds to BG505 SOSIP.

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "broadly neutralizing antibody" or "bnAb," as used herein, with respect to HIV (e.g., HIV-1), refers to an antibody that recognizes HIV Env of more than one isolate or strain of HIV and inhibits or prevents receptor binding of target cells as evaluated in an in vitro neutralization assay. In one embodiment, a broadly neutralizing antibody inhibits infection of a susceptible target cell by HIV. In one embodiment, a broadly neutralizing antibody specifically binds an HIV Env and inhibits infection of a susceptible target cell (e.g., TZM-bl) by an HIV pseudovirus comprising an Env polypeptide. HIV pseudovirus neutralization assays have been disclosed in the art, for example, in Walker, L. M. et al., *Nature* 477, 466-470 (2011), Li M., et al., J. Virol. 79:10108-10125 (2005), each of which is incorporated herein by reference in its entirety for all purposes. In one embodiment, a broadly neutralizing antibody neutralizes 2, 3, 4, 5, 6, 7, 8, 9, or more HIV strains or pseudoviruses. In one embodiment, a broadly neutralizing antibody neutralizes 2, 3, 4, 5, 6, 7, 8, 9, or more HIV strains or pseudoviruses that belong to the same or different clades. In one embodiment, a broadly neutralizing antibody is capable of neutralizing HIV strains or pseudoviruses from at least two different clades. In one embodiment, a broadly neutralizing antibody is capable of neutralizing at least one clade B strain or pseudovirus and one clade C strain or pseudovirus. In one embodiment, a broadly neutralizing antibody is capable of neutralizing more than one clade B strain or pseudovirus and more than one clade C strain or pseudovirus. In one embodiment, a broadly neutralizing antibody is capable of neutralizing an HIV strain or pseudovirus from at least one, at least two, at least three, at least four, at least five, at least six, at least seven, at least eight, at least nine, at least ten, at least eleven, at least twelve, at least thirteen, at least fourteen, or all fifteen clades represented in the 116-member indicator virus panel. In one embodiment, a broadly neutralizing antibody is capable of neutralizing an HIV strain or pseudovirus from at least one, at least two, at least three, at least four, at least five, at least six, at least seven, at least eight, at least nine, at least ten, at least eleven, at least twelve, at least thirteen, at least fourteen, or all fifteen clades selected from the group consisting of clades A, A (T/F), AC, ACD, B, B (T/F), BC, C, C (T/F), CD, CRF01_AE, CRF01_AE (T/F), CRF02_AG, D, and G. In one embodiment, a broadly neutralizing antibody is capable of neutralizing an HIV strain or pseudovirus from at least one, at least two, at least three, at least four, at least five, at least six, at least seven, at least eight, at least nine, at least ten, or all eleven clades selected from the group consisting of clades A, AC, ACD, AE, AG, B, BC, C, CD, D, G.

In one embodiment, the breadth of neutralization is tested on an indicator virus panel comprising cross-clade HIV isolates. In one embodiment, the virus panel comprises the 8 cross-clade isolates of 6535, AC10_29, ZM197M.P07, Ce1176_A3, CNE52, Q461, BJ0X028000, and 6952.V1.c20. In one embodiment, the virus panel comprises the 30 cross-clade isolates of 6535.3, PVO.4, TRO.11, AC10.0.29, RHPA4259.7, WITO4160.33, 1006_11_C3_1601, 1012_11_TC21_3257, SC05_8C11_2344, Du172.17, ZM197M.PB7, Ce1176_A3, Ce704809221_1B3, Q461.e2, 928-28, T250-4, T251-18, BJ0X015000.11.5, BJ0X010000.06.2, BJ0X028000.10.3, X1193_c1, X2131_C1_B5, 6952.v1.c20, SC422661.8, 1056_10_TA11_1826, CNE52, T278-50, R1166.c01, BJ0X009000.02.4, and 3103.v3.c10. In one embodiment, the virus panel comprises the 116 cross-clade isolates of 6535.3, 62357_14_D3_4589, 6240_08_TA5_4622, 6244_13_B5_4576, 1006_11_C3_1601, 1012_11_TC21_3257, 1054_07_TC4_1499, 1056_10_TA11_1826, AC10.0.29, CAAN5342.A2, PVO.4, QH0692.42, REJ04541.67, RHPA4259.7, SC05_8C11_2344, SC422661.8, THR04156.18, TRJ04551.58, TRO.11, WEAU_d5_410_5017, WITO4160.33, CNE17, CNE19, CNE20, CNE21, CNE30, CNE52, CNE53, CNE58, 1394C9G1(Rev-), 246FC1G, 249MB10, 7030102001E5(Rev-), BF1266.431a, CAP210.2.00.E8, CAP45.2.00.G3, Ce0393_C3, Ce0682_E4, Ce1086_B2, Ce1172_H1, Ce1176_A3, Ce2010_F5, Ce2060_G9, Ce703010054_2A2, Ce704809221_1B3, Du156.12, Du172.17, Du422.1, HIV-0013095-2.11, HIV-001428-2.42, HIV-16055-2.3, HIV-16845-2.22, ZM109F.PB4, ZM135M.PL10a, ZM197M.PB7, ZM214M.PL15, ZM233M.PB6, ZM247v1 (Rev-), ZM249M.PL1, ZM53M.PB12, 3817.v2.c59, 6480.v4.c25, 6811.v7.c18, 6952.v1.c20, 89-F1_2_25, 191821_E6_1, 231965.c01, 3016.v5.c45, A07412M1.vrc12, P0402_C2_11, P1981_C5_3, X1193_C1, X1254_C3, X1632_S2_B10, X2088_C9, and X2131_C1_B5. In one embodiment, the virus panel comprises the 100 clade C isolates of Du422.1, ZM197M.PB7, ZM214M.PL15, ZM233M.PB6, ZM135M.PL10a, CAP45.2.00.G3, CAP244.2.00.D3, ZM215F.PB8, ZM106F.PB9, 0041.v3.c18, 0984.v2.c2, 6040.v4.c15, 6631.v3.c10, 933.v4.c4, 6980.v0.c31, 3426.v5.c17, Ce1172_H1, Ce703010131_1E2, Ce703010054_2A2, Ce0665_F2, Ce2052_G10, Ce704810053_2B7, CeCAP210_TA5, CeCAP200_B8a, CeCAP188_1_D1_14(Rev-), CeCAP177_1A3, ZM249M.PL1, 7060101641A7(Rev-), 235080_3G7env2(Rev-), 704010042, 705010185, 1245045, 19157834_V1, 2969249, 3514597, 20258279_V2, 20915593, 20927783, 20965238, 21197826_V1, 21283649, 2768732_C5_16, 18814602_H8_F3, 19252094_A5_G2, 19707346_E8_C6, 20104663_E11_D2, 20198102_E9_G1, 20286961_C1_H8, 20883229_C9_H6, 21203310_G7_C3, 21492713_B11_E3, 21502011_F12_E2, 21561324_D3_B5, 19314479_A2_5, 234-F1-16-57, 541-F1_A7_2, 569-F1_37_10, 556_F2_3_25, CAP69.1.12_TA7.1, CAP136.1.16_E6_1, CAP174.1.06_F3_1B, CAP225.1.06_A2_18, CAP266.2.00_E9_h6, TRP290.2.00_23_6, TRP307.2.00_24_1, TRP363.2.00_10_3, 722_G4_16, So431_C1_1, So405_T24_5, CT072_56_7, CT966_E1-7, CT140_140_B6, Ko426_T78_10, Ko459_T68_4, Ko870_C2_10, CA392_H2_6, CA146_H3_3, CA240_A5.5, 2865_A11.12, 3603_C11.13, 3312_D6.2, CAP304.2.00_F6.6, CAP308.2.00_E11.35, CAP323.2.00_B6.45, CAP330.2.00_F2.41, 20417927.07, 20358510.01, 1170887.08, B005018-8_F6.3, CT810_G4-7, CT184_D3.15, S0607_B6.9, Me178_G6.16, CAP291.2.00_H2.15, S0032_A2.8-1, CT565_C7.48, CH0505.w4.3, 6022.v7.c24, 6146.v7.c23, CH064.env. In one embodiment, a broadly neutralizing antibody is capable of neutralizing at least 4, 5, 6, 7 or 8 of the cross-clade HIV isolates in the 8-member indicator virus panel. In one embodiment, a broadly neutralizing antibody is capable of neutralizing at least 6 of the cross-clade HIV isolates in the 8-member indicator virus panel. In one embodiment, a broadly neutralizing antibody is capable of neutralizing at least 15, 20, 25, 26, 27, 28, 29, or 30 of the cross-clade HIV isolates in the 30-member indicator virus panel. In one embodiment, a broadly neutralizing antibody is capable of neutralizing at least 20 of the cross-clade HIV isolates in the 30-member indicator virus panel. In one embodiment, a broadly neutralizing antibody is capable of neutralizing at least 25 of the cross-clade HIV isolates in the 30-member indicator virus panel. In one embodiment, a broadly neutralizing antibody is capable of neutralizing at least 27 of the cross-clade HIV isolates in the 30-member indicator virus panel. In one embodiment, a broadly neutralizing antibody is capable of neutralizing 30 of the cross-clade HIV isolates in the 30-member indicator virus panel. In one embodiment, a broadly neutralizing antibody is capable of neutralizing at least about 50%, 60%, 70%, 80%, 90%, 95%, or 100% of cross-clade HIV isolates in the 116-member indicator virus panel. In one embodiment, a broadly neutralizing antibody is capable of neutralizing at least about 60% of cross-clade HIV isolates in the 116-member indicator virus panel. In one embodiment, a broadly neutralizing antibody is capable of neutralizing at least about 70% of cross-clade HIV isolates in the 116-member indicator virus panel. In one embodiment, a broadly neutralizing antibody is capable of neutralizing at least about 75% of cross-clade HIV isolates in the 116-member indicator virus panel. In one embodiment, a broadly neutralizing antibody is capable of neutralizing at least about 80% of cross-clade HIV isolates in the 116-member indicator virus panel. In one embodiment, a broadly neutralizing antibody is capable of neutralizing at least about 90% of cross-clade HIV isolates in the 116-member indicator virus panel. In one embodiment, a broadly neutralizing antibody is capable of neutralizing at least about 95% of cross-clade HIV isolates in the 116-member indicator virus panel. In one embodiment, a broadly neutralizing antibody is capable of neutralizing at least about 50%, 60%, 70%, 80%, 90%, 95%, or 100% of clade C HIV isolates in the 100-member indicator virus panel. In one embodiment, a broadly neutralizing antibody is capable of neutralizing at least about 20% of clade C HIV isolates in the 100-member indicator virus panel. In one embodiment, a broadly neutralizing antibody is capable of neutralizing at least about 30% of clade C HIV isolates in the 100-member indicator virus panel. In one embodiment, a broadly neutralizing antibody is capable of neutralizing at least about 35% of clade C HIV isolates in the 100-member indicator virus panel. In one embodiment, a broadly neutralizing antibody is capable of neutralizing at least about 40% of clade C HIV isolates in the 100-member indicator virus panel. In one embodiment, a broadly neutralizing antibody is capable of neutralizing at least about 45% of clade C HIV isolates in the 100-member indicator virus panel. In one embodiment, a broadly neutralizing antibody is capable of neutralizing at least about 50% of clade C HIV isolates in the 100-member indicator virus panel. In one embodiment, a broadly neutralizing antibody is capable of neutralizing at least about 60% of clade C HIV isolates in the 100-member indicator virus panel.

In one embodiment, the potency of neutralization by a broadly neutralizing antibody is expressed as the median $IC_{50}$ neutralization activity against a virus panel, for example the 8-virus panel, 30-virus panel, or 116-virus panel disclosed herein. In one embodiment, the potency of neutralization by a broadly neutralizing antibody is expressed as the median $IC_{50}$ neutralization activity against a virus panel, for example the 100-virus panel disclosed herein. In one embodiment, a broadly neutralizing antibody is capable of neutralizing at least about 4, 5, 6, 7, or 8 of the cross-clade HIV isolates in the 8-member indicator virus panel with a median $IC_{50}$ equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, a broadly neutralizing antibody is capable of neutralizing at least 6 of the cross-clade HIV isolates in the 8-member indicator virus panel with a median $IC_{50}$ equal to or less than 0.05 μg/ml. In one embodiment, a broadly neutralizing antibody is capable of neutralizing at least 15, 20, 25, 26, 27, 28, 29, or 30 of the cross-clade HIV isolates in the 30-member indicator virus panel with a median $IC_{50}$ equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, a broadly neutralizing antibody is capable of neutralizing at least 20 of the cross-clade HIV isolates in the 30-member indicator virus panel with a median $IC_{50}$ equal to or less than 0.05 μg/ml. In one embodiment, a broadly neutralizing antibody is capable of neutralizing at least 25 of the cross-clade HIV isolates in the 30-member indicator virus panel with a median $IC_{50}$ equal to or less than 0.05 μg/ml. In one embodiment, a broadly neutralizing antibody is capable of neutralizing at least 27 of the cross-clade HIV isolates in the 30-member indicator virus panel with a median $IC_{50}$ equal to or less than 0.05 g/ml. In one embodiment, a broadly neutralizing antibody is capable of neutralizing at least about 50%, 60%, 70%, 80%, 90%, 95%, or 100% of cross-clade HIV isolates in the 116-member indicator virus panel with a median $IC_{50}$ equal to or less than about 0.1 μg/ml, 0.07 μg/ml, 0.06 μg/ml, 0.05 g/ml, 0.025 μg/ml, 0.01 μg/ml or 0.005 μg/ml. In one embodiment, a broadly neutralizing antibody is capable of neutralizing at least about 70% of cross-clade HIV isolates in the 116-member indicator virus panel with a median $IC_{50}$ equal to or less than 0.05 μg/ml. In one embodiment, a broadly neutralizing antibody is capable of neutralizing at least about 75% of cross-clade HIV isolates in the 116-member indicator virus panel with a median $IC_{50}$ equal to or less than 0.05 μg/ml. In one embodiment, a broadly neutralizing antibody is capable of neutralizing at least about 80% of cross-clade HIV isolates in the 116-member indicator virus panel with a median $IC_{50}$ equal to or less than 0.05 μg/ml. In one embodiment, a broadly neutralizing antibody is capable of neutralizing at least about 20%, 20%, 35%, 40%, 45%, or 50% of clade C HIV isolates in the 100-member indicator virus panel with a median $IC_{50}$ equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, a broadly neutralizing antibody is capable of neutralizing at least about 50% of clade C HIV isolates in the 100-member indicator virus panel with a median $IC_{50}$ equal to or less than 0.05 μg/ml. In one embodiment, a broadly neutralizing antibody is capable of neutralizing at least about 40% of clade C HIV isolates in the 100-member indicator virus panel with a median $IC_{50}$ equal to or less than 0.05 μg/ml. In one embodiment, a broadly neutralizing antibody is capable of neutralizing at least about 40% of clade C HIV isolates in the 100-member indicator virus panel with a median $IC_{50}$ equal to or less than 0.01 μg/ml.

The term "$IC_{50}$" refers to the half maximal inhibitory concentration of an inhibitor, e.g., a broadly neutralizing antibody. For example, $IC_{50}$ is the concentration of an inhibitor, e.g., a broadly neutralizing antibody, where the response, e.g., infection by pseudovirus, is reduced by half.

The phrase "substantially similar," or "substantially the same", as used herein, denotes a sufficiently high degree of similarity between two numeric values (generally one associated with an antibody described herein and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides described herein are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.,* 87:2264-2268 (1990), as modified in Karlin et al., *Proc. Natl. Acad. Sci.,* 90:5873-5877 (1993), and incorporated into the NBLAST and XBLAST programs (Altschul et al., *Nucleic Acids Res.,* 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology,* 266:460-480 (1996)), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS,* 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as $100\times(Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman (*Advances in Applied Mathematics* 2: 482 489 (1981)) to find the best segment of homology between two sequences. When using Bestfit or any other sequence alignment program to determine whether a particular sequence is, for instance, 95% identical to a reference sequence described herein, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies described herein do not abrogate the binding of the polypeptide or antibody containing the amino acid sequence, to the antigen(s). Methods of identifying nucleotide and amino acid conservative substitutions which do not eliminate antigen binding are well-known in the art (see, e.g., Brummell et al., *Biochem.* 32: 1180-1187 (1993); Kobayashi et al., *Protein Eng.* 12(10):879-884 (1999); and Burks et al., *Proc. Natl. Acad. Sci. USA* 94:412-417 (1997)).

As used herein, the terms "treatment" or "therapy" (as well as different forms thereof, including curative or palliative) refer to treatment of an infected person. As used herein, the term "treating" includes alleviating or reducing at least one adverse or negative effect or symptom of a condition, disease or disorder. This condition, disease or disorder can be HIV infection.

Terms such as "treating" or "treatment" or "to treat" or "alleviating" or "to alleviate" refer to therapeutic measures that cure, slow down, lessen symptoms of, and/or halt progression of a diagnosed pathologic condition or disorder, such as HIV or AIDS. Thus, those in need of treatment include those already diagnosed with or suspected of having the disorder. In certain embodiments, a subject is successfully "treated" for the disorder according to the methods described herein if the patient shows one or more of the following: a reduction in the number of or complete absence of viral load; a reduction in the viral burden; inhibition of or an absence of the virus into peripheral organs; relief of one or more symptoms associated with the disorder; reduced morbidity and mortality; improvement in quality of life; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

As used herein, the terms "prevention" or "prophylaxis" refer to preventing a subject from becoming infected with, or reducing the risk of a subject from becoming infected with, or halting transmission of, or the reducing the risk of transmission of a virus. Prophylactic or preventative measures refer to measures that prevent and/or slow the development of a targeted pathological condition or disorder. Thus, those in need of prophylactic or preventative measures include those prone to have the disorder and those in whom the disorder is to be prevented. In one embodiment, prevention encompasses passive immunization of a subject in need thereof comprising administering an effective amount of an antibody disclosed herein.

As employed above and throughout the disclosure the term "effective amount" refers to an amount effective, at dosages, and for periods of time necessary, to achieve the desired result with respect to the treatment of the relevant disorder, condition, or side effect. An "effective amount" can be determined empirically and in a routine manner, in relation to the stated purpose. It will be appreciated that the effective amount of components of the present invention will vary from patient to patient not only with the particular vaccine, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

The term "therapeutically effective amount" refers to an amount of an antibody, recombinant virus, immunoconjugate, or other drug effective to "treat" a disease or disorder in a subject or mammal. To the extent an antibody can prevent growth and/or kill existing cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "subject," "individual," and "patient" are used interchangeably herein, and refer to an animal, for example a human, to whom treatment, including prophylactic treatment, with the antibody or pharmaceutical composition according to the present disclosure, is provided. In one embodiment, the subject, individual, or patient has been infected with HIV. In one embodiment, the subject, individual, or patient suffers from AIDS. In one embodiment, the subject, individual, or patient has been exposed to HIV. In one embodiment, the subject, individual, or patient is at risk of being exposed to HIV.

Administration "in combination with" one or more further therapeutic agents includes simultaneous (concurrent) or consecutive administration in any order.

The terms "pharmaceutically composition," "pharmaceutical formulation," "pharmaceutically acceptable formulation," or "pharmaceutically acceptable composition" all of which are used interchangeably, refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. "Pharmaceutically acceptable" or "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The term "antiretroviral therapy" or "ART," as used herein, refers to any of the therapies used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include, but are not limited to, lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc and raltegravir. ART drugs can also include antibodies that target HIV proteins or cellular proteins associated with disease progression. Also included are immune-based therapies, such as IL-2, IL-12, and alpha-epibromide. Each of these drugs can be administered alone or in combination with any other ART drug or any HIV-specific neutralizing antibody, such as a broadly neutralizing antibody, which is incorporated by reference herein in its entirety for all purposes.

The term "reservoir activator," as used herein, refers to an agent capable of activating a viral reservoir (e.g., an HIV reservoir). In one embodiment, a reservoir activator comprises a histone deacytelase (HDAC) inhibitor (e.g., romidepsin, vorinostat, and panobinostat), immunologic activator (e.g., cytokines and TLR agonists), or a dedicated small molecule drug.

The term "immunomodulator," as used herein, refers to an agent, such as an antibody or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Immunomodulators include, but are not limited to immune checkpoint inhibitors, for example, a PD-1, PD-L1, LAG-3, or TIGIT antagonist. In one embodiment, an immunomodulator used in the methods described herein comprises an anti-PD-1 antibody, anti-PD-L1 antibody, anti-LAG3 antibody, or an anti-TIGIT antibody. An immunomodulator can be administered in conjunction with (e.g., prior to, concurrently with, or subsequent to, or within the context of a treatment regimen that includes the administration of a broadly neutralizing antibody described herein.

As used in this specification and the appended claims, the singular forms "a," "an," and "the" include plural referents unless the content clearly dictates otherwise. Thus, for example, reference to "a cell" includes a combination of two or more cells, and the like.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein when referring to a measurable value such as an amount, a temporal duration, and the like, is meant to encompass variations of up to ±20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope described herein are approximations, the numerical values set forth in the specific examples are reported as precisely as possible. Any numerical value, however, inherently contain certain errors necessarily resulting from the standard deviation found in their respective testing measurements.

It is understood that wherever embodiments are described herein with the language "comprising," otherwise analogous embodiments described in terms of "consisting of" and/or "consisting essentially of" are also provided.

II. Engineered Anti-HIV Antibodies

In one aspect, provided herein is an engineered variant of the PGDM1400 antibody that specifically binds to HIV Env (e.g., BG505 SOSIP). In one embodiment, the antibody specifically binds to a well-ordered HIV Env trimer. The term "PGDM1400," as used herein, refers to an antibody comprising the VH of SEQ ID NO: 1 and VL of SEQ ID NO: 2, as disclosed, for example, in U.S. Pat. Appl. Pub. No. 20150361160, which is hereby incorporated by reference herein in its entirety.

In one aspect, provided herein is an engineered variant of the PGDM1400 antibody that is capable of neutralizing the BG505 HIV isolate.

In one aspect, provided herein is an engineered variant of the PGDM1400 antibody that is capable of neutralizing at least two cross-clade isolates of HIV. In one embodiment, the antibody is capable of neutralizing at least one clade B isolate and at least one clade C isolate.

In one embodiment, an antibody disclosed herein is a broadly neutralizing antibody.

In one embodiment, an antibody disclosed herein neutralizes 2, 3, 4, 5, 6, 7, 8, 9, or more HIV strains or pseudoviruses that belong to the same or different clades. In one embodiment, an antibody disclosed herein is capable of neutralizing HIV strains or pseudoviruses from at least two different clades. In one embodiment, an antibody disclosed herein is capable of neutralizing at least one clade B strain or pseudovirus and one clade C strain or pseudovirus. In one embodiment, an antibody disclosed herein is capable of neutralizing more than one clade B strain or pseudovirus and more than one clade C strain or pseudovirus. In one embodiment, an antibody disclosed herein is capable of neutralizing an HIV strain or pseudovirus from at least one, at least two, at least three, at least four, at least five, at least six, at least seven, at least eight, at least nine, at least ten, at least eleven, at least twelve, at least thirteen, at least fourteen, or fifteen clades represented in the 116-member indicator virus panel. In one embodiment, an antibody disclosed herein is capable of neutralizing an HIV strain or pseudovirus from at least one, at least two, at least three, at least four, at least five, at least six, at least seven, at least eight, at least nine, at least ten, at least eleven, at least twelve, at least thirteen, at least fourteen, or fifteen clades selected from the group consisting of clades A, A (T/F), AC, ACD, B, B (T/F), BC, C, C (T/F), CD, CRF01_AE, CRF01_AE (T/F), CRF02_AG, D, and G.

In one embodiments, an antibody disclosed herein has one or more improved properties. In one embodiment, an antibody disclosed herein has a higher binding affinity to HIV Env (e.g., BG505 SOSIP) than PGDM1400. In one embodiment, an antibody disclosed herein has improved median neutralization $IC_{50}$ potency (i.e., lower median $IC_{50}$) than PGDM1400. In one embodiment, an antibody disclosed herein has increased breadth of neutralization compared to PGDM1400.

In one embodiment, an antibody disclosed herein is a broadly neutralizing anti-HIV Env antibody. In one embodiment, an antibody disclosed herein specifically binds to HIV Env. In one embodiment, an antibody disclosed herein specifically binds to a well-ordered HIV Env trimer. In one embodiment, an antibody disclosed herein is a monoclonal antibody. In one embodiment, an antibody disclosed herein is an F(ab) or F(ab')2. In one embodiment, an antibody disclosed herein is a recombinant antibody, a chimeric antibody, an antibody fragment, a bispecific antibody, or a trispecific antibody.

In one embodiment, an antibody described herein comprises a VH, a VL, or a VH and VL comprising an amino acid sequence as shown in Table 1, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH, a VL, or a VH and VL comprising an amino acid sequence with at least about 80%, at least about 85%, at least about 90%, at least about 95%, at least about 97%, at least about 98%, at least about 99% or 100% identity to an amino acid sequence shown in Table 1, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP). In one embodiment, the antibody comprises a VH CDR1, VH CDR2, VH CDR3, VL CDR1, VL CDR2, and VL CDR3, wherein each of the VH CDR1, VH CDR2, VH CDR3, VL CDR1, VL CDR2, and VL CDR3 comprises an amino acid sequence as shown in Table 2.

In one embodiment, an antibody described herein comprises a VH CDR1, VH CDR2, VH CDR3, VL CDR1, VL CDR2, and VL CDR3, wherein the VH CDR3 is the VH CDR3 of a VH shown in Table 1 other than the PGDM1400 VH CDR3. In one embodiment, an antibody described herein comprises a VH CDR1, VH CDR2, VH CDR3, VL CDR1, VL CDR2, and VL CDR3, wherein the VH CDR3 comprises an amino acid sequence shown in Table 2 other than SEQ ID NO: 29. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein one, two, three, four, five or six of the VH CDR1, VH CDR2, VH CDR3, VL CDR1, VL CDR2, and VL CDR3 comprise an amino acid sequence shown in Table 2, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein one, two, three, four, five or six of the VH CDR1, VH CDR2, VH CDR3, VL CDR1, VL CDR2, and VL CDR3 comprise an amino acid sequence with at least about 80%, at least about 85%, at least about 90%, at least about 95%, at least about 97%, at least about 98%, at least about 99% or 100% identity to an amino acid sequence shown in Table 2, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein one, two, three, four, five or six of the VH CDR1, VH CDR2, VH CDR3, VL CDR1, VL CDR2, and VL CDR3 comprise an amino acid sequence shown in Table 2 comprising 0, 1, 2, 3, 4, or 5 substitutions, deletions, or insertions, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR3 comprising an amino acid sequence as shown in Table 2, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR3 comprising an amino acid sequence with at least about 80%, at least about 85%, at least about 90%, at least about 95%, at least about 97%, at least about 98%, at least about 99% or 100% identity to an amino acid sequence shown in Table 2, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR3 comprising an amino acid sequence as shown in Table 2 comprising 0, 1, 2, 3, 4, or 5 substitutions, deletions, or insertions, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein each of the VH CDR1, VH CDR2, VH CDR3, VL CDR1, VL CDR2, and VL CDR3 comprises an amino acid sequence as shown in Table 2, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein each of the VH CDR1, VH CDR2, VH CDR3, VL CDR1, VL CDR2, and VL CDR3 comprises an amino acid sequence with at least about 80%, at least about 85%, at least about 90%, at least about 95%, at least about 97%, at least about 98%, at least about 99% or 100% identity to an amino acid sequence shown in Table 2, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein each of the VH CDR1, VH CDR2, VH CDR3, VL CDR1, VL CDR2, and VL CDR3 comprises an amino acid sequence as shown in Table 2 comprising 0, 1, 2, 3, 4, or 5 substitutions, deletions, or insertions, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein further comprises a VH FR1, VH FR2, VH FR3, VH FR4, VL FR1, VL FR2, VL FR3, and VL FR4, wherein one, two, three, four, five, six, seven or eight of the VH FR1, VH FR2, VH FR3, VH FR4, VL FR1, VL FR2, VL FR3, and VL FR4 comprise an amino acid sequence shown in Table 3.

In one embodiment, an antibody described herein further comprises a VH FR1, VH FR2, VH FR3, VH FR4, VL FR1, VL FR2, VL FR3, and VL FR4, wherein one, two, three, four, five, six, seven or eight of the VH FR1, VH FR2, VH FR3, VH FR4, VL FR1, VL FR2, VL FR3, and VL FR4 comprise an amino acid sequence with at least about 80%, at least about 85%, at least about 90%, at least about 95%, at least about 97%, at least about 98%, at least about 99% or 100% identity to an amino acid sequence shown in Table 3.

In one embodiment, an antibody described herein further comprises a VH FR1, VH FR2, VH FR3, VH FR4, VL FR1, VL FR2, VL FR3, and VL FR4, wherein one, two, three, four, five, six, seven or eight of the VH FR1, VH FR2, VH FR3, VH FR4, VL FR1, VL FR2, VL FR3, and VL FR4 comprise an amino acid sequence shown in Table 3 comprising 0, 1, 2, 3, 4, or 5 substitutions, deletions, or insertions.

In one embodiment, an antibody described herein further comprises a VH FR1, VH FR2, VH FR3, VH FR4, VL FR1, VL FR2, VL FR3, and VL FR4, wherein each of the VH FR1, VH FR2, VH FR3, VH FR4, VL FR1, VL FR2, VL FR3, and VL FR4 comprises an amino acid sequence as shown in Table 3.

In one embodiment, an antibody described herein further comprises a VH FR1, VH FR2, VH FR3, VH FR4, VL FR1, VL FR2, VL FR3, and VL FR4, wherein each of the VH FR1, VH FR2, VH FR3, VH FR4, VL FR1, VL FR2, VL FR3, and VL FR4 comprises an amino acid sequence with at least about 80%, at least about 85%, at least about 90%, at least about 95%, at least about 97%, at least about 98%, at least about 99% or 100% identity to an amino acid sequence shown in Table 3.

In one embodiment, an antibody described herein further comprises a VH FR1, VH FR2, VH FR3, VH FR4, VL FR1, VL FR2, VL FR3, and VL FR4, wherein each of the VH FR1, VH FR2, VH FR3, VH FR4, VL FR1, VL FR2, VL FR3, and VL FR4 comprises an amino acid sequence as shown in Table 3 comprising 0, 1, 2, 3, 4, or 5 substitutions, deletions, or insertions.

In one embodiment, an antibody described herein comprises a heavy chain, light chain, or a heavy and light chain comprising an amino acid sequence as shown in Table 2, wherein the antibody is not PGDM1400. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a heavy chain, light chain, or a heavy and light chain comprising an amino acid sequence with at least about 80%, at least about 85%, at least about 90%, at least about 95%, at least about 97%, at least about 98%, at least about 99% or 100% identity to an amino acid sequence shown in Table 1, wherein the antibody is not PGDM1400. In one embodiment, the antibody is capable of neutralizing BG505. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP). In one embodiment, the antibody comprises a VH CDR1, VH CDR2, VH CDR3, VL CDR1, VL CDR2, and VL CDR3, wherein each of the VH CDR1, VH CDR2, VH CDR3, VL CDR1, VL CDR2, and VL CDR3 comprises an amino acid sequence as shown in Table 2.

Also provided herein are polypeptides that comprise an amino acid sequence having at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence, or is identical to the sequences listed in Tables 1, 2, 3, and 4, wherein the polypeptide is not a PGDM1400 polypeptide.

TABLE 1

| Variable heavy chain (VH) and light chain (VL) domains. | |
|---|---|
| pGDM1400 VH | QVHLTQSGPEVRKPGTSVKVSCKAPGNTLKTYDLHWVRSVPGQGLQ WMGWISHEGDKKVIVERFKAKVTIDWDRSTNTAYLQLSGLTSGDTAV YYCAKGSKHRLRDYALYDDDGALNWAVDVDYLSNLEFWGQGTAVT VSS (SEQ ID NO: 1) |

TABLE 1-continued

| Variable heavy chain (VH) and light chain (VL) domains. | |
|---|---|
| pGDM1400 VL | DFVLTQSPHSLSVTPGESASISCKSSHSLIHGDRNNYLAWYVQKPGRSPQLLIYLASSRASGVPDRFSGSGSDKDFTLKISRVETEDVGTYYCMQGRESPWTFGQGTKVDIK (SEQ ID NO: 2) |
| ePGDM-A VH | QVQLVQSGAEVRKPGASVKVSCKNPGNTLTTYDLHWVRQVPGQGLQWMGWISHEGDKKVIVERFKAKVDIDWDRSTNTAYLQLSGLTSEDTAVYYCAKGSKHRLRDYALYDEDGALEWAVDVDYLANLEFWGQGTAVTVSS (SEQ ID NO: 3) |
| ePGDM-B VH | QAQLVQSGAEVRKPGASVKVSCKNPGNTLTTYDLHWVRSVPGQGLEWMGWISHEGDKKVIAERFKAKVDIDWDRSTNTAYLGLSGLTSEDTAVYYCAKGSKHRLRDYALYDEDGALEWAEDVDYLANLEFWGQGTAVTVSS (SEQ ID NO: 4) |
| ePGDM-C VH | QVQLVQSGPEVRKPGASVKVSCKNPGNTLTTYDLHWVRQVPGQGLQWMGWISHEGDKKVIVEKFKAKVDIDWDRSTNTAYLQLSGLTSEDTAVYYCAKGSKHRLRDYALYDEDGALEWAEDVDYLANLEFWGQGTAVTVSS (SEQ ID NO: 5) |
| ePGDM-D VH | QVQLVQSGPEVRKPGTSVKVSCKNPGNTLTTYDLHWVRQVPGQGLQWMGWISHEGDKKVIVERFKAKVDIDWDRSTNTAYLGLSGLTSEDTAVYYCAKGSKHRLRDYALYDDDGALEWAEDVDYLANLEFWGQGTAVTVSS (SEQ ID NO: 6) |
| ePGDM-E VH | QAQLVQSGAEVRKPGTSVKVSCKNPGNTLTTYDLHWVRSVPGQGLEWMGWISHEGDKKEIVERFKAKVDIDWDRSTNTAYLQLSGLTSEDTAVYYCAKGSKHRLRDYALYDEDGALNWAVDVDYLANLEFWGQGTAVTVSS (SEQ ID NO: 7) |
| ePGDM-F VH | QVQLVQSGPEVRKPGASVKVSCKNPGNTLTTYDLHWVRSVPGQGLQWMGWISHEGDKKVIVERFKAKVDIDWDRSTNTAYLQLSGLTSEDTAVYYCAKGSKHRLRDYALYDEDGALEYAEDVDYLANLEFWGQGTAVTVSS (SEQ ID NO: 8) |
| ePGDM-G VH | QAQLVQSGPEVRKPGTSVKVSCKNPGNTLTTYDLHWVRQVPGQGLQWMGWISHEGDKKVIVERFKAKVTIDWDRSTNTAYLQLSGLTSEDTAVYYCAKGSKHRLRDYALYDEDGALNWAVDVDYLANLEFWGQGTAVTVSS (SEQ ID NO: 9) |
| ePGDM-H VH | QAQLVQSGAEVRKPGTSVKVSCKNPGNTLTTYDLHWVRQVPGQGLQWMGWISHEGDKKVIVERFQGRVDIDWDRSTNTAYLQLSGLTSEDTAVYYCAKGSKHRLRDYALYDEDGALNWAVDVDYLANLEFWGQGTAVTVSS (SEQ ID NO: 10) |
| ePGDM-I VH | QAQLVQSGPEVRKPGTSVKVSCKNPGNTLTTYDLHWVRQVPGQGLEWMGWISHEGDQKVIVEKFKAKVDIDWDRSTNTAYLQLSGLTSEDTAVYYCAKGSKHRLRDYALYDEDGALEWAVDVDYLANLEFWGQGTAVTVSS (SEQ ID NO: 11) |
| ePGDM-J VH | QVQLVQSGPEVRKPGTSVKVSCKNPGNTLTTYDLHWVRQVPGQGLQWMGWISHEGDQKVIVERFKAKVDIDWDRSTNTAYLQLSGLTSEDTAVYYCAKGSKHRLRDYALYDEDGALNWAVDVDYLANLEFWGQGTAVTVSS (SEQ ID NO: 12) |
| ePGDM-A VL | DIVLTQSPLSLSVTPGESASISCKSDQSLQHGDRNNYLAWYVQKPGKSPQLLIDLASERASGVPDRFSGSGSEKDFTLKISRVEAEDVGTYYCMQGRESPWTFGQGTKVDIK (SEQ ID NO: 13) |
| ePGDM-B VL | DIVLTQSPLSLSVTPGESASISCKSSQSLQHGDRNNYLAWYLQKPGKSPQLLLDLGSDRASGVPDRFSGSGSRKDFTLSISRVEAEDVGTYYCMQGRESPWTFGQGTKVDIK (SEQ ID NO: 14) |
| ePGDM-C VL | DIVLTQSPHSLSVTPGEPASISCKSSQSLLHGDRNNYLAWYVQKPGRSPQLLLDLASDRASGVPDRFSGSGSEKDFTLKIDRVETEDVGTYYCMQGRESPWTFGQGTKVDIK (SEQ ID NO: 15) |
| ePGDM-D VL | DFVLTQSPLSLSVTPGESASISCKSSQSLQHGDRNNYLAWYVQKPGQSPQLLIDLASDRASGVPDRFSGSGSEKDFTLSIDRVEAEDVGTYYCMQGRESPWTFGQGTKVDIK (SEQ ID NO: 16) |
| ePGDM-E VL | DFVLTQSPLSLSVTPGESASISCKSDHSLQHGDRNNYLAWYVQKPGRSPQLLIDLASERASGVPDRFSGSGSRKDFTLKIDRVEAEDVGTYYCMQGRESPWTFGQGTKVDIK (SEQ ID NO: 17) |
| ePGDM-F VL | DIVLTQSPLSLSVTPGESASISCKSDHSLQHGDRNNYLAWYVQKPGKSPQLLIDLASDRASGVPDRFSGSGSEKDFTLSISRVETEDVGTYYCMQGRESPWTFGQGTKVDIK (SEQ ID NO: 18) |

TABLE 1-continued

| Variable heavy chain (VH) and light chain (VL) domains. | |
|---|---|
| ePGDM-G VL | DIVLTQSPLSLSVTPGESASISCKSSQSLQHGDRNNYLAWYVQKPGRSP QLLLDLASDRASGVPDRFSGSGSEKDFTLKIDRVEAEDVGTYYCMQGR ESPWTFGQGTKVDIK (SEQ ID NO: 19) |
| ePGDM-H VL | DIVLTQSPLSLSVTPGESASISCKSSHSLQHGDRNNYLAWYVQKPGQSP QLLIDLGSDRASGVPDRFSGSGSEKDFTLKIDRVEAEDVGTYYCMQGR ESPWTFGQGTKVDIK (SEQ ID NO: 20) |
| ePGDM-I VL | DIVLTQSPLSLSVTPGESASISCKSSQSLIHGDRNNYLAWYVQKPGRSP QLLIDLASERASGVPDRFSGSGSRKDFTLKISRVETEDVGTYYCMQGRE SPWTFGQGTKVDIK (SEQ ID NO: 21) |
| ePGDM-J VL | DIVLTQSPLSLSVTPGEPASISCKSDQSLQHGDRNNYLAWYVQKPGRSP QLLIDLASDRASGVPDRFSGSGSEKDFTLSISRVEAEDVGTYYCMQGRE SPWTFGQGTKVDIK (SEQ ID NO: 22) |
| ePGDM-K VL | DIVLTQSPLSLSVTPGESASISCKSDQSLQHGDRNNYLAWYVQKPGRSP QLLIDLASDRASGVPDRFSGSGSEKDFTLSISRVETEDVGTYYCMQGRE SPWTFGQGTKVDIK (SEQ ID NO: 23) |
| ePGDM-L VL | DIVLTQSPLSLSVTPGEPASISCKSSQSLQHGDRNNYLAWYVQKPGQSP QLLIDLASDRASGVPDRFSGSGSEKDFTLSISRVETEDVGTYYCMQGRE SPWTFGQGTKVDIK (SEQ ID NO: 24) |
| ePGDM-M VL | DIVLTQSPLSLSVTPGESASISCKSSHSLQHGDRNNYLAWYVQKPGRSP QLLLDLASERASGVPDRFSGSGSEKDFTLKISRVETEDVGTYYCMQGR ESPWTFGQGTKVDIK (SEQ ID NO: 25) |
| ePGDM-N VL | DIVLTQSPLSLSVTPGEPASISCKSSQSLIHGDRNNYLAWYVQKPGKSP QLLIDLASDRASGVPDRFSGSGSEKDFTLSISRVEAEDVGTYYCMQGRE SPWTFGQGTKVDIK (SEQ ID NO: 26) |
| ePGDM-O VL | DIVLTQSPLSLSVTPGEPASISCKSSHSLQHGDRNNYLAWYVQKPGRSP QLLIDLASDRASGVPDRFSGSGSEKDFTLSISRVEAEDVGTYYCMQGRE SPWTFGQGTKVDIK (SEQ ID NO: 27) |
| ePGDM-P VL | DIVLTQSPLSLSVTPGESASISCKSSHSLQHGDRNNYLAWYLQKPGQSP QLLIDLASDRASGVPDRFSGSGSEKDFTLKIDRVETEDVGTYYCMQGR ESPWTFGQGTKVDIK (SEQ ID NO: 28) |

TABLE 2

VH and VL CDR sequences. The CDRs have been determined according to Kabat.

| | CDR1 | CDR2 | CDR3 |
|---|---|---|---|
| pGDM1400 VH | GNTLKTYD (SEQ ID NO: 36) | ISHEGDKK (SEQ ID NO: 38) | CAKGSKHRLRDYALYDDDGA LNWAVDVDYLSNLEFW (SEQ ID NO:29) |
| pGDM1400 VL | HSLIHGDRNNY (SEQ ID NO: 40) | LAS (SEQ ID NO: 45) | CMQGRESPWTF (SEQ ID NO: 30) |
| ePGDM-A VH | GNTLTTYD (SEQ ID NO: 37) | ISHEGDKK (SEQ ID NO: 38) | CAKGSKHRLRDYALYDEDGA LEWAVDVDYLANLEFW (SEQ ID NO: 31) |
| ePGDM-B VH | GNTLTTYD (SEQ ID NO: 37) | ISHEGDKK (SEQ ID NO: 38) | CAKGSKHRLRDYALYDEDGA LEWAEDVDYLANLEFW (SEQ ID NO: 32) |
| ePGDM-C VH | GNTLTTYD (SEQ ID NO: 37) | ISHEGDKK (SEQ ID NO: 38) | CAKGSKHRLRDYALYDEDGA LEWAEDVDYLANLEFW (SEQ ID NO: 32) |
| ePGDM-D VH | GNTLTTYD (SEQ ID NO: 37) | ISHEGDKK (SEQ ID NO: 38) | CAKGSKHRLRDYALYDDDGA LEWAEDVDYLANLEFW (SEQ ID NO: 33) |
| ePGDM-E VH | GNTLTTYD (SEQ ID NO: 37) | ISHEGDKK (SEQ ID NO: 38) | CAKGSKHRLRDYALYDEDGA LNWAVDVDYLANLEFW (SEQ ID NO: 34) |

TABLE 2-continued

VH and VL CDR sequences. The CDRs have been determined according to Kabat.

| | CDR1 | CDR2 | CDR3 |
|---|---|---|---|
| ePGDM-F VH | GNTLTTYD (SEQ ID NO: 37) | ISHEGDKK (SEQ ID NO: 38) | CAKGSKHRLRDYALYDEDGALEYAEDVDYLANLEFW (SEQ ID NO: 35) |
| ePGDM-G VH | GNTLTTYD (SEQ ID NO: 37) | ISHEGDKK (SEQ ID NO: 38) | CAKGSKHRLRDYALYDEDGALNWAVDVDYLANLEFW (SEQ ID NO: 34) |
| ePGDM-H VH | GNTLTTYD (SEQ ID NO: 37) | ISHEGDKK (SEQ ID NO: 38) | CAKGSKHRLRDYALYDEDGALNWAVDVDYLANLEFW (SEQ ID NO: 34) |
| ePGDM-I VH | GNTLTTYD (SEQ ID NO: 37) | ISHEGDQK (SEQ ID NO: 39) | CAKGSKHRLRDYALYDEDGALEWAVDVDYLANLEFW (SEQ ID NO: 31) |
| ePGDM-J VH | GNTLTTYD (SEQ ID NO: 37) | ISHEGDQK (SEQ ID NO: 39) | CAKGSKHRLRDYALYDEDGALNWAVDVDYLANLEFW (SEQ ID NO: 34) |
| ePGDM-A VL | QSLQHGDRNNY (SEQ ID NO: 41) | LAS (SEQ ID NO: 45) | CMQGRESPWTF (SEQ ID NO: 30) |
| ePGDM-B VL | QSLQHGDRNNY (SEQ ID NO: 41) | LGS (SEQ ID NO: 46) | CMQGRESPWTF (SEQ ID NO: 30) |
| ePGDM-C VL | QSLLHGDRNNY (SEQ ID NO: 42) | LAS (SEQ ID NO: 45) | CMQGRESPWTF (SEQ ID NO: 30) |
| ePGDM-D VL | QSLQHGDRNNY (SEQ ID NO: 41) | LAS (SEQ ID NO: 45) | CMQGRESPWTF (SEQ ID NO: 30) |
| ePGDM-E VL | HSLQHGDRNNY (SEQ ID NO: 43) | LAS (SEQ ID NO: 45) | CMQGRESPWTF (SEQ ID NO: 30) |
| ePGDM-F VL | HSLQHGDRNNY (SEQ ID NO: 43) | LAS (SEQ ID NO: 45) | CMQGRESPWTF (SEQ ID NO: 30) |
| ePGDM-G VL | QSLQHGDRNNY (SEQ ID NO: 41) | LAS (SEQ ID NO: 45) | CMQGRESPWTF (SEQ ID NO: 30) |
| ePGDM-H VL | HSLQHGDRNNY (SEQ ID NO: 43) | LGS (SEQ ID NO: 46) | CMQGRESPWTF (SEQ ID NO: 30) |
| ePGDM-I VL | QSLIHGDRNNY (SEQ ID NO: 44) | LAS (SEQ ID NO: 45) | CMQGRESPWTF (SEQ ID NO: 30) |
| ePGDM-J VL | QSLQHGDRNNY (SEQ ID NO: 41) | LAS (SEQ ID NO: 45) | CMQGRESPWTF (SEQ ID NO: 30) |
| ePGDM-K VL | QSLQHGDRNNY (SEQ ID NO: 41) | LAS (SEQ ID NO: 45) | CMQGRESPWTF (SEQ ID NO: 30) |
| ePGDM-L VL | QSLQHGDRNNY (SEQ ID NO: 41) | LAS (SEQ ID NO: 45) | CMQGRESPWTF (SEQ ID NO: 30) |
| ePGDM-M VL | HSLQHGDRNNY (SEQ ID NO: 43) | LAS (SEQ ID NO: 45) | CMQGRESPWTF (SEQ ID NO: 30) |
| ePGDM-N VL | QSLIHGDRNNY (SEQ ID NO: 44) | LAS (SEQ ID NO: 45) | CMQGRESPWTF (SEQ ID NO: 30) |

TABLE 2-continued

VH and VL CDR sequences. The CDRs have been determined according to Kabat.

| | CDR1 | CDR2 | CDR3 |
|---|---|---|---|
| ePGDM-O VL | HSLQHGDRNNY (SEQ ID NO: 43) | LAS (SEQ ID NO: 45) | CMQGRESPWTF (SEQ ID NO: 30) |
| | CDR1 | CDR2 | CDR3 |
| ePGDM-P VL | HSLQHGDRNNY (SEQ ID NO: 43) | LAS (SEQ ID NO: 45) | CMQGRESPWTF (SEQ ID NO: 30) |

TABLE 3

VH and VL Framework (FR) sequences. The FRs have been determined according to Kabat.

| | FR1 | FR2 | FR3 | FR4 |
|---|---|---|---|---|
| pGDM1400 VH | QVHLTQSGPEVRKPGTSVKVSCKAP (SEQ ID NO: 47) | LHWVRSVPGQGLQWMGW (SEQ ID NO: 54) | VIVERFKAKVTIDWDRSTNTAYLQLSGLTSGDTAVYY (SEQ ID NO: 58) | GQGTAVTVSS (SEQ ID NO: 66) |
| pGDM1400 VL | DFVLTQSPHSLSVTPGESASISCKSS (SEQ ID NO: 67) | LAWYVQKPGRSPQLLIY (SEQ ID NO: 75) | SRASGVPDRFSGSGSDKDFTLKISRVETEDVGTYY (SEQ ID NO: 82) | GQGTKVDIK (SEQ ID NO: 93) |
| ePGDM-A VH | QVQLVQSGAEVRKPGASVKVSCKNP (SEQ ID NO: 48) | LHWVRQVPGQGLQWMGW (SEQ ID NO: 55) | VIVERFKAKVDIDWDRSTNTAYLQLSGLTSEDTAVYY (SEQ ID NO: 59) | GQGTAVTVSS (SEQ ID NO: 66) |
| ePGDM-B VH | QAQLVQSGAEVRKPGASVKVSCKNP (SEQ ID NO: 49) | LHWVRSVPGQGLEWMGW (SEQ ID NO: 56) | VIAERFKAKVDIDWDRSTNTAYLGLSGLTSEDTAVYY (SEQ ID NO: 60) | GQGTAVTVSS (SEQ ID NO: 66) |
| ePGDM-C VH | QVQLVQSGPEVRKPGASVKVSCKNP (SEQ ID NO: 50) | LHWVRQVPGQGLQWMGW (SEQ ID NO: 55) | VIVEKFKAKVDIDWDRSTNTAYLQLSGLTSEDTAVYY (SEQ ID NO: 61) | GQGTAVTVSS (SEQ ID NO: 66) |
| ePGDM-D VH | QVQLVQSGPEVRKPGTSVKVSCKNP (SEQ ID NO: 51) | LHWVRQVPGQGLQWMGW (SEQ ID NO: 55) | VIVERFKAKVDIDWDRSTNTAYLGLSGLTSEDTAVYY (SEQ ID NO: 62) | GQGTAVTVSS (SEQ ID NO: 66) |
| ePGDM-E VH | QAQLVQSGAEVRKPGTSVKVSCKNP (SEQ ID NO: 52) | LHWVRSVPGQGLEWMGW (SEQ ID NO: 56) | EIVERFKAKVDIDWDRSTNTAYLQLSGLTSEDTAVYY (SEQ ID NO: 63) | GQGTAVTVSS (SEQ ID NO: 66) |
| ePGDM-F VH | QVQLVQSGPEVRKPGASVKVSCKNP (SEQ ID NO: 50) | LHWVRSVPGQGLQWMGW (SEQ ID NO: 54) | VIVERFKAKVDIDWDRSTNTAYLQLSGLTSEDTAVYY (SEQ ID NO: 59) | GQGTAVTVSS (SEQ ID NO: 66) |
| ePGDM-G VH | QAQLVQSGPEVRKPGTSVKVSCKNP (SEQ ID NO: 53) | LHWVRQVPGQGLQWMGW (SEQ ID NO: 55) | VIVERFKAKVTIDWDRSTNTAYLQLSGLTSEDTAVYY (SEQ ID NO: 64) | GQGTAVTVSS (SEQ ID NO: 66) |

TABLE 3-continued

VH and VL Framework (FR) sequences. The FRs have been determined according to Kabat.

| | FR1 | FR2 | FR3 | FR4 |
|---|---|---|---|---|
| ePGDM-H VH | QAQLVQSGAEV RKPGTSVKVSC KNP (SEQ ID NO: 52) | LHWVRQVPGQG LQWMGW (SEQ ID NO: 55) | VIVERFQGRVD IDWDRSTNTAY LQLSGLTSEDT AVYY (SEQ ID NO: 65) | GQGTAVTVSS (SEQ ID NO: 66) |
| ePGDM-I VH | QAQLVQSGPEV RKPGTSVKVSC KNP (SEQ ID NO: 53) | LHWVRQVPGQG LEWMGW (SEQ ID NO: 57) | VIVEKFKAKVD IDWDRSTNTAY LQLSGLTSEDT AVYY (SEQ ID NO: 61) | GQGTAVTVSS (SEQ ID NO: 66) |
| ePGDM-J VH | QVQLVQSGPEV RKPGTSVKVSC KNP (SEQ ID NO: 51) | LHWVRQVPGQG LQWMGW (SEQ ID NO: 55) | VIVERFKAKVD IDWDRSTNTAY LQLSGLTSEDT AVYY (SEQ ID NO: 59) | GQGTAVTVSS (SEQ ID NO: 66) |
| ePGDM-A VL | DIVLTQSPLSL SVTPGESASIS CKSD (SEQ ID NO: 68) | LAWYVQKPGKS PQLLID (SEQ ID NO: 76) | ERASGVPDRFS GSGSEKDFTLK ISRVEAEDVGT YY (SEQ ID NO: 83) | GQGTKVDIK (SEQ ID NO: 93) |
| ePGDM-B VL | DIVLTQSPLSL SVTPGESASIS CKSS (SEQ ID NO: 69) | LAWYLQKPGKS PQLLLD (SEQ ID NO: 77) | DRASGVPDRFS GSGSRKDFTLS ISRVEAEDVGT YY (SEQ ID NO: 84) | GQGTKVDIK (SEQ ID NO: 93) |
| ePGDM-C VL | DIVLTQSPHSL SVTPGEPASIS CKSS (SEQ ID NO: 70) | LAWYVQKPGRS PQLLLD (SEQ ID NO: 78) | DRASGVPDRFS GSGSEKDFTLK IDRVETEDVGT YY (SEQ ID NO: 85) | GQGTKVDIK (SEQ ID NO: 93) |
| ePGDM-D VL | DFVLTQSPLSL SVTPGESASIS CKSS (SEQ I DNO: 71) | LAWYVQKPGQS PQLLID (SEQ ID NO: 79) | DRASGVPDRFS GSGSEKDFTLS IDRVEAEDVGT YY (SEQ ID NO: 86) | GQGTKVDIK (SEQ ID NO: 93) |
| ePGDM-E VL | DFVLTQSPLSL SVTPGESASIS CKSD (SEQ ID NO: 72) | LAWYVQKPGRS PQLLID (SEQ ID NO: 80) | ERASGVPDRFS GSGSRKDFTLK IDRVEAEDVGT YY (SEQ ID NO: 87) | GQGTKVDIK (SEQ ID NO: 93) |
| ePGDM-F VL | DIVLTQSPLSL SVTPGESASIS CKSD (SEQ ID NO: 68) | LAWYVQKPGKS PQLLID (SEQ ID NO: 76) | DRASGVPDRFS GSGSEKDFTLS ISRVETEDVGT YY (SEQ ID NO: 88) | GQGTKVDIK (SEQ ID NO: 93) |
| ePGDM-G VL | DIVLTQSPLSL SVTPGESASIS CKSS (SEQ ID NO: 69) | LAWYVQKPGRS PQLLLD (SEQ ID NO: 78) | DRASGVPDRFS GSGSEKDFTLK IDRVEAEDVGT YY (SEQ ID NO: 89) | GQGTKVDIK (SEQ ID NO: 93) |
| ePGDM-H VL | DIVLTQSPLSL SVTPGESASIS CKSS (SEQ ID NO: 69) | LAWYVQKPGQS PQLLID (SEQ ID NO: 79) | DRASGVPDRFS GSGSEKDFTLK IDRVEAEDVGT YY (SEQ ID NO: 89) | GQGTKVDIK (SEQ ID NO: 93) |
| ePGDM-I VL | DIVLTQSPLSL SVTPGESASIS CKSS (SEQ ID NO: 69) | LAWYVQKPGRS PQLLID (SEQ ID NO: 80) | ERASGVPDRFS GSGSRKDFTLK ISRVETEDVGT YY (SEQ ID NO: 90) | GQGTKVDIK (SEQ ID NO: 93) |

TABLE 3-continued

VH and VL Framework (FR) sequences. The FRs have been determined according to Kabat.

| | FR1 | FR2 | FR3 | FR4 |
|---|---|---|---|---|
| ePGDM-J VL | DIVLTQSPLSL SVTPGEPASIS CKSD (SEQ ID NO: 73) | LAWYVQKPGRS PQLLID (SEQ ID NO: 80) | DRASGVPDRFS GSGSEKDFTLS ISRVEAEDVGT YY (SEQ ID NO: 91) | GQGTKVDIK (SEQ ID NO: 93) |
| ePGDM-K VL | DIVLTQSPLSL SVTPGESASIS CKSD (SEQ ID NO: 68) | LAWYVQKPGRS PQLLID (SEQ ID NO: 80) | DRASGVPDRFS GSGSEKDFTLS ISRVETEDVGT YY (SEQ ID NO: 88) | GQGTKVDIK (SEQ ID NO: 93) |
| ePGDM-L VL | DIVLTQSPLSL SVTPGEPASIS CKSS (SEQ ID NO: 74) | LAWYVQKPGQS PQLLID (SEQ ID NO: 79) | DRASGVPDRFS GSGSEKDFTLS ISRVETEDVGT YY (SEQ ID NO: 88) | GQGTKVDIK (SEQ ID NO: 93) |
| ePGDM-M VL | DIVLTQSPLSL SVTPGESASIS CKSS (SEQ ID NO: 69) | LAWYVQKPGRS PQLLLD (SEQ ID NO: 78) | ERASGVPDRFS GSGSEKDFTLK ISRVETEDVGT YY (SEQ ID NO: 92) | GQGTKVDIK (SEQ ID NO: 93) |
| ePGDM-N VL | DIVLTQSPLSL SVTPGEPASIS CKSS (SEQ ID NO: 74) | LAWYVQKPGKS PQLLID (SEQ ID NO: 76) | DRASGVPDRFS GSGSEKDFTLS ISRVEAEDVGT YY (SEQ ID NO: 91) | GQGTKVDIK (SEQ ID NO: 93) |
| ePGDM-O VL | DIVLTQSPLSL SVTPGEPASIS CKSS (SEQ ID NO: 74) | LAWYVQKPGRS PQLLID (SEQ ID NO: 80) | DRASGVPDRFS GSGSEKDFTLS ISRVEAEDVGT YY (SEQ ID NO: 91) | GQGTKVDIK (SEQ ID NO: 93) |
| ePGDM-P VL | DIVLTQSPLSL SVTPGESASIS CKSS (SEQ ID NO: 69) | LAWYLQKPGQS PQLLID (SEQ ID NO: 81) | DRASGVPDRFS GSGSEKDFTLK IDRVETEDVGT YY (SEQ ID NO: 85) | GQGTKVDIK (SEQ ID NO: 93) |

TABLE 4

| Heavy chain (HC) and Light chain (LC) constant region sequences. | |
|---|---|
| heavy chain constant region | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSRDE LTKNQVSLTCLVKGFYPSDI AVEWESNGQPENNYKTTPPV LDSDGSFFLYSKLTVDKSRW QQGNVFSCSVMHEALHNHYT QKSLSLSPGK (SEQ ID NO: 108) |
| light chain constant region | RTVAAPSVFIFPPSDEQLKS GTASVVCLLNNFYPREAKVQ WKVDNALQSGNSQESVTEQD SKDSTYSLSSTLTLSKADYE KHKVYACEVTHQGLSSPVTK SFNRGECG (SEQ ID NO: 109) |
| variant IgG Fc region | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNWY VDGVEVHNAKTKPREEQYNS TYRVVSVLTVLHQDWLNGKE YKCKVSNKALPAPIEKTISK AKGQPREPQVYTLPPSRDEL TKNQVSLTCLVKGFYPSDIA VEWESNGQPENNYKTTPPVL DSDGSFFLYSKLTVDKSRWQ QGNVFSCSVLHEALHSHYTQ KSLSLSPGK (SEQ ID NO: 110) |

In one aspect, provided herein are engineered variants of the PGDM1400 antibody comprising a VH CDR1, VH CDR2, VH CDR3, VL CDR1, VL CDR2, and VL CDR3, wherein one or more of the VH CDR1, VH CDR2, VH CDR3, VL CDR1, VL CDR2, and VL CDR2 is a variant of the corresponding PGDM1400 CDR. In one embodiment, the antibody further comprises a VH FR1, VH FR2, VH FR3, VH FR4, VL FR1, VL FR2, VL FR3, and VL FR4, wherein one or more of the VH FR1, VH FR2, VH FR3, VH FR4, VL FR1, VL FR2, VL FR3, and VL FR4 is a variant of the corresponding PGDM1400 FR.

In one embodiment, an antibody described herein comprises a VH CDR1I, VH CDR2, VH CDR3, VL CDR1, VL CDR2, and VL CDR3, wherein the VH CDR1, VH CDR2, and VH CDR3 comprises the sequence of SEQ ID NO: 94-96, respectively, and the VL CDR1, CDR, and CDR3 comprises the sequence of (SEQ ID NO: 97-99, respectively; wherein at least one of the VH CDR1, VH CDR2, VH CDR3, VL CDR1, VL CDR2, and VL CDR3 comprises a different amino acid sequence than the corresponding CDR of the PGDM1400 antibody.

In one embodiment, the VH CDR1 comprises the sequence of SEQ ID NO: 37. In one embodiment, the VH CDR2 comprises the sequence of SEQ ID NO: 38. In one embodiment, the VH CDR2 comprises the sequence of SEQ ID NO: 39. In one embodiment, the VH CDR3 comprises the sequence of SEQ ID NO: 31. In one embodiment, the VH CDR3 comprises the sequence of SEQ ID NO: 32. In one embodiment, the VH CDR3 comprises the sequence of SEQ ID NO: 33. In one embodiment, the VH CDR3 comprises the sequence of SEQ ID NO: 34. In one embodiment, the VH CDR3 comprises the sequence of SEQ ID NO: 35. In one embodiment, the VL CDR1 comprises the sequence of SEQ ID NO: 41. In one embodiment, the VL CDR1 comprises the sequence of SEQ ID NO: 42. In one embodiment, the VL CDR1 comprises the sequence of SEQ ID NO: 43. In one embodiment, the VL CDR1 comprises the sequence of SEQ ID NO: 44. In one embodiment, the VL CDR2 comprises the sequence of SEQ ID NO: 45. In one embodiment, the VL CDR2 comprises the sequence of SEQ ID NO: 46. In one embodiment, the VL CDR3 comprises the sequence of SEQ ID NO: 30. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of any one of the VH regions of SEQ ID NO: 3-12. In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of any one of the VH regions of SEQ ID NO: 3-12 according to Kabat. In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of any one of the VH regions of SEQ ID NO: 3-12 as shown in Table 2. In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of ePGDM-G VH (SEQ ID NO: 9). In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of ePGDM-G VH (SEQ ID NO: 9) according to Kabat. In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of ePGDM-G VH (SEQ ID NO: 9) as shown in Table 2. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR3 comprises the amino acid sequence of SEQ ID NO: 31-35. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR3 comprises the amino acid sequence of SEQ ID NO: 31-35 comprising 0, 1, 2, 3, 4, or 5 substitutions, insertions, or deletions. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR3 comprises the VH CDR3 of any one of the VH regions of SEQ ID NO: 3-12. In one embodiment, an antibody described herein comprises a VH CDR1, VH CDR2, VH CDR3, VL CDR1, VL CDR2, and VL CDR3, wherein the VH CDR3 comprises the VH CDR3 of any one of the VH regions of SEQ ID NO: 3-12 according to Kabat. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR3 comprises the VH CDR3 of any one of the VH regions of SEQ ID NO: 3-12 comprising 0, 1, 2, 3, 4, or 5 substitutions, insertions, or deletions. In one embodiment, the VH CDR3 is according to Kabat. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 37, the VH CDR2 comprises the amino acid sequence of SEQ ID NO: 38 or 39, and the VH CDR3 comprises the amino acid sequence of SEQ ID NO: 31-35. In one embodiment, an antibody described herein comprises a VH CDR1, VH CDR2, VH CDR3, VL CDR1, VL CDR2, and VL CDR3, wherein the VL CDR1 comprises the amino acid sequence of SEQ ID NO: 41-44, the VL CDR2 comprises the amino acid sequence of SEQ ID NO: 45 or 46, and the VL CDR3 comprises the amino acid sequence of SEQ ID NO: 30. In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 37, the VH CDR2 comprises the amino acid sequence of SEQ ID NO: 38 or 39, the VH CDR3 comprises the amino acid sequence of SEQ ID NO: 31-35, the VL CDR1 comprises the amino acid sequence of SEQ ID NO: 41-44, the VL CDR2 comprises the amino acid sequence of SEQ ID NO: 45 or 46, and the VL CDR3 comprises the amino acid sequence of SEQ ID NO: 30. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 37 comprising 0, 1, 2, 3, 4, or 5 substitutions, insertions, or deletions, the VH CDR2 comprises the amino acid sequence of SEQ ID NO: 38 or 39 comprising 0, 1, 2, 3, 4, or 5 substitutions, insertions, or deletions, and the VH CDR3 comprises the amino acid sequence of SEQ ID NO: 31-35 comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VL CDR1 comprises the amino acid sequence of SEQ ID NO: 41-44 comprising 0, 1, 2, 3, 4, or 5 substitutions, insertions, or deletions, the VL CDR2 comprises the amino acid sequence of SEQ ID NO: 45 or 46 comprising 0, 1, 2, 3, 4, or 5 substitutions, insertions, or deletions, and the VL CDR3 comprises the amino acid sequence of SEQ ID NO: 30 comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 37 comprising 0, 1, 2, 3, 4, or 5 substitutions, insertions, or deletions, the VH CDR2 comprises the amino acid sequence of SEQ ID NO: 38 or 39 comprising 0, 1, 2, 3, 4, or 5 substitutions, insertions, or deletions, the VH CDR3 comprises the amino acid sequence of SEQ ID NO: 31-35 comprising 0, 1, 2, 3, 4, or 5 substitutions, insertions, or deletions, the VL CDR1 comprises the amino acid sequence of SEQ ID NO: 41-44 comprising 0, 1, 2, 3, 4, or 5 substitutions, insertions, or deletions, the VL CDR2 comprises the amino acid sequence of SEQ ID NO: 45 or 46 comprising 0, 1, 2, 3, 4, or 5 substitutions, insertions, or deletions, and the VL CDR3 comprises the amino acid sequence of SEQ ID NO: 30 comprising 0, 1, 2, 3, 4, or 5 substitutions, insertions, or deletions. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 36 or 37, the VH CDR2 comprises the amino acid sequence of SEQ ID NO: 38 or 39, and the VH CDR3 comprises the amino acid sequence of SEQ ID NO: 29 or 31-35. In one embodiment, an antibody described herein comprises a VH CDR1, VH CDR2, VH CDR3, VL CDR1, VL CDR2, and VL CDR3, wherein the VL CDR1 comprises the amino acid sequence of SEQ ID NO: 40-44, the VL CDR2 comprises the amino acid sequence of SEQ ID NO: 45 or 46, and the VL CDR3 comprises the amino acid sequence of SEQ ID NO: 30. In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 36 or 37, the VH CDR2 comprises the amino acid sequence of SEQ ID NO: 38 or 39, and the VH CDR3 comprises the amino acid sequence of SEQ ID NO: 29 or 31-35, the VL CDR1 comprises the amino acid sequence of SEQ ID NO: 40-44, the VL CDR2 comprises the amino acid sequence of SEQ ID NO: 45 or 46, and the VL CDR3 comprises the amino acid sequence of SEQ ID NO: 30. In one embodiment, at least one of the VH CDR1, VH CDR2, VH CDR3, VL CDR1, VL CDR2, and VL CDR3 comprises a different amino acid sequence than the corresponding CDR of the PGDM1400 antibody. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 36 or 37 comprising 0, 1, 2, 3, 4, or 5 substitutions, insertions, or deletions, the VH CDR2 comprises the amino acid sequence of SEQ ID NO: 38 or 39 comprising 0, 1, 2, 3, 4, or 5 substitutions, insertions, or deletions, and the VH CDR3 comprises the amino acid sequence of SEQ ID NO: 29 or 31-35 comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VL CDR1 comprises the amino acid sequence of SEQ ID NO: 40-44 comprising 0, 1, 2, 3, 4, or 5 substitutions, insertions, or deletions, the VL CDR2 comprises the amino acid sequence of SEQ ID NO: 45 or 46 comprising 0, 1, 2, 3, 4, or 5 substitutions, insertions, or deletions, and the VL CDR3 comprises the amino acid sequence of SEQ ID NO: 30 comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1 comprises the amino acid sequence of SEQ ID NO: 36 or 37 comprising 0, 1, 2, 3, 4, or 5 substitutions, insertions, or deletions, the VH CDR2 comprises the amino acid sequence of SEQ ID NO: 38 or 39 comprising 0, 1, 2, 3, 4, or 5 substitutions, insertions, or deletions, the VH CDR3 comprises the amino acid sequence of SEQ ID NO: 29 or 31-35 comprising 0, 1, 2, 3, 4, or 5 substitutions, insertions, or deletions, the VL CDR1 comprises the amino acid sequence of SEQ ID NO: 40-44 comprising 0, 1, 2, 3, 4, or 5 substitutions, insertions, or deletions, the VL CDR2 comprises the amino acid sequence of SEQ ID NO: 45 or 46 comprising 0, 1, 2, 3, 4, or 5 substitutions, insertions, or deletions, and the VL CDR3 comprises the amino acid sequence of SEQ ID NO: 30 comprising 0, 1, 2, 3, 4, or 5 substitutions, insertions, or deletions. In one embodiment, at least one of the VH CDR1, VH CDR2, VH CDR3, VL CDR1, VL CDR2, and VL CDR3 comprises a different amino acid sequence than the corresponding CDR of the PGDM1400 antibody. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 31, respectively. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 32, respectively. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 33, respectively. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 34, respectively. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 35, respectively. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 39, and 31, respectively. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 36, and 34, respectively. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 31, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 32, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 33, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 34, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 38, and 35, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 39, and 31, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR1, VH CDR2, and VH CDR3 comprises the sequence of SEQ ID NO: 37, 36, and 34, respectively, each comprising 0, 1, 2, 3, 4, or 5 substitutions, insertions, or deletions. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VH CDR3 comprises the sequence of SEQ ID NO: 31 comprising 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR3 comprises the sequence of SEQ ID NO: 32 comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR3 comprises the sequence of SEQ ID NO: 33 comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR3 comprises the sequence of SEQ ID NO: 34 comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VH CDR3 comprises the sequence of SEQ ID NO: 35 comprising 0, 1, 2, 3, 4, or 5 substitutions, insertions, or deletions. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the antibody comprises the VL CDR1, VL CDR2, and VL CDR3 of SEQ ID NO: 13-28. In one embodiment, an antibody described herein comprises a VH CDR1, VH CDR2, VH CDR3, VL CDR1, VL CDR2, and VL CDR3, wherein the antibody comprises the VL CDR1, VL CDR2, and VL CDR3 of ePGDM-E VL (SEQ ID NO: 17). In one embodiment, an antibody described herein comprises a VH CDR1, VH CDR2, VH CDR3, VL CDR1, VL CDR2, and VL CDR3, wherein the antibody comprises the VL CDR1, VL CDR2, and VL CDR3 of ePGDM-I VL (SEQ ID NO: 21). In one embodiment, an antibody described herein comprises a VH CDR1, VH CDR2, VH CDR3, VL CDR1, VL CDR2, and VL CDR3, wherein the antibody comprises the VL CDR1, VL CDR2, and VL CDR3 of ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 41, 46, and 30, respectively. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 42, 45, and 30, respectively. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 41, 45, and 30, respectively. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 43, 45, and 30, respectively. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 43, 46, and 30, respectively. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 44, 45, and 30, respectively. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 41, 46, and 30, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 42, 45, and 30, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 41, 45, and 30, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 43, 45, and 30, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 43, 46, and 30, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3, wherein the VL CDR1, VL CDR2 and VL CDR3 comprises SEQ ID NO: 44, 45, and 30, respectively, each comprising 0, 1, 2, 3, 4, or 5 substitutions, insertions, or deletions. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of a VH of SEQ ID NO: 3-12 and the VL CDR1, VL CDR2, and VL CDR3 of VL of SEQ ID NO: 13-28. In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of the VH of SEQ ID NO: 1 and the VL CDR1, VL CDR2, and VL CDR3 of VL of SEQ ID NO: 13-28. In one embodiment, an antibody described herein comprises a VH CDR1, VH CDR2, VH CDR3, VL CDR1, VL CDR2, and VL CDR3, wherein the antibody comprises the VH CDR1, VH CDR2, and VH CDR3 of a VH of SEQ ID NO: 3-12 and the VL CDR1, VL CDR2, and VL CDR3 of the VL of SEQ ID NO: 2. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3 comprising the sequence of SEQ ID NO: 36, 38, 29, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 36, 38, 29, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 36, 38, 29, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 36, 38, 29, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 36, 38, 29, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 36, 38, 29, 44, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 31, 40, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 31, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 31, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 31, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 31, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 31, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 31, 44, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 32, 40, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 32, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 32, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 32, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 32, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 32, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 32, 44, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 33, 40, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 33, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 33, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 33, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 33, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 33, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 33, 44, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 34, 40, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 34, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 34, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 34, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 34, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 34, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 34, 44, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 35, 40, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 35, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 35, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 35, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 35, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 35, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 38, 35, 44, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 31, 40, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 31, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 31, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 31, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 31, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 31, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 31, 44, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 34, 40, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 34, 41, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 34, 42, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 34, 41, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 34, 43, 45, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 34, 43, 46, and 30, respectively. In one embodiment, an antibody described herein comprises a VH CDR1, VH CDR2, VH CDR3, VL CDR1, VL CDR2, and VL CDR3 comprising the sequence of SEQ ID NO: 37, 39, 34, 44, 45, and 30, respectively. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, and VL CDR3 comprising the sequence of SEQ ID NO: 37, 38, 34, 43, 45, and 30, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3 comprising the sequence of SEQ ID NO: 37, 38, 34, 44, 45, and 30, respectively, each comprising 0, 1, 2, 3, 4, or 5 substitutions, insertions, or deletions. In one embodiment, an antibody described herein comprises a VH CDR1, VH CDR2, VH CDR3, VL CDR1, VL CDR2, and VL CDR3 comprising the sequence of SEQ ID NO: 37, 38, 34, 43, 45, and 30, respectively, each comprising 0, 1, 2, 3, 4, or 5 substitutions, insertions, or deletions. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein further comprises a VH FR1, VH FR2, VH FR3, and VH FR4, wherein the VH FR1, VH FR2, VH FR3, and VH FR4 comprises SEQ ID NO: 100-103, respectively. In one embodiment, the VH FR1 comprises the sequence of SEQ ID NO: 48. In one embodiment, VH FR1 comprises the sequence of SEQ ID NO: 49. In one embodiment, the VH FR1 comprises the sequence of SEQ ID NO: 50. In one embodiment, the VH FR1 comprises the sequence of SEQ ID NO: 51. In one embodiment, the VH FR1 comprises the sequence of SEQ ID NO: 52. In one embodiment, the VH FR1 comprises the sequence of SEQ ID NO: 53. In one embodiment, the VH FR2 comprises the sequence of SEQ ID NO: 54. In one embodiment, the VH FR2 comprises the sequence of SEQ ID NO: 55. In one embodiment, the VH FR2 comprises the sequence of SEQ ID NO: 56. In one embodiment, the VH FR2 comprises the sequence of SEQ ID NO: 57. In one embodiment, the VH FR3 comprises the sequence of SEQ ID NO: 59. In one embodiment, the VH FR3 comprises the sequence of SEQ ID NO: 60. In one embodiment, VH FR3 comprises the sequence of SEQ ID NO: 61. In one embodiment, the VH FR3 comprises the sequence of SEQ ID NO: 62. In one embodiment, the VH FR3 comprises the sequence of SEQ ID NO: 63. In one embodiment, the VH FR3 comprises the sequence of SEQ ID NO: 64. In one embodiment, the VH FR3 comprises the sequence of SEQ ID NO: 65. In one embodiment, the VH FR4 comprises the sequence of SEQ ID NO: 66.

In one embodiment, the VH FR1 comprises the sequence of SEQ ID NO: 48 comprising 0, 1, 2, 3, 4, or 5 substitutions, insertions, or deletions. In one embodiment, VH FR1 comprises the sequence of SEQ ID NO: 49 comprising 0, 1, 2, 3, 4, or 5 substitutions, insertions, or deletions. In one embodiment, the VH FR1 comprises the sequence of SEQ ID NO: 50 comprising 0, 1, 2, 3, 4, or 5 substitutions, insertions, or deletions. In one embodiment, the VH FR1 comprises the sequence of SEQ ID NO: 51 comprising 0, 1, 2, 3, 4, or 5 substitutions, insertions, or deletions. In one embodiment, the VH FR1 comprises the sequence of SEQ ID NO: 52 comprising 0, 1, 2, 3, 4, or 5 substitutions, insertions, or deletions. In one embodiment, the VH FR1 comprises the sequence of SEQ ID NO: 53 comprising 0, 1, 2, 3, 4, or 5 substitutions, insertions, or deletions. In one embodiment, the VH FR2 comprises the sequence of SEQ ID NO: 54 comprising 0, 1, 2, 3, 4, or 5 substitutions, insertions, or deletions. In one embodiment, the VH FR2 comprises the sequence of SEQ ID NO: 55 comprising 0, 1, 2, 3, 4, or 5 substitutions, insertions, or deletions. In one embodiment, the VH FR2 comprises the sequence of SEQ ID NO: 56 comprising 0, 1, 2, 3, 4, or 5 substitutions, insertions, or deletions. In one embodiment, the VH FR2 comprises the sequence of SEQ ID NO: 57 comprising 0, 1, 2, 3, 4, or 5 substitutions, insertions, or deletions. In one embodiment, the VH FR3 comprises the sequence of SEQ ID NO: 59 comprising 0, 1, 2, 3, 4, or 5 substitutions, insertions, or deletions. In one embodiment, the VH FR3 comprises the sequence of SEQ ID NO: 60 comprising 0, 1, 2, 3, 4, or 5 substitutions, insertions, or deletions. In one embodiment, VH FR3 comprises the sequence of SEQ ID NO: 61 comprising 0, 1, 2, 3, 4, or 5 substitutions, insertions, or deletions. In one embodiment, the VH FR3 comprises the sequence of SEQ ID NO: 62 comprising 0, 1, 2, 3, 4, or 5 substitutions, insertions, or deletions. In one embodiment, the VH FR3 comprises the sequence of SEQ ID NO: 63 comprising 0, 1, 2, 3, 4, or 5 substitutions, insertions, or deletions. In one embodiment, the VH FR3 comprises the sequence of SEQ ID NO: 64 comprising 0, 1, 2, 3, 4, or 5 substitutions, insertions, or deletions. In one embodiment, the VH FR3 comprises the sequence of SEQ ID NO: 65 comprising 0, 1, 2, 3, 4, or 5 substitutions, insertions, or deletions. In one embodiment, the VH FR4 comprises the sequence of SEQ ID NO: 66 comprising 0, 1, 2, 3, 4, or 5 substitutions, insertions, or deletions.

In one embodiment, the VH FR1, VH FR2, VH FR3, and VH FR4 comprises the sequence of SEQ ID NO: 47, 54, 58, and 66, respectively. In one embodiment, the VH FR1, VH FR2, VH FR3, and VH FR4 comprises the sequence of SEQ ID NO: 48, 55, 59, and 66, respectively. In one embodiment, the VH FR1, VH FR2, VH FR3, and VH FR4 comprises the sequence of SEQ ID NO: 49, 56, 60, and 66, respectively. In one embodiment, the VH FR1, VH FR2, VH FR3, and VH FR4 comprises the sequence of SEQ ID NO: 50, 55, 61, and 66, respectively. In one embodiment, the VH FR1, VH FR2, VH FR3, and VH FR4 comprises the sequence of SEQ ID NO: 51, 55, 62, and 66, respectively. In one embodiment, the VH FR1, VH FR2, VH FR3, and VH FR4 comprises the sequence of SEQ ID NO: 52, 56, 63, and 66, respectively. In one embodiment, the VH FR1, VH FR2, VH FR3, and VH FR4 comprises the sequence of SEQ ID NO: 50, 54, 59, and 66, respectively. In one embodiment, the VH FR1, VH FR2, VH FR3, and VH FR4 comprises the sequence of SEQ ID NO: 53, 55, 64, and 66, respectively. In one embodiment, the VH FR1, VH FR2, VH FR3, and VH FR4 comprises the sequence of SEQ ID NO: 52, 55, 65, and 66, respectively. In one embodiment, the VH FR1, VH FR2, VH FR3, and VH FR4 comprises the sequence of SEQ ID NO: 53, 57, 61, and 66, respectively. In one embodiment, the VH FR1, VH FR2, VH FR3, and VH FR4 comprises the sequence of SEQ ID NO: 51, 55, 59, and 66, respectively.

In one embodiment, the VH FR1, VH FR2, VH FR3, and VH FR4 comprises the sequence of SEQ ID NO: 47, 54, 58, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 48, 55, 59, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 49, 56, 60, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 50, 55, 61, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 51, 55, 62, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 52, 56, 63, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 50, 54, 59, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 53, 55, 64, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 52, 55, 65, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 53, 57, 61, and 66, respectively, each comprising 0, 1, 2, 3, 4, or 5 substitutions, insertions, or deletions. In one embodiment, the VH FR1, VH FR2, VH FR3, and VH FR4 comprises the sequence of SEQ ID NO: 51, 55, 59, and 66, respectively, each comprising 0, 1, 2, 3, 4, or 5 substitutions, insertions, or deletions.

In one embodiment, an antibody described herein further comprises a VL FR1, VL FR2, VL FR3, and VL FR4, wherein the VL FR1, VL FR2, VL FR3 and VL FR4 comprises the sequence of SEQ ID NO: 104-107, respectively. In one embodiment, the VL FR1 comprises the sequence of SEQ ID NO: 40. In one embodiment, the VL FR1 comprises the sequence of SEQ ID NO: 68. In one embodiment, the VL FR1 comprises the sequence of SEQ ID NO: 69. In one embodiment, the VL FR1 comprises the sequence of SEQ ID NO: 70. In one embodiment, the VL FR1 comprises the sequence of SEQ ID NO: 71. In one embodiment, the VL FR1 comprises the sequence of SEQ ID NO: 72. In one embodiment, the VL FR1 comprises the sequence of SEQ ID NO: 73. In one embodiment, the VL FR1 comprises the sequence of SEQ ID NO: 74. In one embodiment, the VL FR2 comprises the sequence of SEQ ID NO: 75. In one embodiment, the VL FR2 comprises the sequence of SEQ ID NO: 76. In one embodiment, the VL FR2 comprises the sequence of SEQ ID NO: 77. In one embodiment, the VL FR2 comprises the sequence of SEQ ID NO: 78. In one embodiment, the VL FR2 comprises the sequence of SEQ ID NO: 79. In one embodiment, the VL FR2 comprises the sequence of SEQ ID NO: 80. In one embodiment, the VL FR2 comprises the sequence of SEQ ID NO: 81. In one embodiment, the VL FR3 comprises the sequence of SEQ ID NO: 82. In one embodiment, the VL FR3 comprises the sequence of SEQ ID NO: 83. In one embodiment, the VL FR3 comprises the sequence of SEQ ID NO: 84. In one embodiment, the VL FR3 comprises the sequence of SEQ ID NO: 85. In one embodiment, the VL FR3 comprises the sequence of SEQ ID NO: 86. In one embodiment, the VL FR3 comprises the sequence of SEQ ID NO: 87. In one embodiment, the VL FR3 comprises the sequence of SEQ ID NO: 88. In one embodiment, the VL FR3 comprises the sequence of SEQ ID NO: 89. In one embodiment, the VL FR3 comprises the sequence of SEQ ID NO: 90. In one embodiment, the VL FR3 comprises the sequence of SEQ ID NO: 91. In one embodiment, the VL FR3 comprises the sequence of SEQ ID NO: 92. In one embodiment, the VL FR4 comprises the sequence of SEQ ID NO: 93.

In one embodiment, an antibody described herein further comprises a VL FR1, VL FR2, VL FR3, and VL FR4, wherein the VL FR1, VL FR2, VL FR3 and VL FR4 comprises the sequence of SEQ ID NO: 104-107, respectively, comprising 0, 1, 2, 3, 4, or 5 substitutions, insertions, or deletions. In one embodiment, the VL FR1 comprises the sequence of SEQ ID NO: 40, comprising 0, 1, 2, 3, 4, or 5 substitutions, insertions, or deletions. In one embodiment, the VL FR1 comprises the sequence of SEQ ID NO: 68, comprising 0, 1, 2, 3, 4, or 5 substitutions, insertions, or deletions. In one embodiment, the VL FR1 comprises the sequence of SEQ ID NO: 69, comprising 0, 1, 2, 3, 4, or 5 substitutions, insertions, or deletions. In one embodiment, the VL FR1 comprises the sequence of SEQ ID NO: 70, comprising 0, 1, 2, 3, 4, or 5 substitutions, insertions, or deletions. In one embodiment, the VL FR1 comprises the sequence of SEQ ID NO: 71, comprising 0, 1, 2, 3, 4, or 5 substitutions, insertions, or deletions. In one embodiment, the VL FR1 comprises the sequence of SEQ ID NO: 72, comprising 0, 1, 2, 3, 4, or 5 substitutions, insertions, or deletions. In one embodiment, the VL FR1 comprises the sequence of SEQ ID NO: 73, comprising 0, 1, 2, 3, 4, or 5 substitutions, insertions, or deletions. In one embodiment, the VL FR1 comprises the sequence of SEQ ID NO: 74, comprising 0, 1, 2, 3, 4, or 5 substitutions, insertions, or deletions. In one embodiment, the VL FR2 comprises the sequence of SEQ ID NO: 75, comprising 0, 1, 2, 3, 4, or 5 substitutions, insertions, or deletions. In one embodiment, the VL FR2 comprises the sequence of SEQ ID NO: 76, comprising 0, 1, 2, 3, 4, or 5 substitutions, insertions, or deletions. In one embodiment, the VL FR2 comprises the sequence of SEQ ID NO: 77, comprising 0, 1, 2, 3, 4, or 5 substitutions, insertions, or deletions. In one embodiment, the VL FR2 comprises the sequence of SEQ ID NO: 78, comprising 0, 1, 2, 3, 4, or 5 substitutions, insertions, or deletions. In one embodiment, the VL FR2 comprises the sequence of SEQ ID NO: 79, comprising 0, 1, 2, 3, 4, or 5 substitutions, insertions, or deletions. In one embodiment, the VL FR2 comprises the sequence of SEQ ID NO: 80, comprising 0, 1, 2, 3, 4, or 5 substitutions, insertions, or deletions. In one embodiment, the VL FR2 comprises the sequence of SEQ ID NO: 81, comprising 0, 1, 2, 3, 4, or 5 substitutions, insertions, or deletions. In one embodiment, the VL FR3 comprises the sequence of SEQ ID NO: 82, comprising 0, 1, 2, 3, 4, or 5 substitutions, insertions, or deletions. In one embodiment, the VL FR3 comprises the sequence of SEQ ID NO: 83, comprising 0, 1, 2, 3, 4, or 5 substitutions, insertions, or deletions. In one embodiment, the VL FR3 comprises the sequence of SEQ ID NO: 84, comprising 0, 1, 2, 3, 4, or 5 substitutions, insertions, or deletions. In one embodiment, the VL FR3 comprises the sequence of SEQ ID NO: 85, comprising 0, 1, 2, 3, 4, or 5 substitutions, insertions, or deletions. In one embodiment, the VL FR3 comprises the sequence of SEQ ID NO: 86, comprising 0, 1, 2, 3, 4, or 5 substitutions, insertions, or deletions. In one embodiment, the VL FR3 comprises the sequence of SEQ ID NO: 87, comprising 0, 1, 2, 3, 4, or 5 substitutions, insertions, or deletions. In one embodiment, the VL FR3 comprises the sequence of SEQ ID NO: 88, comprising 0, 1, 2, 3, 4, or 5 substitutions, insertions, or deletions. In one embodiment, the VL FR3 comprises the sequence of SEQ ID NO: 89, comprising 0, 1, 2, 3, 4, or 5 substitutions, insertions, or deletions. In one embodiment, the VL FR3 comprises the sequence of SEQ ID NO: 90, comprising 0, 1, 2, 3, 4, or 5 substitutions, insertions, or deletions. In one embodiment, the VL FR3 comprises the sequence of SEQ ID NO: 91, comprising 0, 1, 2, 3, 4, or 5 substitutions, insertions, or deletions. In one embodiment, the VL FR3 comprises the sequence of SEQ ID NO: 92, comprising 0, 1, 2, 3, 4, or 5 substitutions, insertions, or deletions. In one embodiment, the VL FR4 comprises the sequence of SEQ ID NO: 93, comprising 0, 1, 2, 3, 4, or 5 substitutions, insertions, or deletions.

In one embodiment, the VL FR1, VL FR2, VL FR3, and VL FR4 comprises the sequence of SEQ ID NO: 67, 75, 82, and 93, respectively. In one embodiment, the VL FR1, VL FR2, VL FR3, and VL FR4 comprises the sequence of SEQ ID NO: 68, 76, 83, and 93, respectively. In one embodiment, the VL FR1, VL FR2, VL FR3, and VL FR4 comprises the sequence of SEQ ID NO: 69, 77, 84, and 93, respectively. In one embodiment, the VL FR1, VL FR2, VL FR3, and VL FR4 comprises the sequence of SEQ ID NO: 70, 78, 85, and 93, respectively. In one embodiment, the VL FR1, VL FR2, VL FR3, and VL FR4 comprises the sequence of SEQ ID NO: 71, 79, 86, and 93, respectively. In one embodiment, the VL FR1, VL FR2, VL FR3, and VL FR4 comprises the sequence of SEQ ID NO: 72, 80, 87, and 93, respectively. In one embodiment, the VL FR1, VL FR2, VL FR3, and VL FR4 comprises the sequence of SEQ ID NO: 68, 76, 88, and 93, respectively. In one embodiment, the VL FR1, VL FR2, VL FR3, and VL FR4 comprises the sequence of SEQ ID NO: 69, 78, 89, and 93, respectively. In one embodiment, the VL FR1, VL FR2, VL FR3, and VL FR4 comprises the sequence of SEQ ID NO: 69, 79, 89, and 93, respectively. In one embodiment, the VL FR1, VL FR2, VL FR3, and VL FR4 comprises the sequence of SEQ ID NO: 69, 80, 90, and 93, respectively. In one embodiment, the VL FR1, VL FR2, VL FR3, and VL FR4 comprises the sequence of SEQ ID NO: 73, 80, 91, and 93, respectively. In one embodiment, the VL FR1, VL FR2, VL FR3, and VL FR4 comprises the sequence of SEQ ID NO: 68, 80, 88, and 93, respectively. In one embodiment, the VL FR1, VL FR2, VL FR3, and VL FR4 comprises the sequence of SEQ ID NO: 74, 79, 88, and 93, respectively. In one embodiment, the VL FR1, VL FR2, VL FR3, and VL FR4 comprises the sequence of SEQ ID NO: 69, 78, 92, and 93, respectively. In one embodiment, the VL FR1, VL FR2, VL FR3, and VL FR4 comprises the sequence of SEQ ID NO: 74, 76, 91, and 93, respectively. In one embodiment, the VL FR1, VL FR2, VL FR3, and VL FR4 comprises the sequence of SEQ ID NO: 74, 80, 91, and 93, respectively. In one embodiment, the VL FR1, VL FR2, VL FR3, and VL FR4 comprises the sequence of SEQ ID NO: 69, 81, 85, and 93, respectively.

In one embodiment, the VL FR1, VL FR2, VL FR3, and VL FR4 comprises the sequence of SEQ ID NO: 67, 75, 82, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 68, 76, 83, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 69, 77, 84, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 70, 78, 85, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 71, 79, 86, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 72, 80, 87, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 68, 76, 88, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 69, 78, 89, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 69, 79, 89, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 69, 80, 90, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 73, 80, 91, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 68, 80, 88, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 74, 79, 88, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 69, 78, 92, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 74, 76, 91, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 74, 80, 91, and 93, respectively, each comprising 0, 1, 2, 3, 4, or 5 substitutions, insertions, or deletions. In one embodiment, the VL FR1, VL FR2, VL FR3, and VL FR4 comprises the sequence of SEQ ID NO: 69, 81, 85, and 93, respectively, each comprising 0, 1, 2, 3, 4, or 5 substitutions, insertions, or deletions.

In one embodiment, an antibody described herein comprises VH framework regions comprising one or more of A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, the VH framework regions comprise two or more, three or more, four or more, or five or more of A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, the VH framework regions comprise A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, an antibody described herein comprises VH framework regions comprising one or more, two or more, three or more, four or more, or five or more of A at H2, Q at H3, V at H5, N at H24, Q at H39, and E at H85, wherein the VH framework residues are numbered according to Kabat. In one embodiment, an antibody described herein comprises VH framework regions comprising A at H2, Q at H3, V at H5, N at H24, Q at H39, and E at H85, wherein the VH framework residues are numbered according to Kabat. In one embodiment, an antibody described herein comprises VH framework regions comprising one or more, two or more, or three or more of Q at H3, V at H5, N at H24, E at H85, wherein the VH framework residues are numbered according to Kabat. In one embodiment, an antibody described herein comprises VH framework regions comprising Q at H3, V at H5, N at H24, E at H85, wherein the VH framework residues are numbered according to Kabat. In one embodiment, the VH has at least about 70%, at least about 75%, at least about 80%, at least about 90%, or at least about 95% sequence identity to SEQ ID NO: 1. In one embodiment, the VH has at least about 70%, at least about 75%, at least about 80%, at least about 90%, or at least about 95% sequence identity to SEQ ID NO: 3-12. In one embodiment, the VH has at least about 70%, at least about 75%, at least about 80%, at least about 90%, or at least about 95% sequence identity to SEQ ID NO: 9.

In one embodiment, an antibody described herein comprises VL framework regions comprising one or more of a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, the VL framework regions comprise two or more, three or more, four or more, or five or more of a a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, the VL framework regions comprise a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, an antibody described herein comprises VL framework regions comprising one or more, two or more, three or more, four or more, or five or more of a I at L2, L at L9, D at L26, E at L53, R at L68, D at L76, and A at L80, wherein the VL framework residues are numbered according to Kabat. In one embodiment, an antibody described herein comprises VL framework regions comprising I at L2, L at L9, D at L26, E at L53, R at L68, D at L76, and A at L80, wherein the VL framework residues are numbered according to Kabat. In one embodiment, an antibody described herein comprises VL framework regions comprising one or more, two or more, three or more, four or more, or five or more of A L at L9, E at L53, R at L68, S at L74, D at L76, and A at L80, wherein the VL framework residues are numbered according to Kabat. In one embodiment, an antibody described herein comprises VL framework regions comprising A L at L9, E at L53, R at L68, S at L74, D at L76, and A at L80, wherein the VL framework residues are numbered according to Kabat. In one embodiment, an antibody described herein comprises VL framework regions comprising one or more, two or more, three or more, or four or more of I at L2, L at L9, L at L48, E at L53, E at L68, wherein the VL framework residues are numbered according to Kabat. In one embodiment, an antibody described herein comprises VL framework regions comprising I at L2, L at L9, L at L48, E at L53, E at L68, wherein the VL framework residues are numbered according to Kabat. In one embodiment, an antibody described herein comprises VL framework regions comprising one or more, or two or more of D at L49, E or D at L53, E or R at L68, wherein the VL framework residues are numbered according to Kabat. In one embodiment, an antibody described herein comprises VL framework regions comprising D at L49, E or D at L53, E or R at L68, wherein the VL framework residues are numbered according to Kabat. In one embodiment, the VL has at least about 70%, at least about 75%, at least about 80%, at least about 90%, or at least about 95% sequence identity to SEQ ID NO: 2. In one embodiment, the VL has at least about 70%, at least about 75%, at least about 80%, at least about 90%, or at least about 95% sequence identity to SEQ ID NO: 13-28.

In one aspect, provided herein are engineered variants of the PGDM1400 antibody comprising a VH CDR1, VH CDR2, VH CDR3, VL CDR1, VL CDR2, VL CDR3, VH framework and VL framework wherein one or both of the VH framework and the VL framework comprises a variant of the corresponding PGDM1400 framework.

In one embodiment, an antibody described herein comprises a VH CDR1, VH CDR2, VH CDR3, VL CDR1, VL CDR2, VL CDR3, VH framework and VL framework wherein the VH framework comprises one or more of A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, an antibody described herein comprises a VH CDR1, VH CDR2, VH CDR3, VL CDR1, VL CDR2, VL CDR3, VH framework and VL framework wherein the VH framework comprises two or more, three or more, four or more, five or more, six or more, seven or more, eight or more, nine or more, or ten or more of A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, an antibody described herein comprises a VH CDR1, VH CDR2, VH CDR3, VL CDR1, VL CDR2, VL CDR3, VH framework and VL framework wherein the VH framework comprises A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, an antibody described herein comprises VH framework regions comprising one or more, two or more, three or more, four or more, or five or more of A at H2, Q at H3, V at H5, N at H24, Q at H39, and E at H85, wherein the VH framework residues are numbered according to Kabat. In one embodiment, an antibody described herein comprises VH framework regions comprising A at H2, Q at H3, V at H5, N at H24, Q at H39, and E at H85, wherein the VH framework residues are numbered according to Kabat. In one embodiment, an antibody described herein comprises VH framework regions comprising one or more, two or more, or three or more of Q at H3, V at H5, N at H24, E at H85, wherein the VH framework residues are numbered according to Kabat. In one embodiment, an antibody described herein comprises VH framework regions comprising Q at H3, V at H5, N at H24, E at H85, wherein the VH framework residues are numbered according to Kabat. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, VL CDR3, VH framework and VL framework wherein the VL framework comprises one or more of a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, an antibody described herein comprises a VH CDR1, VH CDR2, VH CDR3, VL CDR1, VL CDR2, VL CDR3, VH framework and VL framework wherein the VL framework comprises two or more, three or more, four or more, or five or more of a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, an antibody described herein comprises a VH CDR1, VH CDR2, VH CDR3, VL CDR1, VL CDR2, VL CDR3, VH framework and VL framework wherein the VL framework comprises a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, an antibody described herein comprises VL framework regions comprising one or more, two or more, three or more, four or more, or five or more of a I at L2, L at L9, D at L26, E at L53, R at L68, D at L76, and A at L80, wherein the VL framework residues are numbered according to Kabat. In one embodiment, an antibody described herein comprises VL framework regions comprising I at L2, L at L9, D at L26, E at L53, R at L68, D at L76, and A at L80, wherein the VL framework residues are numbered according to Kabat. In one embodiment, an antibody described herein comprises VL framework regions comprising one or more, two or more, three or more, four or more, or five or more of L at L9, E at L53, R at L68, S at L74, D at L76, and A at L80, wherein the VL framework residues are numbered according to Kabat. In one embodiment, an antibody described herein comprises VL framework regions comprising L at L9, E at L53, R at L68, S at L74, D at L76, and A at L80, wherein the VL framework residues are numbered according to Kabat. In one embodiment, an antibody described herein comprises VL framework regions comprising one or more, two or more, three or more, or four or more of I at L2, L at L9, L at L48, E at L53, E at L68, wherein the VL framework residues are numbered according to Kabat. In one embodiment, an antibody described herein comprises VL framework regions comprising I at L2, L at L9, L at L48, E at L53, E at L68, wherein the VL framework residues are numbered according to Kabat. In one embodiment, an antibody described herein comprises VL framework regions comprising one or more, or two or more of D at L49, E or D at L53, E or R at L68, wherein the VL framework residues are numbered according to Kabat. In one embodiment, an antibody described herein comprises VL framework regions comprising D at L49, E or D at L53, E or R at L68, wherein the VL framework residues are numbered according to Kabat. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, VL CDR3, VH framework and VL framework wherein the VH and VL frameworks comprise one or more of A at H2, Q at H3, V at H5, A at H9, A at H16, N at H24, Q at H39, E at H46, E at H56, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80, wherein the VH and VL framework residues are numbered according to Kabat. In one embodiment, an antibody described herein comprises a VH CDR1, VH CDR2, VH CDR3, VL CDR1, VL CDR2, VL CDR3, VH framework and VL framework wherein the VH and VL frameworks comprise two or more, three or more, four or more, five or more, six or more, seven or more, eight or more, nine or more, or ten or more of A at H2, Q at H3, V at H5, A at H9, A at H16, N at H24, Q at H39, E at H46, E at H56, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80, wherein the VH and VL framework residues are numbered according to Kabat. In one embodiment, an antibody described herein comprises a VH CDR1, VH CDR2, VH CDR3, VL CDR1, VL CDR2, VL CDR3, VH framework and VL framework wherein the VH and VL frameworks comprise A at H2, Q at H3, V at H5, A at H9, A at H16, N at H24, Q at H39, E at H46, E at H56, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80, wherein the VH and VL framework residues are numbered according to Kabat. In one embodiment, the VH and VL framework regions comprise one or more, two or more, three or more, four or more, or five or more of A at H2, Q at H3, V at H5, N at H24, Q at H39, E at H85, I at L2, L at L9, D at L26, E at L53, R at L68, D at L76, and A at L80, wherein the VH and VL framework residues are numbered according to Kabat. In one embodiment, the VH and VL framework regions comprise A at H2, Q at H3, V at H5, N at H24, Q at H39, E at H85, I at L2, L at L9, D at L26, E at L53, R at L68, D at L76, and A at L80, wherein the VH and VL framework residues are numbered according to Kabat. In one embodiment, the VH and VL framework regions comprise one or more, two or more, three or more, four or more, or five or more of A at H2, Q at H3, V at H5, N at H24, Q at H39, E at H85, L at L9, E at L53, R at L68, S at L74, D at L76, and A at L80, wherein the VH and VL framework residues are numbered according to Kabat. In one embodiment, the VH and VL framework regions comprise A at H2, Q at H3, V at H5, N at H24, Q at H39, E at H85, L at L9, E at L53, R at L68, S at L74, D at L76, and A at L80, wherein the VH and VL framework residues are numbered according to Kabat. In one embodiment, the VH and VL framework regions comprise one or more, two or more, three or more, four or more, or five or more of A at H2, Q at H3, V at H5, N at H24, Q at H39, E at H85, I at L2, L at L9, L at L48, E at L53, E at L68, wherein the VH and VL framework residues are numbered according to Kabat. In one embodiment, the VH and VL framework regions comprise A at H2, Q at H3, V at H5, N at H24, Q at H39, E at H85, I at L2, L at L9, L at L48, E at L53, E at L68, wherein the VH and VL framework residues are numbered according to Kabat. In one embodiment, the VH and VL framework regions comprise one or more, two or more, three or more, four or more, or five or more of Q at H3, V at H5, N at H24, E at H85, D at L49, E or D at L53, E or R at L68, wherein the VH and VL framework residues are numbered according to Kabat. In one embodiment, the VH and VL framework regions comprise Q at H3, V at H5, N at H24, E at H85, D at L49, E or D at L53, E or R at L68, wherein the VH and VL framework residues are numbered according to Kabat. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, VL CDR3, VH framework and VL framework wherein the antibody comprises the VH framework of the ePGDM-G VH (SEQ ID NO: 9). In one embodiment, an antibody described herein comprises a VH CDR1, VH CDR2, VH CDR3, VL CDR1, VL CDR2, VL CDR3, VH framework and VL framework wherein the antibody comprises the VH framework of SEQ ID NO: 3-12. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP)

In one embodiment, an antibody described herein comprises a VH CDR1, VH CDR2, VH CDR3, VL CDR1, VL CDR2, VL CDR3, VH framework and VL framework wherein the antibody comprises the VL framework of the ePGDM-E VL (SEQ ID NO: 17). In one embodiment, an antibody described herein comprises a VH CDR1, VH CDR2, VH CDR3, VL CDR1, VL CDR2, VL CDR3, VH framework and VL framework wherein the antibody comprises the VL framework of the ePGDM-I VL (SEQ ID NO: 21). In one embodiment, an antibody described herein comprises a VH CDR1, VH CDR2, VH CDR3, VL CDR1, VL CDR2, VL CDR3, VH framework and VL framework wherein the antibody comprises the VL framework of the ePGDM-M VL (SEQ ID NO: 25). In one embodiment, an antibody described herein comprises a VH CDR1, VH CDR2, VH CDR3, VL CDR1, VL CDR2, VL CDR3, VH framework and VL framework wherein the antibody comprises the VL framework of SEQ ID NO: 13-28. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, VL CDR3, VH framework and VL framework wherein the antibody comprises (i) the VH framework of the ePGDM-G VH (SEQ ID NO: 9) and (ii) the VL framework of the ePGDM-E VL (SEQ ID NO: 17). In one embodiment, an antibody described herein comprises a VH CDR1, VH CDR2, VH CDR3, VL CDR1, VL CDR2, VL CDR3, VH framework and VL framework wherein the antibody comprises (i) the VH framework of the ePGDM-G VH (SEQ ID NO: 9) and (ii) the VL framework of the ePGDM-I VL (SEQ ID NO: 21). In one embodiment, an antibody described herein comprises a VH CDR1, VH CDR2, VH CDR3, VL CDR1, VL CDR2, VL CDR3, VH framework and VL framework wherein the antibody comprises (i) the VH framework of the ePGDM-G VH (SEQ ID NO: 9) and (ii) the VL framework of the ePGDM-M VL (SEQ ID NO: 25). In one embodiment, an antibody described herein comprises a VH CDR1, VH CDR2, VH CDR3, VL CDR1, VL CDR2, VL CDR3, VH framework and VL framework wherein the antibody comprises (i) the VH framework of SEQ ID NO: 3-12 and (ii) the VL framework of SEQ ID NO: 13-28. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH CDR1, VH CDR2, VH CDR3, VL CDR1, VL CDR2, VL CDR3, VH framework and VL framework wherein the antibody comprises a VH framework with at least about 70%, at least about 80%, at least about 90%, at least about 95%, at least about 96%, at least about 97%, at least about 98%, or at least about 99% sequence identity to the VH framework of the SEQ ID NO: 3-12 VH. In one embodiment, an antibody described herein comprises a VH CDR1, VH CDR2, VH CDR3, VL CDR1, VL CDR2, VL CDR3, VH framework and VL framework wherein the antibody comprises a VH framework with at least about 70%, at least about 80%, at least about 90%, at least about 95%, at least about 96%, at least about 97%, at least about 98%, or at least about 99% sequence identity to the VH framework of the ePGDM-G VH (SEQ ID NO: 9). In one embodiment, an antibody described herein comprises a VH CDR1, VH CDR2, VH CDR3, VL CDR1, VL CDR2, VL CDR3, VH framework and VL framework wherein the antibody comprises a VH framework with at least about 90%, sequence identity to the VH framework of the SEQ ID NO: 3-12 VH. In one embodiment, an antibody described herein comprises a VH CDR1, VH CDR2, VH CDR3, VL CDR1, VL CDR2, VL CDR3, VH framework and VL framework wherein the antibody comprises a VH framework with at least about 90%, sequence identity to the VH framework of the ePGDM-G VH (SEQ ID NO: 9). In one embodiment, an antibody described herein comprises a VH CDR1, VH CDR2, VH CDR3, VL CDR1, VL CDR2, VL CDR3, VH framework and VL framework wherein the antibody comprises a VL framework with at least about 70%, at least about 80%, at least about 90%, at least about 95%, at least about 96%, at least about 97%, at least about 98%, or at least about 99% sequence identity to the VL framework of the SEQ ID NO: 13-28 VL. In one embodiment, an antibody described herein comprises a VH CDR1, VH CDR2, VH CDR3, VL CDR1, VL CDR2, VL CDR3, VH framework and VL framework wherein the antibody comprises a VL framework with at least about 70%, at least about 80%, at least about 90%, at least about 95%, at least about 96%, at least about 97%, at least about 98%, or at least about 99% sequence identity to the VL framework of the ePGDM-E VL (SEQ ID NO: 17), ePGDM-I VL (SEQ ID NO: 21), or ePGDM-M VL (SEQ ID NO: 25). In one embodiment, an antibody described herein comprises a VH CDR1, VH CDR2, VH CDR3, VL CDR1, VL CDR2, VL CDR3, VH framework and VL framework wherein the antibody comprises a VL framework with at least about 90% sequence identity to the VL framework of the SEQ ID NO: 13-28 VL. In one embodiment, an antibody described herein comprises a VH CDR1, VH CDR2, VH CDR3, VL CDR1, VL CDR2, VL CDR3, VH framework and VL framework wherein the antibody comprises a VL framework with at least about 90% sequence identity to the VL framework of the ePGDM-E VL (SEQ ID NO: 17), ePGDM-I VL (SEQ ID NO: 21), or ePGDM-M VL (SEQ ID NO: 25). In one embodiment, an antibody described herein comprises a VH CDR1, VH CDR2, VH CDR3, VL CDR1, VL CDR2, VL CDR3, VH framework and VL framework wherein the antibody comprises (i) a VH framework with at least about 90% sequence identity to the VH framework of the ePGDM-G VH (SEQ ID NO: 9) and (ii) a VL framework with at least about 90% sequence identity to the VL framework of the ePGDM-E VL (SEQ ID NO: 17), ePGDM-I VL (SEQ ID NO: 21), or ePGDM-M VL (SEQ ID NO: 25). In one embodiment, an antibody described herein comprises a VH CDR1, VH CDR2, VH CDR3, VL CDR1, VL CDR2, VL CDR3, VH framework and VL framework wherein the antibody comprises (i) a VH framework with at least about 90% sequence identity to the VH framework of SEQ ID NO: 3-12 and (ii) a VL framework with at least about 90% sequence identity to the VL framework of SEQ ID NO: 13-28. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH comprising an amino acid sequence with at least about 70%, at least about 80%, at least about 90%, at least about 95%, at least about 96%, at least about 97%, at least about 98%, or at least about 99% sequence identity to SEQ ID NO: 3-12. In one embodiment, an antibody described herein comprises a VH comprising an amino acid sequence with at least about 90% sequence identity to SEQ ID NO: 9. In one embodiment, an antibody described herein comprises a VH comprising an amino acid sequence with at least about 70%, at least about 80%, at least about 90%, at least about 95%, at least about 96%, at least about 97%, at least about 98%, or at least about 99% sequence identity to SEQ ID NO: 1. In one embodiment, an antibody described herein comprises a VH comprising an amino acid sequence with at least about 90% sequence identity to SEQ ID NO: 3-12. In one embodiment, an antibody described herein comprises a VH comprising an amino acid sequence with at least about 90% sequence identity to SEQ ID NO: 9. In one embodiment, an antibody described herein comprises a VH comprising an amino acid sequence with at least about 90% sequence identity to SEQ ID NO: 1. In one embodiment, the antibody comprises a VH framework comprising one or more, two or more, three or more, four or more, five or more, six or more, seven or more, eight or more, nine or more, or ten or more of A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, the antibody comprises a VH framework comprising a A at H2, Q at H3, V at H5, A at H9, A at H16, N at H24, Q at H39, E at H46, E at H56, A at H58, K at H60, QGR at H62-H64, D at H66, G at H81, and E at H85, wherein the VH framework residues are numbered according to Kabat. In one embodiment, an antibody described herein comprises VH framework regions comprising one or more, two or more, three or more, four or more, or five or more of A at H2, Q at H3, V at H5, N at H24, Q at H39, and E at H85, wherein the VH framework residues are numbered according to Kabat. In one embodiment, an antibody described herein comprises VH framework regions comprising A at H2, Q at H3, V at H5, N at H24, Q at H39, and E at H85, wherein the VH framework residues are numbered according to Kabat. In one embodiment, an antibody described herein comprises VH framework regions comprising one or more, two or more, or three or more of Q at H3, V at H5, N at H24, E at H85, wherein the VH framework residues are numbered according to Kabat. In one embodiment, an antibody described herein comprises VH framework regions comprising Q at H3, V at H5, N at H24, E at H85, wherein the VH framework residues are numbered according to Kabat. In one embodiment, the VH framework further comprises QGR at H62-H64. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VL comprising an amino acid sequence with at least about 70%, at least about 80%, at least about 90%, at least about 95%, at least about 96%, at least about 97%, at least about 98%, or at least about 99% sequence identity to SEQ ID NO: 13-28. In one embodiment, an antibody described herein comprises a VL comprising an amino acid sequence with at least about 90% sequence identity to SEQ ID NO: 13-28. In one embodiment, an antibody described herein comprises a VL comprising an amino acid sequence with at least about 70%, at least about 80%, at least about 90%, at least about 95%, at least about 96%, at least about 97%, at least about 98%, or at least about 99% sequence identity to SEQ ID NO: 17. In one embodiment, an antibody described herein comprises a VL comprising an amino acid sequence with at least about 90% sequence identity to SEQ ID NO: 17. In one embodiment, an antibody described herein comprises a VL comprising an amino acid sequence with at least about 70%, at least about 80%, at least about 90%, at least about 95%, at least about 96%, at least about 97%, at least about 98%, or at least about 99% sequence identity to SEQ ID NO: 216. In one embodiment, an antibody described herein comprises a VL comprising an amino acid sequence with at least about 90% sequence identity to SEQ ID NO: 21. In one embodiment, an antibody described herein comprises a VL comprising an amino acid sequence with at least about 70%, at least about 80%, at least about 90%, at least about 95%, at least about 96%, at least about 97%, at least about 98%, or at least about 99% sequence identity to SEQ ID NO: 25. In one embodiment, an antibody described herein comprises a VL comprising an amino acid sequence with at least about 90% sequence identity to SEQ ID NO: 25. In one embodiment, an antibody described herein comprises a VL comprising an amino acid sequence with at least about 70%, at least about 80%, at least about 90%, at least about 95%, at least about 96%, at least about 97%, at least about 98%, or at least about 99% sequence identity to SEQ ID NO: 2. In one embodiment, an antibody described herein comprises a VL comprising an amino acid sequence with at least about 90% sequence identity to SEQ ID NO: 2. In one embodiment, the antibody comprises a VL framework comprising one or more, two or more, three or more, four or more, or five or more of a a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, the antibody comprises a VL framework comprising a I at L2, L at L9, P at L18, D at L26, L at L37, K or Q at L42, L at L48, D at L49, E or D at L53, E or R at L68, S at L74, D at L76, and A at L80, wherein the VL framework residues are numbered according to Kabat. In one embodiment, the antibody comprises a VL framework comprising a D at L49, E or D at L53, and E or R at L68, wherein the VL framework residues are numbered according to Kabat. In one embodiment, an antibody described herein comprises VL framework regions comprising one or more, two or more, three or more, four or more, or five or more of a I at L2, L at L9, D at L26, E at L53, R at L68, D at L76, and A at L80, wherein the VL framework residues are numbered according to Kabat. In one embodiment, an antibody described herein comprises VL framework regions comprising I at L2, L at L9, D at L26, E at L53, R at L68, D at L76, and A at L80, wherein the VL framework residues are numbered according to Kabat. In one embodiment, an antibody described herein comprises VL framework regions comprising one or more, two or more, three or more, four or more, or five or more of L at L9, E at L53, R at L68, S at L74, D at L76, and A at L80, wherein the VL framework residues are numbered according to Kabat. In one embodiment, an antibody described herein comprises VL framework regions comprising L at L9, E at L53, R at L68, S at L74, D at L76, and A at L80, wherein the VL framework residues are numbered according to Kabat. In one embodiment, an antibody described herein comprises VL framework regions comprising one or more, two or more, three or more, or four or more of I at L2, L at L9, L at L48, E at L53, E at L68, wherein the VL framework residues are numbered according to Kabat. In one embodiment, an antibody described herein comprises VL framework regions comprising I at L2, L at L9, L at L48, E at L53, E at L68, wherein the VL framework residues are numbered according to Kabat. In one embodiment, an antibody described herein comprises VL framework regions comprising one or more, or two or more of D at L49, E or D at L53, E or R at L68, wherein the VL framework residues are numbered according to Kabat. In one embodiment, an antibody described herein comprises VL framework regions comprising D at L49, E or D at L53, E or R at L68, wherein the VL framework residues are numbered according to Kabat. In one embodiment, the VH framework further comprises K at H105. In one embodiment, the VH framework further comprises Q at H3, V at H5, N at H24, and E at H85. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises (i) a VH comprising an amino acid sequence with at least about 70%, at least about 80%, at least about 90%, at least about 95%, at least about 96%, at least about 97%, at least about 98%, or at least about 99% sequence identity to SEQ ID NO: 1 or 3-12 and (ii) a VL comprising an amino acid sequence with at least about 70%, at least about 80%, at least about 90%, at least about 95%, at least about 96%, at least about 97%, at least about 98%, or at least about 99% sequence identity to SEQ ID NO: 2 or 13-28. In one embodiment, an antibody described herein comprises (i) a VH comprising an amino acid sequence with at least about 90% sequence identity to SEQ ID NO: 1 or 3-12 and (ii) a VL comprising an amino acid sequence with at least about 90% sequence identity to SEQ ID NO: 2 or 13-28. In one embodiment, an antibody described herein comprises (i) a VH comprising an amino acid sequence with at least about 70%, at least about 80%, at least about 90%, at least about 95%, at least about 96%, at least about 97%, at least about 98%, or at least about 99% sequence identity to SEQ ID NO: 9 and (ii) a VL comprising an amino acid sequence with at least about 70%, at least about 80%, at least about 90%, at least about 95%, at least about 96%, at least about 97%, at least about 98%, or at least about 99% sequence identity to SEQ ID NO: 17, 21, or 25. In one embodiment, an antibody described herein comprises (i) a VH comprising an amino acid sequence with at least about 90% sequence identity to SEQ ID NO: 9 and (ii) a VL comprising an amino acid sequence with at least about 90% sequence identity to SEQ ID NO: 17. In one embodiment, an antibody described herein comprises (i) a VH comprising an amino acid sequence with at least about 90% sequence identity to SEQ ID NO: 9 and (ii) a VL comprising an amino acid sequence with at least about 90% sequence identity to SEQ ID NO: 21. In one embodiment, an antibody described herein comprises (i) a VH comprising an amino acid sequence with at least about 90% sequence identity to SEQ ID NO: 9 and (ii) a VL comprising an amino acid sequence with at least about 90% sequence identity to SEQ ID NO: 25. In one embodiment, the antibody comprises a VH framework and VL framework comprising one or more, two or more, three or more, four or more, five or more, six or more, seven or more, eight or more, nine or more, or ten or more of a A at H2, Q at H3, V at H5, A at H9, A at H16, N at H24, Q at H39, E at H46, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80, wherein the VH and VL framework residues are numbered according to Kabat. In one embodiment, the antibody comprises a VH framework and VL framework comprising a A at H2, Q at H3, V at H5, A at H9, A at H16, N at H24, Q at H39, E at H46, A at H58, K at H60, QGR at H62-H64, D at H66, G at H81, E at H85, a I at L2, L at L9, P at L18, D at L26, L at L37, K or Q at L42, L at L48, D at L49, E or D at L53, E or R at L68, S at L74, D at L76, and A at L80, wherein the VH and VL framework residues are numbered according to Kabat. In one embodiment, the VH and VL framework regions comprise one or more, two or more, three or more, four or more, or five or more of A at H2, Q at H3, V at H5, N at H24, Q at H39, E at H85, I at L2, L at L9, D at L26, E at L53, R at L68, D at L76, and A at L80, wherein the VH and VL framework residues are numbered according to Kabat. In one embodiment, the VH and VL framework regions comprise A at H2, Q at H3, V at H5, N at H24, Q at H39, E at H85, I at L2, L at L9, D at L26, E at L53, R at L68, D at L76, and A at L80, wherein the VH and VL framework residues are numbered according to Kabat. In one embodiment, the VH and VL framework regions comprise one or more, two or more, three or more, four or more, or five or more of A at H2, Q at H3, V at H5, N at H24, Q at H39, E at H85, L at L9, E at L53, R at L68, S at L74, D at L76, and A at L80, wherein the VH and VL framework residues are numbered according to Kabat. In one embodiment, the VH and VL framework regions comprise A at H2, Q at H3, V at H5, N at H24, Q at H39, E at H85, L at L9, E at L53, R at L68, S at L74, D at L76, and A at L80, wherein the VH and VL framework residues are numbered according to Kabat. In one embodiment, the VH and VL framework regions comprise one or more, two or more, three or more, four or more, or five or more of A at H2, Q at H3, V at H5, N at H24, Q at H39, E at H85, I at L2, L at L9, L at L48, E at L53, E at L68, wherein the VH and VL framework residues are numbered according to Kabat. In one embodiment, the VH and VL framework regions comprise A at H2, Q at H3, V at H5, N at H24, Q at H39, E at H85, I at L2, L at L9, L at L48, E at L53, E at L68, wherein the VH and VL framework residues are numbered according to Kabat. In one embodiment, the VH and VL framework regions comprise one or more, two or more, three or more, four or more, or five or more of Q at H3, V at H5, N at H24, E at H85, D at L49, E or D at L53, E or R at L68, wherein the VH and VL framework residues are numbered according to Kabat. In one embodiment, the VH and VL framework regions comprise Q at H3, V at H5, N at H24, E at H85, D at L49, E or D at L53, E or R at L68, wherein the VH and VL framework residues are numbered according to Kabat. In one embodiment, the VH framework further comprises QGR at H62-H64. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody disclosed herein comprises a VH having at least about 70%, at least about 75%, at least about 80%, or at least about 90% sequence identity to SEQ ID NO: 1 and a VL having at least about 70%, at least about 75%, at least about 80%, or at least about 90% sequence identity SEQ ID NO: 2, wherein the VH comprises one or more of A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104, wherein the VH residues are numbered according to Kabat. In one embodiment, the VH comprises two or more, three or more, four or more, or five or more of a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104. In one embodiment, the VH region comprises one or more, two or more, three or more, four or more, or five or more of A at H2, Q at H3, V at H5, N at H24, T at H30, Q at H39, E at H85, E at H100H, A at H104, wherein the VH framework residues are numbered according to Kabat. In one embodiment, the VH region comprises A at H2, Q at H3, V at H5, N at H24, T at H30, Q at H39, E at H85, E at H100H, A at H104, wherein the VH framework residues are numbered according to Kabat. In one embodiment, the VH region comprises one or more, two or more, three or more, four or more, or five or more of Q at H3, V at H5, N at H24, T at H30, E at H85, A at H104, wherein the VH framework residues are numbered according to Kabat. In one embodiment, the VH region comprises Q at H3, V at H5, N at H24, T at H30, E at H85, A at H104, wherein the VH framework residues are numbered according to Kabat. In one embodiment, the VL comprises one or more of a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80, wherein the VL residues are numbered according to Kabat. In one embodiment, the VL comprises two or more, three or more, four or more, or five or more of a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80. In one embodiment, the VL region comprises one or more, two or more, three or more, four or more, or five or more of I at L2, L at L9, D at L26, Q at L27C, E at L53, R at L68, D at L76, and A at L80, wherein the VH framework residues are numbered according to Kabat. In one embodiment, the VL region comprises I at L2, L at L9, D at L26, Q at L27C, E at L53, R at L68, D at L76, and A at L80, wherein the VH framework residues are numbered according to Kabat. In one embodiment, the VL region comprises one or more, two or more, three or more, four or more, or five or more of L at L9, Q at L27, E at L53, R at L68, S at L74, D at L76, and A at L80, wherein the VH framework residues are numbered according to Kabat. In one embodiment, the VL region comprises L at L9, Q at L27, E at L53, R at L68, S at L74, D at L76, and A at L80, wherein the VH framework residues are numbered according to Kabat. In one embodiment, the VL region comprises one or more, two or more, three or more, four or more, or five or more of I at L2, L at L9, Q at L27C, L at L48, E at L53, E at L68, wherein the VH framework residues are numbered according to Kabat. In one embodiment, the VL region comprises I at L2, L at L9, Q at L27C, L at L48, E at L53, E at L68, wherein the VH framework residues are numbered according to Kabat. In one embodiment, the VL region comprises one or more, or two or more of D at L49, E or D at L53, E or R at L68, wherein the VH framework residues are numbered according to Kabat. In one embodiment, the VL region comprises D at L49, E or D at L53, E or R at L68, wherein the VH framework residues are numbered according to Kabat. In one embodiment, the VH CDR1, VH CDR2, VH CDR3, VL CDR1, VL CDR2, and VL CDR3 comprises the sequence of SEQ ID NO: 94-99, respectively. In one embodiment, the VH CDR1, VH CDR2, VH CDR3, VL CDR1, VL CDR2, and VL CDR3 comprises the sequence of SEQ ID NO: 37, 38, 34, 44, 45, and 30, respectively. In one embodiment, the VH CDR1, VH CDR2, VH CDR3, VL CDR1, VL CDR2, and VL CDR3 comprises the sequence of SEQ ID NO: 37, 38, 34, 43, 45, and 30, respectively. In one embodiment, the antibody comprises the PGDM1400 VH CDR1, VH CDR2, VH CDR3, VL CDR1, VL CDR2, and VL CDR3. In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-E VL (SEQ ID NO: 17). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-I VL (SEQ ID NO: 21). In one embodiment, the antibody comprises the VH CDR1, VH CDR2, and VH CDR3 of the ePGDM-G VH (SEQ ID NO: 9) and the VL CDR1, VL CDR2, and VL CDR3 of the ePGDM-M VL (SEQ ID NO: 25). In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein comprises a VH of SEQ ID NO: 3-12. In one embodiment, an antibody described herein comprises a VH of SEQ ID NO: 9. In one embodiment, an antibody described herein comprises a VL of SEQ ID NO: 13-28. In one embodiment, an antibody described herein comprises a VL of SEQ ID NO: 17. In one embodiment, an antibody described herein comprises a VL of SEQ ID NO: 21. In one embodiment, an antibody described herein comprises a VL of SEQ ID NO: 25. In one embodiment, an antibody described herein comprises (i) a VH of SEQ ID NO: 3-12 and (ii) a VL of SEQ ID NO: 13-28. In one embodiment, an antibody described herein comprises (i) a VH of SEQ ID NO: 1 and (ii) a VL of SEQ ID NO: 13-28. In one embodiment, an antibody described herein comprises (i) a VH of SEQ ID NO: 3-12 and (ii) a VL of SEQ ID NO: 2. In one embodiment, an antibody described herein comprises (i) a VH of SEQ ID NO: 9 and (ii) a VL of SEQ ID NO: 17. In one embodiment, an antibody described herein comprises (i) a VH of SEQ ID NO: 9 and (ii) a VL of SEQ ID NO: 21. In one embodiment, an antibody described herein comprises (i) a VH of SEQ ID NO: 9 and (ii) a VL of SEQ ID NO: 25. In one embodiment, the antibody is capable of neutralizing BG505. In one embodiment, the antibody is capable of neutralizing at least two cross-clade isolates of HIV. In one embodiment, the antibody specifically binds to HIV Env (e.g., BG505 SOSIP).

In one embodiment, an antibody described herein is a recombinant antibody, a chimeric antibody, a bispecific antibody, a trispecific antibody, or a multispecific antibody. In one embodiment, the antibody fragment comprises a single-chain Fv (scFv), F(ab) fragment, F(ab')2 fragment, or an isolated VH domain.

In some embodiments, an antibody described herein is a multispecific antibody, e.g. a bispecific antibody. Multispecific antibodies are monoclonal antibodies that have binding specificities for at least two different sites. In some embodiments, one of the binding specificities is for HIV Env and the other is for any other antigen. In some embodiments, bispecific antibodies bind to two different epitopes of HIV Env. Bispecific antibodies can be prepared as full length antibodies or antibody fragments.

Techniques for making multispecific antibodies, e.g., bispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991). Engineered antibodies with three or more functional antigen binding sites, including "Octopus antibodies" and dual variable domain (DVD) immunoglobulins are also included herein (see, e.g. US 2006/0025576A1 and U.S. Pat. No. 10,093,733). The antibody or fragment disclosed herein also includes a "Dual Acting Fab" or "DAF" comprising an antigen binding site that binds to different epitopes, e.g., two different HIV Env epitopes (see, US 2008/0069820, for example).

In some embodiments, an antibody described herein is a multispecific antibody, e.g. a bispecific antibody comprising a first antigen binding domain comprising a VH domain or VH and VL domains disclosed herein, and a second antigen binding region capable of binding an HIV Env epitope. In one embodiment, the second antigen binding region binds to an HIV Env epitope region different from the HIV Env epitope region bound by an antibody disclosed herein. In one embodiment, the second antigen binding region binds to the CD4 binding site (CD4bs) epitope region, the N332 glycan epitope region near the V3 loop, the gp120-gp41 interface epitope region, or the gp41 membrane proximal external epitope region (MPER). In one embodiment, the second antigen binding region binds to the CD4 binding site (CD4bs) epitope region, V1/V2-glycan site (V2g) epitope region, the N332 glycan epitope region near the V3 loop, the gp120-gp41 interface epitope region, or the gp41 membrane proximal external epitope region (MPER). In one embodiment, the second antigen binding region binds to the CD4 binding site (CD4bs) epitope region. In one embodiment, the second antigen binding region binds to the V1/V2-glycan site (V2g) epitope region. In one embodiment, the second antigen binding region binds to the N332 glycan epitope region near the V3 loop. In one embodiment, the second antigen binding region binds to the gp120-gp41 interface epitope region. In one embodiment, the second antigen binding region binds to the gp41 membrane proximal external epitope region (MPER).

In one embodiment, an antibody described herein comprises a heavy and/or light chain constant region. In one embodiment, an antibody described herein comprises a human heavy and/or light chain constant region. In one embodiment, the heavy chain constant region is human immunoglobulin IgG1, IgG2, IgG3, IgG4, IgA1, or IgA2 constant region. In one embodiment, the heavy chain constant region is human immunoglobulin IgG1 constant region. In one embodiment, the heavy chain constant region comprises a native amino acid sequence. In one embodiment, the heavy chain constant region comprises the amino acid sequence of SEQ ID NO: 108. In one embodiment, the heavy chain constant region comprises a variant amino acid sequence. In one embodiment, the heavy chain constant region comprises the amino acid sequence of SEQ ID NO: 109.

In one embodiment, the antibody disclosed herein is not PGDM1400. In one embodiment, the antibody disclosed herein comprises VH CDR1, VH CDR2, VH CDR3, VL CDR1, VL CDR2, and VL CDR3, wherein one or more of the VH CDR1, VH CDR2, VH CDR3, VL CDR1, VL CDR2, and VL CDR3 does not comprise the amino acid sequence of the corresponding PGDM1400 CDR. In one embodiment, the antibody disclosed herein comprises a VH and a VL, wherein one or both of the VH and VL do not comprise the amino acid sequence of the corresponding PGDM1400 VH and VL.

In one embodiment, an antibody disclosed herein is capable of neutralizing at least 5, at least 6, at least 7 or 8 of the cross-clade HIV isolates in the 8-member indicator virus panel. In one embodiment, an antibody disclosed herein is capable of neutralizing at least 7 of the cross-clade HIV isolates in the 8-member indicator virus panel. In one embodiment, an antibody disclosed herein is capable of neutralizing at least 20, at least 25, at least 27, at least 28, at least 29 or 30 of the cross-clade HIV isolates in the 30-member indicator virus panel. In one embodiment, an antibody disclosed herein is capable of neutralizing at least 25 of the cross-clade HIV isolates in the 30-member indicator virus panel. In one embodiment, an antibody disclosed herein is capable of neutralizing at least about 50%, at least about 60%, at least about 70%, at least about 80%, at least about 90%, or 100% of cross-clade HIV isolates in the 116-member indicator virus panel. In one embodiment, an antibody disclosed herein is capable of neutralizing at least about 50%, of cross-clade HIV isolates in the 116-member indicator virus panel. In one embodiment, an antibody disclosed herein is capable of neutralizing at least about 60%, of cross-clade HIV isolates in the 116-member indicator virus panel. In one embodiment, an antibody disclosed herein is capable of neutralizing at least about 62%, of cross-clade HIV isolates in the 116-member indicator virus panel. In one embodiment, an antibody disclosed herein is capable of neutralizing at least about 65%, of cross-clade HIV isolates in the 116-member indicator virus panel. In one embodiment, an antibody disclosed herein is capable of neutralizing at least about 67%, of cross-clade HIV isolates in the 116-member indicator virus panel. In one embodiment, an antibody disclosed herein is capable of neutralizing at least about 68%, of cross-clade HIV isolates in the 116-member indicator virus panel. In one embodiment, an antibody disclosed herein is capable of neutralizing at least about 69%, of cross-clade HIV isolates in the 116-member indicator virus panel. In one embodiment, an antibody disclosed herein is capable of neutralizing at least about 70% of cross-clade HIV isolates in the 116-member indicator virus panel. In one embodiment, an antibody disclosed herein is capable of neutralizing at least about 71% of cross-clade HIV isolates in the 116-member indicator virus panel. In one embodiment, an antibody disclosed herein is capable of neutralizing at least about 72% of cross-clade HIV isolates in the 116-member indicator virus panel. In one embodiment, an antibody disclosed herein is capable of neutralizing at least about 73% of cross-clade HIV isolates in the 116-member indicator virus panel. In one embodiment, an antibody disclosed herein is capable of neutralizing at least about 74% of cross-clade HIV isolates in the 116-member indicator virus panel. In one embodiment, an antibody disclosed herein is capable of neutralizing at least about 75% of cross-clade HIV isolates in the 116-member indicator virus panel. In one embodiment, an antibody disclosed herein is capable of neutralizing at least about 77% of cross-clade HIV isolates in the 116-member indicator virus panel. In one embodiment, an antibody disclosed herein is capable of neutralizing at least about 80% of cross-clade HIV isolates in the 116-member indicator virus panel. In one embodiment, an antibody disclosed herein is capable of neutralizing at least about 85% of cross-clade HIV isolates in the 116-member indicator virus panel In one embodiment, an antibody disclosed herein is capable of neutralizing the cross-clade HIV isolates with a median IC50 equal to or less than about 0.1 μg/ml, about 0.05 μg/ml, about 0.025 μg/ml, about 0.01 μg/ml, or about 0.005 μg/ml. In one embodiment, an antibody disclosed herein is capable of neutralizing the cross-clade HIV isolates with a median IC50 equal to or less than about 0.05 μg/ml. In one embodiment, an antibody disclosed herein is capable of neutralizing the cross-clade HIV isolates of the 116-member indicator virus panel with a median IC50 equal to or less than about 0.05 μg/ml. In one embodiment, an antibody disclosed herein is capable of neutralizing the cross-clade HIV isolates of the 116-member indicator virus panel with a median IC50 equal to or less than about 0.03 μg/ml. In one embodiment, an antibody disclosed herein is capable of neutralizing the cross-clade HIV isolates of the 116-member indicator virus panel with a median IC50 equal to or less than about 0.02 μg/ml. In one embodiment, an antibody disclosed herein is capable of neutralizing the cross-clade HIV isolates of the 116-member indicator virus panel with a median IC50 equal to or less than about 0.01 μg/ml. In one embodiment, an antibody disclosed herein is capable of neutralizing the cross-clade HIV isolates of the 116-member indicator virus panel with a median IC50 equal to or less than about 0.009 μg/ml. In one embodiment, an antibody disclosed herein is capable of neutralizing the cross-clade HIV isolates of the 116-member indicator virus panel with a median IC50 equal to or less than about 0.008 μg/ml. In one embodiment, an antibody disclosed herein is capable of neutralizing the cross-clade HIV isolates of the 116-member indicator virus panel with a median IC50 equal to or less than about 0.007 μg/ml. In one embodiment, an antibody disclosed herein is capable of neutralizing the cross-clade HIV isolates of the 116-member indicator virus panel with a median IC50 equal to or less than about 0.006 μg/ml. In one embodiment, an antibody disclosed herein is capable of neutralizing the cross-clade HIV isolates of the 116-member indicator virus panel with a median IC50 equal to or less than about 0.005 μg/ml. In one embodiment, an antibody disclosed herein is capable of neutralizing the cross-clade HIV isolates of the 116-member indicator virus panel with a median IC50 equal to or less than about 0.004 μg/ml. In one embodiment, an antibody disclosed herein is capable of neutralizing the cross-clade HIV isolates of the 116-member indicator virus panel with a median IC50 equal to or less than about 0.003 μg/ml. In one embodiment, an antibody disclosed herein is capable of neutralizing the cross-clade HIV isolates of the 116-member indicator virus panel with a median IC50 equal to or less than about 0.002 μg/ml. In one embodiment, an antibody disclosed herein is capable of neutralizing the cross-clade HIV isolates of the 116-member indicator virus panel with a median IC50 equal to or less than about 0.001 μg/ml. In one embodiment, an antibody disclosed herein is capable of neutralizing at least about 50%, 60%, 70%, 80%, 90%, 95%, or 100% of cross-clade HIV isolates in the 116-member indicator virus panel with a median $IC_{50}$ equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing at least about 70% of cross-clade HIV isolates in the 116-member indicator virus panel with a median $IC_{50}$ equal to or less than 0.05 μg/ml. In one embodiment, an antibody disclosed herein is capable of neutralizing at least about 70% of cross-clade HIV isolates in the 116-member indicator virus panel with a median $IC_{50}$ equal to or less than 0.01 μg/ml. In one embodiment, an antibody disclosed herein is capable of neutralizing at least about 70% of cross-clade HIV isolates in the 116-member indicator virus panel with a median $IC_{50}$ equal to or less than 0.005 μg/ml. In one embodiment, an antibody disclosed herein is capable of neutralizing at least about 70% of cross-clade HIV isolates in the 116-member indicator virus panel with a median $IC_{50}$ equal to or less than 0.001 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC50 equal to or less than about 0.1 g/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC50 equal to or less than 0.05 g/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC50 equal to or less than 0.01 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC50 equal to or less than 0.005 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC50 equal to or less than 0.001 μg/ml. In one embodiment, an antibody disclosed herein is capable of neutralizing the clade A HIV isolates in the 116-member indicator virus panel with a median IC50 equal to or less than about 0.1 μg/ml, 0.07 μg/ml, 0.06 μg/ml, 0.05 μg/ml, 0.025 g/ml, 0.01 μg/ml or 0.005 μg/ml. In one embodiment, an antibody disclosed herein is capable of neutralizing the clade A HIV isolates in the 116-member indicator virus panel with a median IC50 equal to or less than 0.05 μg/ml. In one embodiment, an antibody disclosed herein is capable of neutralizing the clade A HIV isolates in the 116-member indicator virus panel with a median IC50 equal to or less than 0.01 μg/ml. In one embodiment, an antibody disclosed herein is capable of neutralizing the clade A HIV isolates in the 116-member indicator virus panel with a median IC50 equal to or less than 0.005 μg/ml. In one embodiment, an antibody disclosed herein is capable of neutralizing the clade A HIV isolates in the 116-member indicator virus panel with a median IC50 equal to or less than 0.001 μg/ml. In one embodiment, an antibody disclosed herein is capable of neutralizing the clade B HIV isolates in the 116-member indicator virus panel with a median IC50 equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing the clade B HIV isolates in the 116-member indicator virus panel with a median IC50 equal to or less than 0.05 μg/ml. In one embodiment, an antibody disclosed herein is capable of neutralizing the clade B HIV isolates in the 116-member indicator virus panel with a median IC50 equal to or less than 0.01 μg/ml. In one embodiment, an antibody disclosed herein is capable of neutralizing the clade B HIV isolates in the 116-member indicator virus panel with a median IC50 equal to or less than 0.005 μg/ml. In one embodiment, an antibody disclosed herein is capable of neutralizing the clade B HIV isolates in the 116-member indicator virus panel with a median IC50 equal to or less than 0.001 μg/ml. In one embodiment, an antibody disclosed herein is capable of neutralizing the clade C HIV isolates in the 116-member indicator virus panel with a median IC50 equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing the clade C HIV isolates in the 116-member indicator virus panel with a median IC50 equal to or less than 0.05 μg/ml. In one embodiment, an antibody disclosed herein is capable of neutralizing the clade C HIV isolates in the 116-member indicator virus panel with a median IC50 equal to or less than 0.01 μg/ml. In one embodiment, an antibody disclosed herein is capable of neutralizing the clade C HIV isolates in the 116-member indicator virus panel with a median IC50 equal to or less than 0.005 μg/ml. In one embodiment, an antibody disclosed herein is capable of neutralizing the clade C HIV isolates in the 116-member indicator virus panel with a median IC50 equal to or less than 0.001 μg/ml. In one embodiment, an antibody disclosed herein is capable of neutralizing the cross-clade HIV isolates with a median IC80 equal to or less than about 0.1 μg/ml, about 0.05 μg/ml, about 0.025 g/ml, about 0.01 μg/ml, or about 0.005 μg/ml. In one embodiment, an antibody disclosed herein is capable of neutralizing the cross-clade HIV isolates with a median IC80 equal to or less than about 0.05 μg/ml. In one embodiment, an antibody disclosed herein is capable of neutralizing the cross-clade HIV isolates of the 116-member indicator virus panel with a median IC80 equal to or less than about 0.05 μg/ml. In one embodiment, an antibody disclosed herein is capable of neutralizing the cross-clade HIV isolates of the 116-member indicator virus panel with a median IC80 equal to or less than about 0.03 μg/ml. In one embodiment, an antibody disclosed herein is capable of neutralizing the cross-clade HIV isolates of the 116-member indicator virus panel with a median IC80 equal to or less than about 0.02 μg/ml. In one embodiment, an antibody disclosed herein is capable of neutralizing the cross-clade HIV isolates of the 116-member indicator virus panel with a median IC80 equal to or less than about 0.01 μg/ml. In one embodiment, an antibody disclosed herein is capable of neutralizing the cross-clade HIV isolates of the 116-member indicator virus panel with a median IC80 equal to or less than about 0.009 μg/ml. In one embodiment, an antibody disclosed herein is capable of neutralizing the cross-clade HIV isolates of the 116-member indicator virus panel with a median IC80 equal to or less than about 0.008 μg/ml. In one embodiment, an antibody disclosed herein is capable of neutralizing the cross-clade HIV isolates of the 116-member indicator virus panel with a median IC80 equal to or less than about 0.007 g/ml. In one embodiment, an antibody disclosed herein is capable of neutralizing the cross-clade HIV isolates of the 116-member indicator virus panel with a median IC80 equal to or less than about 0.006 μg/ml. In one embodiment, an antibody disclosed herein is capable of neutralizing the cross-clade HIV isolates of the 116-member indicator virus panel with a median IC80 equal to or less than about 0.005 μg/ml. In one embodiment, an antibody disclosed herein is capable of neutralizing the cross-clade HIV isolates of the 116-member indicator virus panel with a median IC80 equal to or less than about 0.004 μg/ml. In one embodiment, an antibody disclosed herein is capable of neutralizing the cross-clade HIV isolates of the 116-member indicator virus panel with a median IC80 equal to or less than about 0.003 μg/ml. In one embodiment, an antibody disclosed herein is capable of neutralizing the cross-clade HIV isolates of the 116-member indicator virus panel with a median IC80 equal to or less than about 0.002 μg/ml. In one embodiment, an antibody disclosed herein is capable of neutralizing the cross-clade HIV isolates of the 116-member indicator virus panel with a median IC80 equal to or less than about 0.001 μg/ml. In one embodiment, an antibody disclosed herein is capable of neutralizing at least about 50%, 60%, 70%, 80%, 90%, 95%, or 100% of cross-clade HIV isolates in the 116-member indicator virus panel with a median IC80 equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing at least about 70% of cross-clade HIV isolates in the 116-member indicator virus panel with a median IC80 equal to or less than 0.05 μg/ml. In one embodiment, an antibody disclosed herein is capable of neutralizing at least about 70% of cross-clade HIV isolates in the 116-member indicator virus panel with a median IC80 equal to or less than 0.01 μg/ml. In one embodiment, an antibody disclosed herein is capable of neutralizing at least about 70% of cross-clade HIV isolates in the 116-member indicator virus panel with a median IC80 equal to or less than 0.005 μg/ml. In one embodiment, an antibody disclosed herein is capable of neutralizing at least about 70% of cross-clade HIV isolates in the 116-member indicator virus panel with a median IC80 equal to or less than 0.001 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC80 equal to or less than about 0.1 g/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC80 equal to or less than 0.05 g/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC80 equal to or less than 0.01 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC80 equal to or less than 0.005 μg/ml. In one embodiment, an antibody disclosed herein is capable of neutralizing the clade A, A (T/F), AC, ACD, B, B (T/F), BC, C, C (T/F), CD, CRF01_AE, CRF01_AE (T/F), CRF02_AG, D, or G HIV isolates in the 116-member indicator virus panel with a median IC80 equal to or less than 0.001 μg/ml. In one embodiment, an antibody disclosed herein is capable of neutralizing the clade A HIV isolates in the 116-member indicator virus panel with a median IC80 equal to or less than about 0.1 μg/ml, 0.07 μg/ml, 0.06 μg/ml, 0.05 μg/ml, 0.025 g/ml, 0.01 μg/ml or 0.005 μg/ml. In one embodiment, an antibody disclosed herein is capable of neutralizing the clade A HIV isolates in the 116-member indicator virus panel with a median IC80 equal to or less than 0.05 μg/ml. In one embodiment, an antibody disclosed herein is capable of neutralizing the clade A HIV isolates in the 116-member indicator virus panel with a median IC80 equal to or less than 0.01 μg/ml. In one embodiment, an antibody disclosed herein is capable of neutralizing the clade A HIV isolates in the 116-member indicator virus panel with a median IC80 equal to or less than 0.005 μg/ml. In one embodiment, an antibody disclosed herein is capable of neutralizing the clade A HIV isolates in the 116-member indicator virus panel with a median IC80 equal to or less than 0.001 μg/ml. In one embodiment, an antibody disclosed herein is capable of neutralizing the clade B HIV isolates in the 116-member indicator virus panel with a median IC80 equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing the clade B HIV isolates in the 116-member indicator virus panel with a median IC80 equal to or less than 0.05 μg/ml. In one embodiment, an antibody disclosed herein is capable of neutralizing the clade B HIV isolates in the 116-member indicator virus panel with a median IC80 equal to or less than 0.01 μg/ml. In one embodiment, an antibody disclosed herein is capable of neutralizing the clade B HIV isolates in the 116-member indicator virus panel with a median IC80 equal to or less than 0.005 μg/ml. In one embodiment, an antibody disclosed herein is capable of neutralizing the clade B HIV isolates in the 116-member indicator virus panel with a median IC80 equal to or less than 0.001 μg/ml. In one embodiment, an antibody disclosed herein is capable of neutralizing the clade C HIV isolates in the 116-member indicator virus panel with a median IC80 equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing the clade C HIV isolates in the 116-member indicator virus panel with a median IC80 equal to or less than 0.05 μg/ml. In one embodiment, an antibody disclosed herein is capable of neutralizing the clade C HIV isolates in the 116-member indicator virus panel with a median IC80 equal to or less than 0.01 μg/ml. In one embodiment, an antibody disclosed herein is capable of neutralizing the clade C HIV isolates in the 116-member indicator virus panel with a median IC80 equal to or less than 0.005 μg/ml. In one embodiment, an antibody disclosed herein is capable of neutralizing the clade C HIV isolates in the 116-member indicator virus panel with a median IC80 equal to or less than 0.001 μg/ml.

In one embodiment, an antibody disclosed herein is capable of neutralizing a PGDM1400 resistant HIV isolate. In one embodiment, an antibody disclosed herein is capable of neutralizing at least 2, at least 3, at least 4, or at least 5 PGDM1400 resistant HIV isolates. In one embodiment, an antibody disclosed herein is capable of neutralizing at least 2 cross-clade PGDM1400 resistant HIV isolates. In one embodiment, an antibody disclosed herein is capable of neutralizing at least 2, at least 3, at least 4, or at least 5 PGDM1400 resistant HIV isolates. In one embodiment, an antibody disclosed herein is capable of neutralizing the PGDM1400 resistant HIV isolates with a median IC50 equal to or less than about 0.1 μg/ml, about 0.05 μg/ml, about 0.025 g/ml, about 0.01 μg/ml, or about 0.005 μg/ml. In one embodiment, an antibody disclosed herein is capable of neutralizing the PGDM1400 resistant HIV isolates with a median IC50 equal to or less than about 0.05 μg/ml. In one embodiment, an antibody disclosed herein is capable of neutralizing the PGDM1400 resistant HIV isolates with a median IC80 equal to or less than about 0.1 μg/ml, about 0.05 μg/ml, about 0.025 μg/ml, about 0.01 μg/ml, or about 0.005 μg/ml. In one embodiment, an antibody disclosed herein is capable of neutralizing the PGDM1400 resistant HIV isolates with a median IC80 equal to or less than about 0.05 μg/ml. In one embodiment, an antibody disclosed herein is capable of neutralizing at least about 25%, at least about 30%, at least about 35%, at least about 40%, at least about 45%, or at least about 50% of clade C HIV isolates in the 100-member indicator virus panel. In one embodiment, an antibody disclosed herein is capable of neutralizing at least about 25% of clade C HIV isolates in the 100-member indicator virus panel. In one embodiment, an antibody disclosed herein is capable of neutralizing at least about 30% of clade C HIV isolates in the 100-member indicator virus panel. In one embodiment, an antibody disclosed herein is capable of neutralizing at least about 35% of clade C HIV isolates in the 100-member indicator virus panel. In one embodiment, an antibody disclosed herein is capable of neutralizing at least about 40% of clade C HIV isolates in the 100-member indicator virus panel. In one embodiment, an antibody disclosed herein is capable of neutralizing at least about 45% of clade C HIV isolates in the 100-member indicator virus panel. In one embodiment, an antibody disclosed herein is capable of neutralizing at least about 50% of clade C HIV isolates in the 100-member indicator virus panel. In one embodiment, an antibody disclosed herein is capable of neutralizing the clade C HIV isolates with a median IC50 equal to or less than about 0.1 μg/ml, about 0.05 μg/ml, about 0.025 μg/ml, about 0.01 μg/ml, or about 0.005 μg/ml. In one embodiment, an antibody disclosed herein is capable of neutralizing the clade C HIV isolates with a median IC50 equal to or less than about 0.05 μg/ml. In one embodiment, an antibody disclosed herein is capable of neutralizing the clade C HIV isolates of the 100-member indicator virus panel with a median IC50 equal to or less than about 0.03 μg/ml. In one embodiment, an antibody disclosed herein is capable of neutralizing the clade C HIV isolates of the 100-member indicator virus panel with a median IC50 equal to or less than about 0.02 μg/ml. In one embodiment, an antibody disclosed herein is capable of neutralizing the clade C HIV isolates of the 100-member indicator virus panel with a median IC50 equal to or less than about 0.01 μg/ml. In one embodiment, an antibody disclosed herein is capable of neutralizing the clade C HIV isolates of the 100-member indicator virus panel with a median IC50 equal to or less than about 0.005 μg/ml. In one embodiment, an antibody disclosed herein is capable of neutralizing at least about 25%, at least about 30%, at least about 35%, at least about 40%, at least about 45%, or at least about 50% of clade C HIV isolates in the 100-member indicator virus panel with a median $IC_{50}$ equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, an antibody disclosed herein is capable of neutralizing at least about 45% of clade C HIV isolates in the 100-member indicator virus panel with a median $IC_{50}$ equal to or less than 0.05 μg/ml. In one embodiment, an antibody disclosed herein is capable of neutralizing at least about 45% of clade C HIV isolates in the 100-member indicator virus panel with a median $IC_{50}$ equal to or less than 0.01 g/ml. In one embodiment, an antibody disclosed herein is capable of neutralizing at least about 20%, at least about 25%, at least about 30%, or at least about 35% of clade C HIV isolates in the 100-member indicator virus panel with a median $IC_{50}$ equal to or less than about 0.1 μg/ml, 0.07 g/ml, 0.06 μg/ml, 0.05 μg/ml, 0.025 μg/ml, 0.01 μg/ml or 0.005 μg/ml. In one embodiment, an antibody disclosed herein is capable of neutralizing at least about 25% of clade C HIV isolates in the 100-member indicator virus panel with a median $IC_{50}$ equal to or less than 0.05 μg/ml. In one embodiment, an antibody disclosed herein is capable of neutralizing at least about 25% of clade C HIV isolates in the 100-member indicator virus panel with a median $IC_{50}$ equal to or less than 0.01 g/ml.

In one embodiment, an antibody disclosed herein is capable of neutralizing a larger fraction of the cross-clade HIV isolates in the 8-member indicator virus panel than PGDM1400. In one embodiment, an antibody disclosed herein is capable of neutralizing a larger fraction of the cross-clade HIV isolates in the 30-member indicator virus panel than PGDM1400. In one embodiment, an antibody disclosed herein is capable of neutralizing a larger fraction of the cross-clade HIV isolates in the 116-member indicator virus panel than PGDM1400. In one embodiment, an antibody disclosed herein is capable of neutralizing a larger fraction of the clade C HIV isolates in the 100-member indicator virus panel than PGDM1400.

In one embodiment, an antibody disclosed herein is capable of neutralizing cross-clade HIV isolates in the 8-member indicator virus panel with a lower median IC50 than PGDM1400. In one embodiment, an antibody disclosed herein is capable of neutralizing cross-clade HIV isolates in the 30-member indicator virus panel with a lower median IC50 than PGDM1400. In one embodiment, an antibody disclosed herein is capable of neutralizing cross-clade HIV isolates in the 116-member indicator virus panel with a lower median IC50 than PGDM1400. In one embodiment, an antibody disclosed herein is capable of neutralizing clade C HIV isolates in the 100-member indicator virus panel with a lower median IC50 than PGDM1400.

In another aspect, provided herein are antibodies that bind the same or an overlapping epitope of Env as an antibody described herein (e.g., an antibody comprising ePGDM-G VH, and ePGDM-E, ePGDM-I or ePGDM-M VL). In certain embodiments, the epitope of an antibody can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. Usually, binding to the antigen is reduced or disrupted when a residue within the epitope is substituted to alanine. In one embodiment, the Kd of binding to the antigen is increased by about 5-fold, 10-fold, 20-fold, 10-fold or more when a residue within the epitope is substituted for alanine. In one embodiment, binding affinity is determined by ELISA. In addition, antibodies that recognize and bind to the same or overlapping epitopes of Env (e.g., an epitope of BG505 Env) can be identified using routine techniques such as an immunoassay, for example, by showing the ability of one antibody to block the binding of another antibody to a target antigen, i.e., a competitive binding assay.

In specific aspects, provided herein is an antibody, which immunospecifically binds to the same epitope as an antibody comprising a VH of SEQ ID NO: 3-12 and a VL of SEQ ID NO: 13-28 for specific binding to Env (e.g., an epitope of BG505 Env). Assays known to one of skill in the art or described herein (e.g., X-ray crystallography, hydrogen/deuterium exchange coupled with mass spectrometry (e.g., liquid chromatography electrospray mass spectrometry), alanine scanning, ELISA assays, etc.) can be used to determine if two antibodies bind to the same epitope.

In one embodiment, an antibody described herein immunospecifically binds to the same epitope as that bound by an antibody comprising a VH of SEQ ID NO: 3-12 and a VL of SEQ ID NO: 13-28.

In one embodiment, an antibody described herein immunospecifically binds to an epitope that overlaps the epitope bound by an antibody comprising a VH of SEQ ID NO: 3-12 and a VL of SEQ ID NO: 13-28.

In some embodiments, an antibody described herein is capable of competing with PGDM1400 for binding to HIV gp120. In some embodiments, the HIV gp120 is BG505 gp120.

In a specific embodiment, an antibody described herein immunospecifically binds to the same epitope as that bound by an antibody comprising ePGDM-G VH, and ePGDM-E, ePGDM-I or ePGDM-M VL or an epitope that overlaps the epitope.

In one aspect, provided herein is a method for producing an engineered variant of the PGDM1400 antibody comprising substituting one or more amino acid residues of the PGDM1400 VH to a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104, wherein the VH residues are numbered according to Kabat; and/or substituting one or more amino acid residues of the PGDM1400 VL to a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80, wherein the VL residues are numbered according to Kabat. In one aspect, provided herein is a method for producing an engineered variant of the PGDM1400 antibody comprising substituting one or more amino acid residues of the PGDM1400 VH to a Q at H3, V at H5, N at H24, T at H30, E at H85, A at H104, wherein the VH residues are numbered according to Kabat; and/or substituting one or more amino acid residues of the PGDM1400 VL to a D at L49, E or D at L53, E or R at L68, wherein the VL residues are numbered according to Kabat. In one aspect, provided herein is a method for producing an engineered variant of the PGDM1400 antibody comprising substituting one or more amino acid residues of the PGDM1400 VH to a A at H2, Q at H3, V at H5, N at H24, T at H30, Q at H39, E at H85, E at H100H, A at H104, wherein the VH residues are numbered according to Kabat; and/or substituting one or more amino acid residues of the PGDM1400 VL to a a I at L2, L at L9, D at L26, Q at L27C, E at L53, R at L68, D at L76, and A at L80, wherein the VL residues are numbered according to Kabat. In one aspect, provided herein is a method for producing an engineered variant of the PGDM1400 antibody comprising substituting one or more amino acid residues of the PGDM1400 VH to a A at H2, Q at H3, V at H5, N at H24, T at H30, Q at H39, E at H85, E at H100H, A at H104, wherein the VH residues are numbered according to Kabat; and/or substituting one or more amino acid residues of the PGDM1400 VL to a L at L9, Q at L27, E at L53, R at L68, S at L74, D at L76, and A at L80, wherein the VL residues are numbered according to Kabat. In one aspect, provided herein is a method for producing an engineered variant of the PGDM1400 antibody comprising substituting one or more amino acid residues of the PGDM1400 VH to a A at H2, Q at H3, V at H5, N at H24, T at H30, Q at H39, E at H85, E at H100H, A at H104, wherein the VH residues are numbered according to Kabat; and/or substituting one or more amino acid residues of the PGDM1400 VL to a I at L2, L at L9, Q at L27C, L at L48, E at L53, E at L68, wherein the VL residues are numbered according to Kabat. In one embodiment, the engineered variant antibody is capable of neutralizing BG505. In one embodiment, the engineered variant antibody is capable of neutralizing at least two cross-clade isolates of HIV. In one embodiment, the engineered variant antibody specifically binds to HIV Env (e.g., BG505 SOSIP).

In certain embodiments, the epitope of an antibody described herein is used as an immunogen to produce antibodies.

The affinity or avidity of an antibody for an antigen can be determined experimentally using any suitable method well known in the art, e.g., flow cytometry, enzyme-linked immunoabsorbent assay (ELISA), or radioimmunoassay (RIA), or kinetics (e.g., BIACORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., KD or Kd, Kon, Koff) are made with standardized solutions of antibody and antigen, and a standardized buffer, as known in the art and such as the buffer described herein. In some embodiments, an antibody described herein binds to HIV gp120 with a higher affinity than PGDM1400. In some embodiments, the HIV gp120 is BG505 gp120.

In some embodiments, an antibody described herein is a monoclonal antibody. Monoclonal antibodies can be made using recombinant DNA methods, for example, as described in U.S. Pat. No. 4,816,567. The polynucleotides encoding a monoclonal antibody can be amplified from a suitable source or chemically synthetized. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells.

The polynucleotide(s) encoding a monoclonal antibody can be modified in a number of different manners using recombinant DNA technology to generate alternative antibodies. In some embodiments, the constant domains of the light and heavy chains can be substituted for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

Methods for engineering antibodies can also be used and are well known in the art. An engineered antibody can have one or more amino acid residues substituted, deleted or inserted. These sequence modifications can be used to reduce immunogenicity or reduce, enhance or modify binding, affinity, on-rate, off-rate, avidity, specificity, half-life, or any other suitable characteristic, as known in the art. Antibodies can also be engineered to eliminate development liabilities by altering or eliminating sequence elements targeted for post-translational modification including glycosylation sites, oxidation sites, or deamination sites. In general, the CDR residues are directly and most substantially involved in influencing antibody binding. Accordingly, part or all of the CDR sequences are maintained while the variable framework and constant regions can be engineered by introducing substitutions, insertions, or deletions.

Antibodies disclosed herein can also optionally be engineered with retention of high affinity for the antigen and other favorable biological properties. To achieve this goal, engineered antibodies can be prepared by a process of analysis of the parental sequences and various conceptual engineered products using three-dimensional models of the parental and engineered sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In certain embodiments an antibody fragment is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from antibody phage libraries. The antibody fragment can also be linear antibodies as described in U.S. Pat. No. 5,641,870, for example, and can be monospecific or bispecific. Other techniques for the production of antibody fragments will be apparent to the skilled practitioner.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies described herein will comprise antibodies (e.g., full-length antibodies or antigen-binding fragments thereof) in which at least a fraction of one or more of the constant region domains has been deleted or otherwise altered so as to provide desired biochemical characteristics such as increased serum half-life when compared with an antibody of approximately the same antigen-binding activity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies described herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g., 10 residues) that provides some of the molecular flexibility typically imparted by the absent constant region.

It will be noted that in certain embodiments, the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies described herein can be provided by the partial deletion or substitution of a few or even a single amino acid. For example, it may be desirable to simply delete that part of one or more constant region domains that control the effector function (e.g., complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains. In further embodiments, an antibody disclosed herein comprises a variant IgG Fc region (e.g., variant IgG1 Fc region) comprising the M428L and N434S substitutions to improve the recycling of the antibody via the antibody salvage pathway. See, e.g., Grevys, et al., The Journal of Immunology, 194(11):5497-508 (2015). In some embodiments, an antibody disclosed herein comprises the variant IgG Fc region of SEQ ID NO: 110.

The present invention further embraces variants and equivalents which are substantially homologous to the antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides provided herein can be recombinant polypeptides or synthetic polypeptides comprising an antibody, or fragment thereof. It will be recognized in the art that some amino acid sequences described herein can be varied without significant effect of the structure or function of the protein. Thus, the invention further includes variations of the polypeptides which show substantial activity or which include regions of an antibody, or fragment thereof, against an HIV Env protein. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in REMINGTON'S PHARMACEUTICAL SCIENCES, 21th ed., Mack Publishing Co., Easton, PA (2005).

III. Polynucleotides

In certain aspects, provided herein are polynucleotides comprising a nucleotide sequence or nucleotide sequences encoding an antibody described herein (e.g., a variable light chain and/or variable heavy chain region) or an antigen binding fragment thereof and vectors, e.g., vectors comprising such polynucleotides. In one embodiment, the vectors can be used for recombinant expression of an antibody described herein in host cells (e.g., *E. coli* and mammalian cells). In one embodiment, the vectors can be used for administration of an antibody described herein to a patient in need thereof. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one aspect, provided herein are isolated polynucleotides encoding the heavy chain variable region or heavy chain of an antibody described herein.

In one aspect, provided herein are isolated polynucleotides encoding the light chain variable region or light chain of an antibody described herein.

In one aspect, provided herein are isolated polynucleotides encoding the heavy chain variable region or heavy chain of an antibody described herein and the light chain variable region or light chain of an antibody described herein.

In one embodiment, the polynucleotide encodes the ePGDM-G (SEQ ID NO: 9) VH. In one embodiment, the polynucleotide encodes the ePGDM-E (SEQ ID NO: 17) VL. In one embodiment, the polynucleotide encodes the ePGDM-I (SEQ ID NO: 21) VL. In one embodiment, the polynucleotide encodes the ePGDM-M (SEQ ID NO: 25) VL.

In one embodiment, the polynucleotide encodes a heavy chain variable region comprising the amino acid sequence of SEQ ID NO: 3-12. In one embodiment, the polynucleotide encodes a light chain variable region comprising the amino acid sequence of SEQ ID NO: 13-28.

In one embodiment, an isolated polynucleotide described herein encodes an antibody described herein and comprises an mRNA. In one embodiment, the mRNA comprises at least one modified nucleotide. In one embodiment, a modified mRNA encoding an antibody disclosed herein is for administering to a subject to treat or prevent HIV infection.

As used herein, an “isolated” polynucleotide or nucleic acid molecule is one which is separated from other nucleic acid molecules which are present in the natural source (e.g., in a mouse or a human) of the nucleic acid molecule. Moreover, an “isolated” nucleic acid molecule, such as a cDNA molecule, can be substantially free of other cellular material, or culture medium when produced by recombinant techniques, or substantially free of chemical precursors or other chemicals when chemically synthesized. For example, the language “substantially free” includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody or fusion polypeptide described herein is isolated or purified.

In particular aspects, provided herein are polynucleotides comprising nucleotide sequences encoding antibodies described herein, as well as antibodies that compete with such antibodies for binding to HIV, or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL of antibodies described herein (see, e.g., Table 1). The polynucleotides can comprise nucleotide sequences encoding a heavy chain comprising the VH of antibodies described herein (see, e.g., Table 1). In specific embodiments, a polynucleotide described herein encodes a VH domain comprising the amino acid sequence set forth in SEQ ID NO: 3-12. In specific embodiments, a polynucleotide described herein encodes a VH domain comprising the amino acid sequence set forth in SEQ ID NO: 9. In specific embodiments, a polynucleotide described herein encodes a VL domain comprising the amino acid sequence set forth in SEQ ID NO: 13-28. In specific embodiments, a polynucleotide described herein encodes a VL domain comprising the amino acid sequence set forth in SEQ ID NO: 17. In specific embodiments, a polynucleotide described herein encodes a VL domain comprising the amino acid sequence set forth in SEQ ID NO: 21. In specific embodiments, a polynucleotide described herein encodes a VL domain comprising the amino acid sequence set forth in SEQ ID NO: 25. In one embodiment, the antibody is a chimeric antibody.

In particular embodiments, provided herein are polynucleotides comprising a nucleotide sequence encoding an antibody comprising three VL chain CDRs, e.g., containing VL CDR1, VL CDR2, and VL CDR3 of any one of antibodies described herein (e.g., see Table 2). In specific embodiments, provided herein are polynucleotides comprising three VH chain CDRs, e.g., containing VH CDR1, VH CDR2, and VH CDR3 of any one of antibodies described herein (e.g., see Table 2). In specific embodiments, provided herein are polynucleotides comprising a nucleotide sequence encoding an anti-Env antibody comprising three VL CDRs, e.g., containing VL CDR1, VL CDR2, and VL CDR3 of any one of antibodies described herein (e.g., see Table 2) and three VH chain CDRs, e.g., containing VH CDR1, VH CDR2, and VH CDR3 of any one of antibodies described herein (e.g., see Table 2).

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody, which immunospecifically binds to Env, wherein the antibody comprises a light chain, and wherein the amino acid sequence of the VL domain can comprise the amino acid sequence set forth in Table 1, and wherein the constant region of the light chain comprises the amino acid sequence of a human kappa light chain constant region. In another particular embodiment, a polynucleotide provided herein comprises a nucleotide sequence encoding an antibody, which immunospecifically binds to Env, and comprises a light chain, wherein the amino acid sequence of the VL domain can comprise the amino acid sequence set forth in Table 1, and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to Env, wherein the antibody comprises a heavy chain, wherein the amino acid sequence of the VH domain can comprise the amino acid sequence set forth in Table 1, and wherein the constant region of the heavy chain comprises the amino acid sequence of a human alpha or gamma heavy chain constant region.

In yet another specific embodiment, a polynucleotide provided herein comprises a nucleotide sequence encoding an antibody described herein, which immunospecifically binds Env, wherein the antibody comprises a VL domain and a VH domain comprising any amino acid sequences described herein, and wherein the constant regions comprise the amino acid sequences of the constant regions of a human $IgA_1$, human $IgA_2$' human $IgG_1$ (e.g., allotype 1, 17, or 3), human $IgG_2$, or human $IgG_4$.

In yet another specific embodiment, a polynucleotide provided herein comprises a nucleotide sequences encoding an anti-Env antibody or a fragment thereof that are optimized, e.g., by codon/RNA optimization, replacement with heterologous signal sequences, and elimination of mRNA instability elements. Methods to generate optimized nucleic acids encoding an anti-Env antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an anti-Env antibody described herein or a fragment thereof (e.g., VL domain or VH domain) can hybridize to an antisense (e.g., complementary) polynucleotide of an unoptimized polynucleotide sequence encoding an anti-Env antibody described herein or a fragment thereof (e.g., VL domain or VH domain). In specific embodiments, an optimized nucleotide sequence encoding an anti-Env antibody described herein or a fragment hybridizes under high stringency conditions to antisense polynucleotide of an unoptimized polynucleotide sequence encoding an anti-Env antibody described herein or a fragment thereof. In a specific embodiment, an optimized nucleotide sequence encoding an anti-Env antibody described herein or a fragment thereof hybridizes under high stringency, intermediate or lower stringency hybridization conditions to an antisense polynucleotide of an unoptimized nucleotide sequence encoding an anti-Env antibody described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), *BioTechniques* 17: 242-246), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., PBMCs) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-Env antibodies described herein can be readily isolated and sequenced using conventional procedures (e.g., by using oligonucleotide probes that are capable of binding specifically to genes encoding the heavy and light chains of the anti-Env antibodies). PBMCs can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-Env antibodies in the recombinant host cells.

The DNA also can be modified, for example, by substituting the coding sequence for human heavy and light chain constant domains with a coding sequence for a non-immunoglobulin polypeptide, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

IV. Vectors, Cells, and Methods of Producing a Broadly Neutralizing Agent

In certain aspects, provided herein are cells (e.g., host cells) expressing (e.g., recombinantly) antibodies described herein which specifically bind to Env and related polynucleotides and expression vectors. Provided herein are vectors (e.g., expression vectors) comprising polynucleotides comprising nucleotide sequences encoding anti-Env antibodies or a fragment thereof described herein. In one embodiment, the vectors can be used for recombinant expression of an antibody described herein in host cells (e.g., mammalian cells). In one embodiment, the vectors can be used for administration of an antibody described herein to a patient in need thereof. Also provided herein are host cells comprising such vectors for recombinantly expressing anti-Env antibodies described herein. In a particular aspect, provided herein are methods for producing an antibody described herein, comprising expressing such antibody in a host cell. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In certain aspects, provided herein is an isolated vector comprising a polynucleotide described herein. In one embodiment, the vector is a viral vector.

In certain aspects, provided herein is a recombinant virus comprising a polynucleotide described herein. In one embodiment, the recombinant virus encodes an antibody described herein. In one embodiment, the recombinant virus encodes a bispecific antibody described herein. In one embodiment, the recombinant virus is a replication defective virus. Suitable replication defective viral vectors are known to those skilled in the art, for example, as disclosed in U.S. Pat. Nos. 7,198,784, 9,408,905, 9,862,931, 8,067,156, U.S. Pat. Appl. Pub. Nos. 20150291935, 20120220492, 20180291351, and 20170175137, each of which is incorporated herein by reference in its entirety. In one embodiment, the recombinant virus is a retrovirus or retroviral vector, for example, a lentivirus or lentiviral vector. In one embodiment, the recombinant virus is an adenovirus or adenoviral vector, HSV or HSV vector, or influenza virus or viral vector. In one embodiment, the recombinant virus is an adeno-associated virus (AAV). In one embodiment, the recombinant virus is for administration to a subject to prevent or treat HIV infection. In one embodiment, the recombinant virus is an adeno-associated virus (AAV) for administration to a subject to prevent or treat HIV infection. Recombinant AAV particles encoding an antibody that binds to HIV Env and methods for producing thereof are known to one skilled in the art, for example, as disclosed in U.S. Pat. No. 8,865,881 and US20190031740, each of which is incorporated by reference herein in its entirety for all purposes. See also, Lin and Balazs, Retrovirology 15:66 (2018) and van den berg et al., Molecular Therapy: methods & Clinical Development 14:100-112 (2019), each of which is incorporated by reference herein in its entirety for all purposes. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In certain aspects, provided herein is a host cell comprising a polynucleotide described herein, or a vector described herein. In one embodiment, the vector encodes an antibody described herein. In one embodiment, a vector described herein comprises a first vector encoding a VH described herein and a second vector encoding a VL described herein. In one embodiment, a vector described herein comprises a first nucleotide sequence encoding a VH described herein and a second nucleotide sequence encoding a VL described herein. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one embodiment, the host cell is selected from the group consisting of *E. coli*, *Pseudomonas*, *Bacillus*, *Streptomyces*, yeast, CHO, YB/20, NS0, PER-C6, HEK-293T, NIH-3T3, Helga, BHK, Hep G2, SP2/0, R1.1, B-W, L-M, COS 1, COS 7, BSC1, BSC40, BMT10 cell, plant cell, insect cell, and human cell in tissue culture. In one embodiment, the host cell is CHO.

In certain aspects, provided herein is a method of producing an antibody that binds to HIV comprising culturing a host cell described herein so that the polynucleotide is expressed and the antibody is produced. In one embodiment, the method further comprises recovering the antibody.

The isolated polypeptides, i.e., anti-HIV Env antibodies described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies or fragments thereof. Recombinant expression vectors are replicable DNA constructs which have synthetic or cDNA-derived DNA fragments encoding a polypeptide chain of an antibody or fragment thereof operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7030, HsS78Bst, Helga, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies described herein are produced by CHO cells or NS0 cells. In a specific embodiment, the expression of nucleotide sequences encoding antibodies described herein which immunospecifically bind Env is regulated by a constitutive promoter, inducible promoter or tissue specific promoter.

For applications where it is desired that the antibodies described herein be expressed in vivo, for example in a subject in need of treatment with an antibody described herein, any vector that allows for the expression of the antibodies and is safe for use in vivo may be used. In one embodiment, the vector is a viral vector. Viral vectors can include poxvirus (vaccinia), including vaccinia Ankara and canarypox; adenoviruses, including adenovirus type 5 (Ad5); rubella; sendai virus; rhabdovirus; alphaviruses; and adeno-associated viruses. In one embodiment, the viral vector is an adeno-associated virus. Alternatively, a polynucleotide encoding the antibody could be delivered as DNA or RNA to the subject for in vivo expression of the antibody.

Suitable host cells for expression of a polypeptide of interest such as an antibody described herein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express a recombinant protein such as an antibody described herein. Expression of recombinant proteins in mammalian cells can be performed because such proteins are generally correctly folded, appropriately modified and completely functional. Examples of suitable mammalian host cell lines include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein, e.g., an antibody, into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further an agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the polypeptide (e.g., antibody described herein) is recombinantly produced, it is also generally substantially free of culture medium, i.e., culture medium represents less than about 20%, 10%, 2%, 1%, 0.5%, or 0.1% of the volume of the protein preparation. When the polypeptide (e.g., antibody described herein) is produced by chemical synthesis, it is generally substantially free of chemical precursors or other chemicals, i.e., it is separated from chemical precursors or other chemicals which are involved in the synthesis of the protein. Accordingly, such preparations of the polypeptide (e.g., antibody described herein) have less than about 30%, 20%, 10%, or 5% (by dry weight) of chemical precursors or compounds other than the polypeptide of interest. In one embodiment, antibodies described herein are isolated or purified.

V. Pharmaceutical Compositions

Compositions comprising the antibodies or antigen-binding fragments described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL) are also provided. Further provided herein are compositions comprising a polynucleotide or polynucleotides encoding the antibodies or antigen-binding fragments described herein. In one embodiment, the polynucleotide comprises mRNA. In one embodiment, the composition is a pharmaceutical composition. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one embodiment, the composition is a lyophilized composition. In one embodiment, the composition is formulated for topical administration, and in certain embodiments the composition is formulated for vaginal or rectal administration.

In certain aspects, provided herein is a pharmaceutical composition comprising an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL) and a pharmaceutically acceptable excipient. In one embodiment, the antibody is an intact antibody. In one embodiment, the antibody is an antigen binding antibody fragment. In one embodiment, the composition is formulated for topical administration, and in certain embodiments the composition is formulated for vaginal or rectal administration. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In another embodiment, the disclosure provides a pharmaceutical composition comprising an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL). Such compositions are intended for prevention and treatment of HIV infection. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In further embodiments of the present disclosure, a composition comprising the antibody described herein can additionally be combined with other compositions for the treatment of HIV infection or the prevention of HIV transmission.

In some embodiments, an antibody described herein may be administered within a pharmaceutically-acceptable diluent, carrier, or excipient, in unit dose form. Conventional pharmaceutical practice may be employed to provide suitable formulations or compositions to administer to individuals being treated for HIV infection. In one embodiment, the administration is prophylactic. Any appropriate route of administration may be employed, for example, administration may be parenteral, intravenous, intra-arterial, subcutaneous, intramuscular, intraperitoneal, intranasal, aerosol, suppository, oral administration, vaginal, or anal.

The pharmaceutical compositions described herein are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (21st ed.), ed. A. R. Gennaro, 2005, Lippincott Williams & Wilkins, Philadelphia, PA, and Encyclopedia of Pharmaceutical Technology, eds. J. Swarbrick and J. C. Boylan, 2013, Marcel Dekker, New York, N.Y.).

The injection compositions are prepared in customary manner under sterile conditions; the same applies also to introducing the compositions into ampoules or vials and sealing the containers.

Pharmaceutical compositions according to the invention may be, for example, in unit dose form, such as in the form of ampoules, vials, suppositories, tablets, pills, or capsules. The formulations can be administered to human individuals in therapeutically or prophylactic effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

In certain embodiments, the compositions described herein can be formulated for topical administration, and in certain embodiments the composition is formulated for vaginal or rectal administration. The composition may be formulated as a gel, or formulated as a topical cream, ointment, lotion or foam formulation. Useful formulations are known in the art, for example, as disclosed in U.S. Patent Appl. Pub. No. 20130022619, which is incorporated by reference herein in its entirety for all purposes.

In certain embodiments, the composition may further comprise a pharmaceutically acceptable excipient, a lubricant, or an antiviral agent.

The topical formulations of the present invention can be used to prevent HIV infection in a human, or to inhibit transmission of the HIV virus from an infected human to another human. The topical formulations of the present invention can inhibit the growth or replication of HIV. The topical formulations are useful in the prophylactic treatment of humans who are at risk for HIV infection. The topical formulations also can be used to treat objects or materials, such as contraceptive devices (for example condoms or intrauterine devices), medical equipment, supplies, or fluids, including biological fluids, such as blood, blood products, and tissues, to prevent or inhibit viral infection of a human. Such topical formulations also are useful to prevent transmission, such as sexual transmission of viral infections, e.g., HIV, which is the primary way in which HIV is transmitted globally. The methods of prevention or inhibition or retardation of transmission of viral infection, e.g., HIV infection, in accordance with the present invention, comprise vaginal, rectal, penile or other topical treatment with an antiviral effective amount of a topical preparation of the present invention, alone or in combination with another antiviral compound as described herein.

In one embodiment the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. These formulations are useful to protect not only against sexual transmission of HIV, but also to prevent infection of a baby during passage through the birth canal. Thus the vaginal administration can take place prior to sexual intercourse, during sexual intercourse, and immediately prior to childbirth.

As a vaginal formulation, the active ingredient may be used in conjunction with a spermicide and may be employed with a condom, diaphragm, sponge or other contraceptive device. Examples of suitable spermicides include nonylphenoxypolyoxyethylene glycol (nonoxynol 9), benzethonium chloride, and chlorindanol. Suitably, the pH of the composition is 4.5 to 8.5. Vaginal compositions preferably have a pH of 4.5 to 6, most preferably about 5.

Vaginal formulations include suppositories (for example, gel-covered creams), tablets and films. The suppositories can be administered by insertion with an applicator using methods well known in the art.

Vaginal formulations further include vaginal ring devices formulated for sustained release. See, e.g., Morrow et al., Eur J Pharm Biopharm. 77(1):3-10 (2011), Zhao et al., Antimicrob Agents Chemother. 61(7) pii: e02465-16 (2017).

Buccal formulations include creams, ointments, gels, tablets or films that comprise ingredients that are safe when administered via the mouth cavity. Buccal formulations can also comprise a taste-masking or flavoring agent.

The present compositions may be associated with a contraceptive device or article, such as a vaginal ring device, an intrauterine device (IUD), vaginal diaphragm, vaginal sponge, pessary, condom, etc.

In one embodiment the compositions described herein are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use. As used herein, "condom" refers to a barrier device which is used to provide a watertight physical barrier between male and female genitalia during sexual intercourse, and which is removed after intercourse. This term includes conventional condoms that cover the penis; it also includes so-called "female condoms" which are inserted into the vaginal cavity prior to intercourse.

In another embodiment a composition described herein is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of an antibody described herein.

In certain embodiments, the composition may further comprise a pharmaceutically acceptable excipient, a lubricant, or an antiviral agent.

Compositions used in the methods of this invention may also comprise other active agents, such as another agent to prevent HIV infection, and agents that protect individuals from conception and other sexually transmitted diseases. Thus, in another embodiment the compositions used in this invention further comprise a second anti-HIV agent, a virucide effective against viral infections other than HIV, and/or a spermicide.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In the cream or ointment embodiments of the present invention, the topical formulation comprises one or more lubricants. The gels and foams of the present invention optionally can include one or more lubricants.

Non-limiting examples of useful lubricants include cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate, white wax, or mixtures of two or more of the above.

The gel formulations of the present invention comprise one or more gelling agents. Non-limiting examples of useful gelling agents include carboxylic acid polymers including acrylic acid polymers crosslinked with cross links such as allyl ethers of sucrose (e.g. carbomer brand thickeners), cetostearyl alcohol, hydroxymethyl cellulose, polyoxyethylene-polyoxypropylene copolymer, sodium carboxymethylcellulose, polyvinyl pyrrolidone, or mixtures of two or more thereof.

VI. Uses and Methods

Therapeutic Uses and Methods:

In one aspect, provided herein is a method of treating HIV or inhibiting transmission of HIV. In one embodiment, the method of inhibiting transmission of HIV comprises administering to a subject in need thereof an effective amount of an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition described herein, an isolated polynucleotide described herein, or a recombinant virus (e.g., recombinant AAV) described herein. In one embodiment, the method of inhibiting transmission of HIV comprises administering to a subject in need thereof an effective amount of an antibody (e.g., a bispecific antibody) described herein. In one embodiment, the method of inhibiting transmission of HIV comprises administering to a subject in need thereof an effective amount of a recombinant AAV encoding an antibody (e.g., a bispecific antibody) described herein. In one embodiment, the method of inhibiting transmission of HIV comprises administering to a subject in need thereof an effective amount of an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL). In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject that has been exposed to HIV or is at risk of being exposed to HIV is a newborn. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one aspect, provided herein is a method of reducing the risk of a subject becoming infected with HIV comprising administering to the subject in need thereof an effective amount of an antibody (e.g., bispecific antibody) described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition described herein, an isolated polynucleotide described herein, or a recombinant virus described herein. In one embodiment, the method comprises administering to a subject in need thereof an effective amount of an antibody (e.g., a bispecific antibody) described herein. In one embodiment, the method comprises administering to a subject in need thereof an effective amount of a recombinant AAV encoding an antibody (e.g., a bispecific antibody) described herein. In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject that has been exposed to HIV or is at risk of being exposed to HIV is a newborn. In one aspect, provided herein is an antibody (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition, an isolated polynucleotide, or a recombinant virus for reducing the risk of a subject becoming infected with HIV. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one aspect, provided herein is a method for passively immunizing a subject comprising administering to the subject in need thereof an effective amount of an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition described herein, an isolated polynucleotide described herein, or a recombinant virus described herein. In one embodiment, the method comprises administering to a subject in need thereof an effective amount of an antibody (e.g., a bispecific antibody) described herein. In one embodiment, the method comprises administering to a subject in need thereof an effective amount of a recombinant AAV encoding an antibody (e.g., a bispecific antibody) described herein. In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject that has been exposed to HIV or is at risk of being exposed to HIV is a newborn. In one aspect, provided herein is provided herein is an antibody (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition, an isolated polynucleotide, or a recombinant virus for passively immunizing a subject. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

Further provided herein is a method of neutralizing an HIV virus comprising contacting the virus with an effective amount of an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL). In one embodiment, the virus is comprised by a composition, for example, a fluid, including a biological fluid, such as blood or blood product. In certain embodiments, the method comprises adding an antibody described herein to a composition comprising HIV in a sufficient amount or concentration to neutralize the HIV. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

Further provided herein is a method of reducing viral load comprising administering to a subject in need thereof an effective amount of an antibody (e.g., bispecific antibody) described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition described herein, an isolated polynucleotide described herein, or a recombinant virus described herein. In one embodiment, the method comprises administering to a subject in need thereof an effective amount of an antibody (e.g., a bispecific antibody) described herein. In one embodiment, the method comprises administering to a subject in need thereof an effective amount of a recombinant AAV encoding an antibody (e.g., a bispecific antibody) described herein. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one embodiment of a method described herein, the antibody can be a chimeric antibody, engineered antibody, recombinant antibody, or a monoclonal antibody described herein. In one embodiment, the antibody is a full antibody, an F(ab) fragment, or an F(ab)2 fragment described herein. In a specific embodiment, the antibody is an engineered monoclonal antibody described herein. In a specific embodiment, the antibody is a recombinant monoclonal antibody described herein. In a specific embodiment, the antibody is a chimeric monoclonal antibody described herein. In a specific embodiment, the antibody is a F(ab) described herein. In a specific embodiment, the antibody is a F(ab')2 fragment described herein.

In one embodiment, a method of preventing HIV infection provided herein comprises administering to a subject in need thereof a therapeutically sufficient amount of an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition described herein, an isolated polynucleotide described herein, or a recombinant virus described herein. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one embodiment, a method of treating HIV/AIDS provided herein comprises administering to a subject in need thereof a therapeutically sufficient amount of an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), a pharmaceutical composition described herein, an isolated polynucleotide described herein, or a recombinant virus described herein. In one embodiment, a method of treating HIV/AIDS comprises administering an antibody described herein. In one embodiment, a method of treating HIV/AIDS comprises administering a pharmaceutical composition described herein. In one embodiment, a method of treating HIV/AIDS comprises administering an isolated polynucleotide described herein. In one embodiment, a method of treating HIV/AIDS comprises administering a recombinant virus described herein. In one aspect, provided herein is an antibody, a pharmaceutical composition, an isolated polynucleotide, or a recombinant virus for treating HIV/AIDS. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one embodiment, the administering to the subject is by at least one mode selected from oral, parenteral, subcutaneous, intramuscular, intravenous, vaginal, rectal, buccal, sublingual, and transdermal In one embodiment, a method of treatment described herein further comprises administering at least one additional therapeutic agent. In one embodiment, the additional therapeutic agent comprises an antiretroviral therapy (ART) agent, a reservoir activator, an immunomodulator, a second antibody, or a second and third antibody. In one embodiment, the additional therapeutic agent comprises a second antibody. In one embodiment, the additional therapeutic agent comprises a second and third antibody. In one embodiment, the additional therapeutic agent comprises a second and optionally third antibody which is an anti-HIV antibody. In one embodiment, the additional therapeutic agent comprises a second and optionally third antibody which is an anti-HIV Env antibody. In one embodiment, the additional therapeutic agent comprises a second and optionally third anti-HIV Env antibody which binds to an HIV Env epitope region different from the HIV Env epitope region bound by an antibody disclosed herein. In one embodiment, the additional therapeutic agent comprises a second and optionally third anti-HIV Env antibody which binds to the CD4 binding site (CD4bs) epitope region, the N332 glycan epitope region near the V3 loop, the gp120-gp41 interface epitope region, or the gp41 membrane proximal external epitope region (MPER). In one embodiment, the additional therapeutic agent comprises a second and optionally third anti-HIV Env antibody which binds to the CD4 binding site (CD4bs) epitope region, V1/V2-glycan site (V2g) epitope region, the N332 glycan epitope region near the V3 loop, the gp120-gp41 interface epitope region, or the gp41 membrane proximal external epitope region (MPER). In one embodiment, the additional therapeutic agent comprises a second anti-HIV Env antibody which binds to the CD4 binding site (CD4bs) epitope region. In one embodiment, the additional therapeutic agent comprises a second anti-HIV Env antibody which binds to the V1/V2-glycan site (V2g) epitope region. In one embodiment, the additional therapeutic agent comprises a second anti-HIV Env antibody which binds to the N332 glycan epitope region near the V3 loop. In one embodiment, the additional therapeutic agent comprises a second anti-HIV Env antibody which binds to the gp120-gp41 interface epitope region. In one embodiment, the additional therapeutic agent comprises a second anti-HIV Env antibody which binds to the gp41 membrane proximal external epitope region (MPER).

In certain embodiments, the subject is at risk for exposure to HIV. In some embodiments, the subject is infected with HIV. In some embodiments, the subject is diagnosed with AIDS. In certain embodiments, the subject at risk for exposure to HIV is a health care worker. In certain embodiments, the subject at risk for exposure to HIV is a sex worker. In certain embodiments, the subject at risk for exposure to HIV is a sexual partner of an HIV infected individual. In certain embodiments, the subject at risk for exposure to HIV is a newborn.

The invention also features methods of blocking HIV infection in a subject (e.g., a human) at risk of HIV transmission. For example, in one aspect, the subject may be a fetus of an HIV-infected pregnant female and the method includes administering to the HIV-infected pregnant female an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL), thereby blocking the HIV infection in the fetus. In other instances, the subject is a newborn having an HIV-infected mother, a subject at risk of HIV transmission following a needle stick injury, or a subject at risk of HIV transmission following a sexual exposure to an HIV-infected individual. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In instances when the subject is a newborn having an HIV-infected mother, the newborn can be administered an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL y) peripartum and/or postpartum, for example, prior to, during, and/or following breastfeeding from the HIV-infected mother, in order to block an HIV infection in the newborn. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In instances when the subject is at risk of HIV transmission following a sexual exposure to an HIV-infected individual, the subject can be administered an antibody described herein (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL) following the sexual exposure in order to block an HIV infection in the subject. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In some embodiments, an antibody described herein can be used as a microbicides to prevent mucosal HIV acquisition. In some embodiments, an antibody described herein is used to prevent vaginal or rectal acquisition of HIV. In some embodiments, an antibody described herein can be used as a microbicides to reduce the likelihood of mucosal HIV acquisition. In some embodiments, an antibody described herein is used to reduce the likelihood of vaginal or rectal acquisition of HIV.

In any of the methods described above, further administration of ART and/or an immunomodulator and/or a second antibody is contemplated. For example, the ART and/or immunomodulator and/or a second antibody can be administered in conjunction with, prior to, concurrently with, subsequent to, or within the context of a treatment regimen that includes administration of an antibody described herein.

An antibody described herein, or a pharmaceutical composition described herein can be delivered to a subject by a variety of routes, such as oral, parenteral, subcutaneous, intravenous, intradermal, transdermal, intranasal, vaginal, or anal. In one embodiment, the antibody or pharmaceutical composition is administered intravenously, vaginally, or anally.

The amount of an antibody described herein, or a pharmaceutical composition described herein which will be effective in the treatment and/or prevention of a condition will depend on the nature of the disease, and can be determined by standard clinical techniques.

The precise dose to be employed in a pharmaceutical composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Detection & Diagnostic Uses

An antibody described herein can be used to detect HIV and/or assay HIV levels in a biological sample using classical immunohistological methods known to those of skill in the art, including immunoassays, such as the enzyme linked immunosorbent assay (ELISA), immunoprecipitation, or Western blotting. An antibody described herein can also be used as an imaging agent, for example, a tissue-penetrating imaging agent. In one embodiment, an antibody described herein is conjugated with a detectable label. Suitable assay labels are known in the art and include enzyme labels, such as, glucose oxidase; radioisotopes, such as iodine ($^{125}$I, $^{121}$I), carbon ($^{14}$C), sulfur ($^{35}$S), tritium (3H), indium ($^{121}$In), and technetium ($^{99}$Tc); luminescent labels, such as luminol; and fluorescent labels, such as fluorescein and rhodamine, and biotin. Such labels can be used to label an antibody or fusion polypeptide described herein. Alternatively, a second antibody that recognizes an antibody described herein can be labeled and used in combination with the antibody described herein to detect HIV levels.

As used herein, the term "biological sample" refers to any biological sample obtained from a subject, cell line, tissue, or other source potentially comprising HIV. Methods for obtaining tissue biopsies and body fluids from animals (e.g., humans) are well known in the art.

In another embodiment, an antibody described herein can be used to detect levels of HIV, which levels can then be linked to certain disease symptoms. An antibody described herein may carry a detectable or functional label. An antibody described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An antibody described herein can carry a radioactive label, such as the isotopes $^{3}$H, $^{14}$C, $^{32}$P, $^{35}$I, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of an antibody described herein to HIV. In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an antibody described herein under conditions that allow for the formation of a complex between the antibody and HIV. Any complexes formed between the antibody and HIV are detected and compared in the sample and the control. An antibody described herein can also be used to purify HIV via immunoaffinity purification.

In some aspects, provided herein are methods for in vitro detecting HIV in a sample, comprising contacting said sample with an antibody described herein. In some aspects, provided herein is the use of an antibody described herein, for in vitro detecting HIV in a sample. In one aspect, provided herein is an antibody or pharmaceutical composition described herein for use in the detection of HIV in a subject. In one aspect, provided herein is an antibody or pharmaceutical composition described herein for use as a diagnostic. In one preferred embodiment, the antibody comprises a detectable label. In one embodiment, the subject is a human. In one embodiment, the method of detecting HIV in a sample comprises contacting the sample with an antibody described herein.

In some embodiments, the present disclosure provides methods of purifying HIV from a sample. In some embodiments, the method of purifying HIV from a sample comprises contacting the sample with an antibody described herein under conditions that allow the antibody to bind to HIV. In some embodiments, the antibody comprises a tag, for example, hexa-histidine tag or FLAG-tag to facilitate the purification of HIV.

VII. Kits

Provided herein are kits comprising one or more antibodies described herein or one or more fusion polypeptides (e.g., an antibody comprising the ePGDM-G (SEQ ID NO: 9) VH and ePGDM-E (SEQ ID NO: 17), ePGDM-I (SEQ ID NO: 21) or ePGDM-M (SEQ ID NO: 25) VL) described herein. In some embodiments, a pharmaceutical pack or kit described herein comprises one or more containers filled with one or more of the ingredients of the pharmaceutical compositions described herein, such as one or more antibodies described herein. In some embodiments, a kit contains an antibody described herein or a pharmaceutical composition described herein, and a second prophylactic or therapeutic agent used in the treatment or prevention of HIV. In one embodiment, the second agent is an antiretroviral agent. In one embodiment, the second agent is a reservoir activator. In one embodiment, the second agent is an immunomodulator. In one embodiment, the second agent is one or more anti-HIV antibody. In one embodiment, the second agent is one or more anti-HIV Env antibody that binds to an HIV Env epitope region different from the HIV Env epitope region bound by an antibody disclosed herein. In one embodiment, the second agent is one or more anti-HIV Env antibody that binds to the CD4 binding site (CD4bs) epitope region, V1/V2-glycan site (V2g) epitope region, or gp41 MPER epitope region. In some embodiments, a kit contains an antibody described herein or a pharmaceutical composition described herein, and a reagent used in the detection of HIV. In one embodiment, the detection reagent comprises DNA primers for the detection of HIV. Optionally associated with such container(s) can be a notice in the form prescribed by a governmental agency regulating the manufacture, use or sale of pharmaceuticals or biological products, which notice reflects approval by the agency of manufacture, use or sale for human administration. In one embodiment, the antibody comprises the ePGDM-G (SEQ ID NO: 9) VH and ePGDM-E (SEQ ID NO: 17) VL. In one embodiment, the antibody comprises the ePGDM-G (SEQ ID NO: 9) VH and ePGDM-I (SEQ ID NO: 21) VL. In one embodiment, the antibody comprises the ePGDM-G (SEQ ID NO: 9) VH and ePGDM-M (SEQ ID NO: 25) VL.

In one embodiment, a kit described herein comprises an antibody described herein or a pharmaceutical composition described herein and a) a detection reagent, b) an HIV antigen, c) a notice that reflects approval for use or sale for human administration, or d) any combination thereof.

In one embodiment, a kit described herein comprises a fusion polypeptide described herein or a pharmaceutical composition described herein and a) a detection reagent, b) an HIV antigen, c) a notice that reflects approval for use or sale for human administration, or d) any combination thereof.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

All documents, patent, and patent applications cited herein are hereby incorporated by reference, and may be employed in the practice described herein.

EXAMPLES

Example 1. General Design Strategy to Generate Enhanced Engineered Variant Broadly Neutralizing Anti-HIV Antibodies An objective in the design of enhanced bnAbs is to increase neutralization potency. The general design strategy combines directed evolution (yeast surface display, FACS and deep sequencing) with informatics analysis and computational modeling, substantially as described in PCT/US2019/43578, filed Jul. 26, 2019, incorporated by reference herein in its entirety. See also, J. Jardine et al., Rational HIV immunogen design to target specific germline B cell receptors. *Science* 340, 711-716 (2013); J. G. Jardine et al., HIV-1 broadly neutralizing antibody precursor B cells revealed by germline-targeting immunogen. *Science* 351, 1458-1463 (2016). The process is broken down into two overall steps—identification of single beneficial mutations followed by identification of combinations of beneficial mutations. In the first step, yeast surface display, FACS and deep sequencing is used to analyze the effect all possible single mutations in the antibody for binding to multiple Env variants under desired conditions, e.g., physiological conditions (PBS). Mutations from this scanning dataset are combined with structural prediction and other informatics analysis, which is then used to make a combinatorial library containing ~$10^7$ bnAb variants containing multiple mutations that have been shown experimentally or predicted computationally to improve bnAb functionality. In the second step, this combinatorial library is displayed on yeast and again screened for improved binding to multiple Env variants. Following several rounds of enrichment, the selected clones are deep sequenced and analyzed to identify enhanced engineered variant bnAbs. Then the bnAb variants are recombinantly produced as IgG for characterization.

To account for the diversity in HIV, the combinatorial library can be selected for improved affinity against multiple Env isolates. Separate deep sequencing is performed on the combinatorial antibody library enriched on individual isolates to produce multiple datasets. The deep sequencing datasets are informatically analyzed to identify mutations that enriched across multiple datasets, rather than in a small subset of datasets. Enrichment across multiple datasets indicates that the mutations are broadly beneficial mutations, whereas enrichment in a small subset of datasets indicates that the mutations would only yield strain-specific improvements. Accordingly, the enhanced engineered antibodies identified are optimized against a panel of diverse Env variants.

Lastly, the sequence of enhanced engineered antibody candidates can be analyzed for known development liabilities (post-translational modification, oxidation sites, deamination sites, etc.) that could be easily substituted for other mutations based on the mutational datasets.

Example 2. The Engineered Variant PGDM1400 Antibodies have Enhanced Neutralization Breadth and Potency The breadth and potency of the enhanced engineered PGDM1400 variant antibodies' neutralization activity was determined using standard assays. Briefly, plasmids encoding various HIV Env isolates were co-transfected into HEK 293T cells (ATCC) with pSG3ΔEnv, an Env-deficient genomic backbone plasmid, in a 1:2 ratio using X-tremeGENE HP (Roche) as transfection reagent. Cell culture supernatants were harvested 3 days post transfection and sterile filtered through a 0.22 μm filter. Neutralizing activity was measured by incubating monoclonal antibodies or sera with replication incompetent pseudovirus for (h at 37C before transferring onto TZM-bl target cells (aidsreagent.org) as described previously. Walker, L. M. et al., *Nature* 477, 466-470 (2011).

Neutralization breadth and potency of the ePGDM5, ePGDM9, ePGDM13, and PGDM1400 parent antibodies on a 116 cross-clade virus panel are shown in the Table below. ePGDM5 comprises the ePGDM-G VH (SEQ ID NO: 9) and ePGDM-E VL (SEQ ID NO: 17), ePGDM9 comprises the ePGDM-G VH (SEQ ID NO: 9) and ePGDM-I VL (SEQ ID NO: 21), and ePGDM13 comprises the ePGDM-G VH (SEQ ID NO: 9) and ePGDM-M VL (SEQ ID NO: 25). As shown in the Table below, that the engineered ePGDM antibodies disclosed herein have enhanced neutralization breadth and potency compared to the previously identified broadly neutralizing anti-HIV env antibodies.

| Clade | VirusStrain | IC50 (μg/ml) with constrains | | | |
|---|---|---|---|---|---|
| | | ePGDM5 | ePGDM9 | ePGDM13 | PGDM1400 |
| A | 0260.v5.c36 | 0.021 | 0.018 | 0.025 | 0.035 |
| A | 0330.v4.c3 | 0.003 | 0.003 | 0.002 | 0.004 |
| A | 191084B7-19 | 0.001 | 0.002 | 0.001 | 0.002 |
| A | 191955_A11 | 0.021 | 0.007 | 0.008 | 0.013 |
| A | 9004SS_A3_4 | >100 | >100 | >100 | >100 |
| A | MS208.A1 | 0.007 | 0.009 | 0.027 | 0.010 |
| A | Q23.17 | 0.001 | 0.000 | 0.001 | 0.001 |
| A | Q259.d2.17 | 0.013 | 0.012 | 0.037 | 0.068 |
| A | Q461.e2 | 0.104 | 0.060 | 0.132 | 0.143 |
| A | Q769.d22 | 0.003 | 0.002 | 0.002 | 0.007 |
| A | Q842.d12 | >100 | >100 | >100 | >100 |
| AC | 3301.v1.c24 | 0.043 | 0.021 | 0.057 | 0.131 |
| AC | 6041.v3.c23 | 0.005 | 0.002 | 0.007 | 0.016 |
| AC | 6540.v4.c1 | 0.012 | 0.008 | 0.015 | 0.007 |
| AC | 6545.v4.c1 | 0.043 | 0.041 | 0.076 | 0.148 |
| ACD | 0815.v3.c3 | >100 | >100 | >100 | >100 |
| ACD | 3103.v3.c10 | 0.063 | 0.073 | 0.090 | 0.223 |
| AE | 620345.c01 | >100 | >100 | >100 | >100 |
| AE | BJOX009000.02.4 | 0.296 | 0.234 | 0.265 | 1.104 |
| AE | BJOX010000.06.2 | 0.536 | 0.293 | 0.979 | 0.871 |
| AE | BJOX015000.11.5 | 1.099 | 0.958 | 1.715 | 1.054 |
| AE | BJOX025000.01.1 | 0.018 | 0.018 | 0.018 | 0.055 |
| AE | BJOX028000.10.3 | 0.021 | 0.019 | 0.035 | 0.121 |
| AE | C1080.c03 | 0.003 | 0.001 | 0.001 | 0.001 |
| AE | C3347.c11 | 0.005 | 0.003 | 0.009 | 0.015 |
| AE | C4118.c09 | 0.000 | 0.001 | 0.001 | 0.002 |
| AE | CNE5 | 0.001 | 0.001 | 0.001 | 0.001 |
| AE | CNE8 | 0.001 | 0.001 | 0.005 | 0.001 |
| AE | R1166.c01 | 0.166 | 0.215 | 0.194 | 1.479 |
| AE | R2184.c04 | 0.004 | 0.003 | 0.005 | 0.006 |
| AE | R3265.c06 | 0.028 | 0.019 | 0.026 | 0.019 |
| AG | 928-28 | 0.031 | 0.027 | 0.019 | 0.069 |
| AG | T211-9 | 0.025 | 0.020 | 0.028 | 0.058 |
| AG | T235-47 | 0.005 | 0.004 | 0.005 | 0.011 |
| AG | T250-4a.k.a.CRFa.k.a.CRF250 | 0.065 | 0.041 | 0.035 | 0.280 |
| AG | T251-18 | >100 | >100 | >100 | >100 |
| AG | T255-34 | 0.018 | 0.002 | 0.007 | 0.046 |
| AG | T257-31 | 0.016 | 0.019 | 0.020 | 0.138 |
| AG | T263-8 | 0.019 | 0.015 | 0.025 | 0.020 |
| AG | T278-50 | 1.058 | 0.506 | 1.600 | 5.413 |
| B | 6535.3 | 98.190 | 57.830 | >100 | >100 |
| B | 62357_14_D3_4589 | 9.979 | 9.508 | 17.370 | >100 |
| B | 6240_08_TA5_4622 | 2.023 | 1.650 | 3.158 | 52.430 |
| B | 6244_13_B5_4576 | 18.910 | 12.560 | 30.760 | >100 |
| B | 1006_11_C3_1601 | 0.473 | 0.588 | 0.826 | 1.857 |
| B | 1012_11_TC21_3257 | 0.076 | 0.042 | 0.065 | 0.076 |
| B | 1054_07_TC4_1499 | >100 | >100 | >100 | >100 |
| B | 1056_10_TA11_1826 | 0.893 | 0.903 | 1.508 | 3.379 |
| B | AC10.0.29 | 0.275 | 0.074 | 0.194 | 0.549 |
| B | CAAN5342.A2 | 73.040 | 17.510 | 40.240 | >100 |
| B | PVO.4 | 1.393 | 1.925 | 2.948 | 3.406 |
| B | QH0692.42 | >100 | >100 | >100 | >100 |
| B | REJO4541.67 | 0.001 | 0.001 | 0.002 | 0.004 |
| B | RHPA4259.7 | 0.464 | 0.145 | 0.358 | 0.491 |
| B | SC05_8C11_2344 | 3.615 | 1.061 | 2.360 | 4.459 |
| B | SC422661.8 | 1.331 | 1.333 | 1.564 | 15.710 |
| B | THRO4156.18 | n.t. | n.t. | n.t. | n.t. |
| B | TRJO4551.58 | >100 | >100 | >100 | >100 |
| B | TRO.11 | 0.315 | 0.163 | 0.352 | 0.206 |
| B | WEAU_d15_410_5017 | 0.001 | 0.002 | 0.003 | 0.075 |
| B | WITO4160.33 | 0.004 | 0.002 | 0.003 | 0.003 |
| BC | CNE17 | 0.007 | 0.003 | 0.008 | 0.005 |
| BC | CNE19 | 0.003 | 0.003 | 0.003 | 0.005 |
| BC | CNE20 | 0.004 | 0.002 | 0.004 | 0.005 |
| BC | CNE21 | 0.002 | 0.002 | 0.001 | 0.003 |
| BC | CNE30 | >100 | >100 | >100 | >100 |
| BC | CNE52 | 6.142 | 1.848 | 2.832 | >100 |
| BC | CNE53 | 0.020 | 0.007 | 0.015 | 0.026 |
| BC | CNE58 | 0.004 | 0.002 | 0.003 | 0.003 |
| C | 1394C9G1(Rev-) | 0.002 | 0.001 | 0.003 | 0.003 |
| C | 246FC1G | >100 | >100 | >100 | >100 |
| C | 249MB10 | 0.011 | 0.007 | 0.032 | 0.021 |
| C | 7030102001E5(Rev-) | >100 | >100 | >100 | >100 |
| C | BF1266.431a | 0.004 | 0.002 | 0.004 | 0.006 |
| C | CAP210.2.00.E8 | 0.057 | 0.055 | 0.135 | 0.330 |
| C | CAP45.2.00.G3 | 0.001 | 0.001 | 0.002 | 0.001 |

-continued

| Clade | VirusStrain | ePGDM5 | ePGDM9 | ePGDM13 | PGDM1400 |
|---|---|---|---|---|---|
| C | Ce0393_C3 | 0.016 | 0.004 | 0.006 | 0.009 |
| C | Ce0682_E4 | 0.005 | 0.005 | 0.011 | 0.009 |
| C | Ce1086_B2 | n.t. | n.t. | n.t. | n.t. |
| C | Ce1172_H1 | 0.016 | 0.027 | 0.061 | 0.218 |
| C | Ce1176_A3 | 0.022 | 0.022 | 0.031 | 0.526 |
| C | Ce2010_F5 | >100 | >100 | >100 | >100 |
| C | Ce2060_G9 | 0.011 | 0.134 | 0.018 | 0.025 |
| C | Ce703010054_2A2 | 0.008 | 0.008 | 0.008 | 0.014 |
| C | Ce704809221_1B3 | 0.187 | 0.135 | 0.339 | 0.320 |
| C | Du156.12 | 0.006 | 0.004 | 0.006 | 0.006 |
| C | Du172.17 | 1.494 | 0.865 | 1.500 | 5.417 |
| C | Du422.1 | 8.639 | 13.310 | 27.470 | 33.370 |
| C | HIV-0013095-2.11 | >100 | >100 | >100 | >100 |
| C | HIV-001428-2.42 | 0.003 | 0.002 | 0.003 | 0.014 |
| C | HIV-16055-2.3 | 0.002 | 0.001 | 0.003 | 0.003 |
| C | HIV-16845-2.22 | >100 | >100 | >100 | >100 |
| C | ZM109F.PB4 | 0.030 | 0.027 | 0.049 | 0.098 |
| C | ZM135M.PL10a | >100 | >100 | >100 | >100 |
| C | ZM197M.PB7 | 0.035 | 0.023 | 0.060 | 0.071 |
| C | ZM214M.PL15 | >100 | >100 | >100 | >100 |
| C | ZM233M.PB6 | 0.002 | 0.002 | 0.001 | 0.002 |
| C | ZM247v1(Rev-) | n.t. | n.t. | n.t. | n.t. |
| C | ZM249M.PL1 | 0.035 | 0.002 | 0.014 | 0.025 |
| C | ZM53M.PB12 | 0.005 | 0.006 | 0.005 | 0.009 |
| CD | 3817.v2.c59 | 0.232 | 0.160 | 13.970 | >100 |
| CD | 6480.v4.c25 | >100 | >100 | >100 | >100 |
| CD | 6811.v7.c18 | >100 | >100 | >100 | >100 |
| CD | 6952.v1.c20 | 0.033 | 0.052 | 0.079 | 1.758 |
| CD | 89-F1_2_25 | 0.001 | 0.001 | 0.001 | 0.003 |
| D | 191821_E6_1 | n.t. | n.t. | n.t. | n.t. |
| D | 231965.c01 | 0.009 | 0.009 | 0.015 | 0.061 |
| D | 3016.v5.c45 | >100 | >100 | >100 | >100 |
| D | A07412M1.vrc12 | 0.009 | 0.026 | 0.029 | 0.029 |
| G | P0402_C2_11 | 0.004 | 0.001 | 0.001 | 0.007 |
| G | P1981_C5_3 | 0.295 | 0.146 | 0.319 | 18.890 |
| G | X1193_C1 | 0.039 | 0.039 | 0.095 | 0.094 |
| G | X1254_C3 | 0.217 | 0.178 | 0.518 | 45.350 |
| G | X1632_S2_B10 | 0.003 | 0.003 | 0.003 | 0.034 |
| G | X2088_C9 | 28.570 | >100 | 64.130 | >100 |
| G | X2131_C1_B5 | NT | NT | NT | NT |

| | | IC80 (μg/ml) with constrains | | | |
|---|---|---|---|---|---|
| Clade | VirusStrain | ePGDM5 | ePGDM9 | ePGDM13 | PGDM1400 |
| A | 0260.v5.c36 | 0.084 | 0.073 | 0.098 | 0.140 |
| A | 0330.v4.c3 | 0.010 | 0.010 | 0.008 | 0.016 |
| A | 191084B7-19 | 0.005 | 0.006 | 0.003 | 0.008 |
| A | 191955_A11 | 0.083 | 0.029 | 0.033 | 0.050 |
| A | 9004SS_A3_4 | >100 | >100 | >100 | >100 |
| A | MS208.A1 | 0.029 | 0.036 | 0.109 | 0.041 |
| A | Q23.17 | 0.004 | 0.002 | 0.004 | 0.005 |
| A | Q259.d2.17 | 0.051 | 0.048 | 0.150 | 0.271 |
| A | Q461.e2 | 0.415 | 0.240 | 0.528 | 0.572 |
| A | Q769.d22 | 0.011 | 0.009 | 0.010 | 0.028 |
| A | Q842.d12 | >100 | >100 | >100 | >100 |
| AC | 3301.v1.c24 | 0.174 | 0.084 | 0.228 | 0.523 |
| AC | 6041.v3.c23 | 0.021 | 0.007 | 0.029 | 0.064 |
| AC | 6540.v4.c1 | 0.050 | 0.031 | 0.060 | 0.026 |
| AC | 6545.v4.c1 | 0.170 | 0.164 | 0.305 | 0.594 |
| ACD | 0815.v3.c3 | >100 | >100 | >100 | >100 |
| ACD | 3103.v3.c10 | 0.254 | 0.290 | 0.360 | 0.892 |
| AE | 620345.c01 | >100 | >100 | >100 | >100 |
| AE | BJOX009000.02.4 | 1.182 | 0.936 | 1.058 | 4.415 |
| AE | BJOX010000.06.2 | 2.145 | 1.170 | 3.915 | 3.484 |
| AE | BJOX015000.11.5 | 4.395 | 3.831 | 6.861 | 4.214 |
| AE | BJOX025000.01.1 | 0.072 | 0.072 | 0.071 | 0.220 |
| AE | BJOX028000.10.3 | 0.086 | 0.078 | 0.139 | 0.483 |
| AE | C1080.c03 | 0.011 | 0.004 | 0.003 | 0.005 |
| AE | C3347.c11 | 0.021 | 0.011 | 0.037 | 0.061 |
| AE | C4118.c09 | 0.002 | 0.005 | 0.005 | 0.006 |
| AE | CNE5 | 0.004 | 0.003 | 0.004 | 0.003 |
| AE | CNE8 | 0.003 | 0.002 | 0.022 | 0.003 |
| AE | R1166.c01 | 0.664 | 0.860 | 0.777 | 5.916 |
| AE | R2184.c04 | 0.017 | 0.011 | 0.019 | 0.022 |
| AE | R3265.c06 | 0.113 | 0.078 | 0.104 | 0.075 |
| AG | 928-28 | 0.125 | 0.108 | 0.077 | 0.277 |
| AG | T211-9 | 0.099 | 0.081 | 0.113 | 0.234 |
| AG | T235-47 | 0.022 | 0.017 | 0.019 | 0.044 |

-continued

| | | | | | |
|---|---|---|---|---|---|
| AG | T250-4a.k.a.CRFa.k.a.CRF250 | 0.261 | 0.163 | 0.140 | 1.121 |
| AG | T251-18 | >100 | >100 | >100 | >100 |
| AG | T255-34 | 0.071 | 0.008 | 0.029 | 0.182 |
| AG | T257-31 | 0.064 | 0.076 | 0.078 | 0.552 |
| AG | T263-8 | 0.076 | 0.060 | 0.101 | 0.081 |
| AG | T278-50 | 4.233 | 2.024 | 6.399 | 21.653 |
| B | 6535.3 | >100 | >100 | >100 | >100 |
| B | 62357_14_D3_4589 | 39.918 | 38.031 | 69.460 | >100 |
| B | 6240_08_TA5_4622 | 8.092 | 6.599 | 12.632 | >100 |
| B | 6244_13_B5_4576 | 75.632 | 50.227 | >100 | >100 |
| B | 1006_11_C3_1601 | 1.890 | 2.353 | 3.304 | 7.429 |
| B | 1012_11_TC21_3257 | 0.305 | 0.167 | 0.260 | 0.303 |
| B | 1054_07_TC4_1499 | >100 | >100 | >100 | >100 |
| B | 1056_10_TA11_1826 | 3.572 | 3.614 | 6.032 | 13.517 |
| B | AC10.0.29 | 1.100 | 0.298 | 0.776 | 2.195 |
| B | CAAN5342.A2 | >100 | 70.060 | >100 | >100 |
| B | PVO.4 | 5.572 | 7.700 | 11.794 | 13.625 |
| B | QH0692.42 | >100 | >100 | >100 | >100 |
| B | REJO4541.67 | 0.005 | 0.003 | 0.008 | 0.017 |
| B | RHPA4259.7 | 1.856 | 0.578 | 1.431 | 1.964 |
| B | SC05_8C11_2344 | 14.458 | 4.245 | 9.440 | 17.835 |
| B | SC422661.8 | 5.326 | 5.331 | 6.257 | 62.835 |
| B | THRO4156.18 | n.t. | n.t. | n.t. | n.t. |
| B | TRJO4551.58 | >100 | >100 | >100 | >100 |
| B | TRO.11 | 1.259 | 0.652 | 1.408 | 0.823 |
| B | WEAU_d15_410_5017 | 0.003 | 0.009 | 0.012 | 0.300 |
| B | WITO4160.33 | 0.015 | 0.009 | 0.013 | 0.013 |
| BC | CNE17 | 0.028 | 0.010 | 0.031 | 0.018 |
| BC | CNE19 | 0.012 | 0.012 | 0.013 | 0.019 |
| BC | CNE20 | 0.015 | 0.008 | 0.015 | 0.021 |
| BC | CNE21 | 0.007 | 0.007 | 0.006 | 0.011 |
| BC | CNE30 | >100 | >100 | >100 | >100 |
| BC | CNE52 | 24.568 | 7.393 | 11.330 | >100 |
| BC | CNE53 | 0.081 | 0.029 | 0.059 | 0.105 |
| BC | CNE58 | 0.015 | 0.008 | 0.014 | 0.010 |
| C | 1394C9G1(Rev-) | 0.009 | 0.005 | 0.011 | 0.012 |
| C | 246FC1G | >100 | >100 | >100 | >100 |
| C | 249MB10 | 0.045 | 0.028 | 0.130 | 0.085 |
| C | 7030102001E5(Rev-) | >100 | >100 | >100 | >100 |
| C | BF1266.431a | 0.014 | 0.008 | 0.016 | 0.024 |
| C | CAP210.2.00.E8 | 0.226 | 0.221 | 0.538 | 1.321 |
| C | CAP45.2.00.G3 | 0.004 | 0.005 | 0.007 | 0.005 |
| C | Ce0393_C3 | 0.063 | 0.017 | 0.022 | 0.037 |
| C | Ce0682_E4 | 0.021 | 0.022 | 0.043 | 0.037 |
| C | Ce1086_B2 | n.t. | n.t. | n.t. | n.t. |
| C | Ce1172_H1 | 0.065 | 0.108 | 0.242 | 0.872 |
| C | Ce1176_A3 | 0.088 | 0.089 | 0.124 | 2.104 |
| C | Ce2010_F5 | >100 | >100 | >100 | >100 |
| C | Ce2060_G9 | 0.044 | 0.538 | 0.071 | 0.099 |
| C | Ce703010054_2A2 | 0.034 | 0.032 | 0.031 | 0.057 |
| C | Ce704809221_1B3 | 0.749 | 0.539 | 1.357 | 1.281 |
| C | Du156.12 | 0.026 | 0.016 | 0.026 | 0.025 |
| C | Du172.17 | 5.978 | 3.459 | 5.999 | 21.667 |
| C | Du422.1 | 34.557 | 53.230 | >100 | >100 |
| C | HIV-0013095-2.11 | >100 | >100 | >100 | >100 |
| C | HIV-001428-2.42 | 0.013 | 0.008 | 0.011 | 0.054 |
| C | HIV-16055-2.3 | 0.007 | 0.006 | 0.011 | 0.013 |
| C | HIV-16845-2.22 | >100 | >100 | >100 | >100 |
| C | ZM109F.PB4 | 0.121 | 0.106 | 0.196 | 0.390 |
| C | ZM135M.PL10a | >100 | >100 | >100 | >100 |
| C | ZM197M.PB7 | 0.141 | 0.092 | 0.240 | 0.282 |
| C | ZM214M.PL15 | >100 | >100 | >100 | >100 |
| C | ZM233M.PB6 | 0.007 | 0.007 | 0.006 | 0.007 |
| C | ZM247v1(Rev-) | n.t. | n.t. | n.t. | n.t. |
| C | ZM249M.PL1 | 0.138 | 0.008 | 0.056 | 0.101 |
| C | ZM53M.PB12 | 0.022 | 0.026 | 0.022 | 0.034 |
| CD | 3817.v2.c59 | 0.929 | 0.640 | 55.880 | >100 |
| CD | 6480.v4.c25 | >100 | >100 | >100 | >100 |
| CD | 6811.v7.c18 | >100 | >100 | >100 | >100 |
| CD | 6952.v1.c20 | 0.132 | 0.210 | 0.318 | 7.033 |
| CD | 89-F1_2_25 | 0.006 | 0.004 | 0.006 | 0.013 |
| D | 191821_E6_1 | n.t. | n.t. | n.t. | n.t. |
| D | 231965.c01 | 0.035 | 0.037 | 0.058 | 0.242 |
| D | 3016.v5.c45 | >100 | >100 | >100 | >100 |
| D | A07412M1.vrc12 | 0.035 | 0.103 | 0.118 | 0.115 |
| G | P0402_C2_11 | 0.015 | 0.003 | 0.006 | 0.027 |
| G | P1981_C5_3 | 1.179 | 0.585 | 1.277 | 75.570 |
| G | X1193_C1 | 0.156 | 0.158 | 0.381 | 0.374 |

-continued

| | | | | | |
|---|---|---|---|---|---|
| G | X1254_C3 | 0.869 | 0.710 | 2.070 | >100 |
| G | X1632_S2_B10 | 0.012 | 0.010 | 0.013 | 0.135 |
| G | X2088_C9 | >100 | >100 | >100 | >100 |
| G | X2131_C1_B5 | NT | NT | NT | NT |

Improved variant ePGDM14009 was tested for neutralization breadth and potency on a 100-member clade C pseudovirus panel in comparison to parental antibody PGDM1400. FIG. 1 shows neutralization breadth at different IC50 and IC80 cutoffs.

| Virus ID | IC50 (μg/ml) | IC80 (μg/ml) |
|---|---|---|
| Du422.1 | >50 | >50 |
| ZM197M.PB7 | 0.017 | 0.050 |
| ZM214M.PL15 | >50 | >50 |
| ZM233M.PB6 | <0.0006 | 0.001 |
| ZM135M.PL10a | >50 | >50 |
| CAP45.2.00.G3 | <0.0006 | <0.0006 |
| CAP244.2.00.D3 | 2.868 | 19.903 |
| ZM215F.PB8 | <0.0006 | 0.007 |
| ZM106F.PB9 | 0.007 | 0.024 |
| 0041.v3.c18 | <0.0006 | 0.001 |
| 0984.v2.c2 | 2.811 | >50 |
| 6040.v4.c15 | <0.0006 | 0.003 |
| 6631.v3.c10 | >50 | >50 |
| 933.v4.c4 | >50 | >50 |
| 6980.v0.c31 | <0.0006 | 0.006 |
| 3426.v5.c17 | <0.0006 | 0.002 |
| Ce1172_H1 | 0.007 | 0.020 |
| Ce703010131_1E2 | <0.0006 | 0.004 |
| Ce703010054_2A2 | 0.005 | 0.027 |
| Ce0665_F2 | 22.433 | >50 |
| Ce2052_G10 | 0.001 | 0.005 |
| Ce704810053_2B7 | 0.003 | 0.007 |
| CeCAP210_TA5 | 0.009 | 0.073 |
| CeCAP200_B8a | 0.003 | 0.022 |
| CeCAP188_1_D1_14(Rev-) | >50 | >50 |
| CeCAP177_1A3 | 0.153 | 1.065 |
| ZM249M.PL1 | 0.004 | 0.050 |
| 7060101641A7(Rev-) | 0.002 | 0.013 |
| 235080_3G7env2(Rev-) | 0.002 | 0.005 |
| 704010042 | <0.0006 | <0.0006 |
| 705010185 | 0.706 | 2.153 |
| 1245045 | 0.002 | 0.006 |
| 19157834_V1 | 31.667 | >50 |
| 2969249 | >50 | >50 |
| 3514597 | 0.003 | 0.011 |
| 20258279_V2 | >50 | >50 |
| 20915593 | 0.004 | 0.015 |
| 20927783 | 0.005 | 0.017 |
| 20965238 | >50 | >50 |
| 21197826_V1 | 12.688 | 34.637 |
| 21283649 | 1.547 | >50 |
| 2768732_C5_16 | 0.016 | 0.114 |
| 18814602_H8_F3 | <0.0006 | 0.002 |
| 19252094_A5_G2 | 0.001 | 0.003 |
| 19707346_E8_C6 | 0.005 | 0.014 |
| 20104663_E11_D2 | <0.0006 | 0.001 |
| 20198102_E9_G1 | 0.007 | 0.021 |
| 20286961_C1_H8 | 0.023 | >50 |
| 20883229_C9_H6 | >50 | >50 |
| 21203310_G7_C3 | 9.939 | >50 |
| 21492713_B11_E3 | >50 | >50 |
| 21502011_F12_E2 | >50 | >50 |
| 21561324_D3_B5 | 0.004 | 0.038 |
| 19314479_A2_5 | <0.0006 | 0.001 |
| 234-F1-16-57 | <0.0006 | 0.002 |
| 541-F1_A7_2 | 0.005 | 0.020 |
| 569-F1_37_10 | >50 | >50 |
| 556_F2_3_25 | >50 | >50 |
| CAP69.1.12_TA7.1 | 0.010 | 0.039 |
| CAP136.1.16_E6_1 | >50 | >50 |
| CAP174.1.06_F3_1B | 12.608 | >50 |
| CAP225.1.06_A2_18 | 0.025 | 0.167 |

-continued

| Virus ID | IC50 (μg/ml) | IC80 (μg/ml) |
|---|---|---|
| CAP266.2.00_E9_h6 | 0.008 | 0.037 |
| TRP290.2.00_23_6 | 0.012 | 0.060 |
| TRP307.2.00_24_1 | >50 | >50 |
| TRP363.2.00_10_3 | 1.810 | >50 |
| 722_G4_16 | 0.198 | 0.585 |
| So431_C1_1 | >50 | >50 |
| So405_T24_5 | 14.318 | >50 |
| CT072_56_7 | 0.002 | 1.230 |
| CT966_E1-7 | <0.0006 | 0.003 |
| CT140_140_B6 | 0.248 | 1.834 |
| Ko426_T78_10 | >50 | >50 |
| Ko459_T68_4 | 0.003 | 0.126 |
| Ko870_C2_10 | 0.001 | 0.021 |
| CA392_H2_6 | 0.032 | 0.129 |
| CA146_H3_3 | >50 | >50 |
| CA240_A5.5 | >50 | >50 |
| 2865_A11.12 | 0.071 | 0.258 |
| 3603_C11.13 | 0.654 | 2.173 |
| 3312_D6.2 | 0.004 | 0.011 |
| CAP304.2.00_F6.6 | 0.002 | 0.013 |
| CAP308.2.00_E11.35 | 0.001 | 0.004 |
| CAP323.2.00_B6.45 | 0.004 | 0.016 |
| CAP330.2.00_F2.41 | <0.0006 | 0.004 |
| 20417927.07 | 0.030 | 0.679 |
| 20358510.01 | 0.004 | 0.017 |
| 1170887.08 | 0.008 | 0.056 |
| B005018-8_F6.3 | <0.0006 | 0.003 |
| CT810_G4-7 | 0.087 | 5.530 |
| CT184_D3.15 | <0.0006 | 0.002 |
| SO607_B6.9 | 29.494 | >50 |
| Me178_G6.16 | 0.006 | 0.031 |
| CAP291.2.00_H2.15 | 0.342 | 1.097 |
| SO032_A2.8-1 | >50 | >50 |
| CT565_C7.48 | <0.0006 | 0.086 |
| CH0505.w4.3 | 0.001 | 0.011 |
| 6022.v7.c24 | >50 | >50 |
| 6146.v7.c23 | 0.019 | 0.249 |
| CH064.env | 0.333 | 1.619 |
| MuLV (Neg. Control) | >50 | >50 |

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. An antibody or antigen binding fragment thereof capable of binding HIV gp120, wherein the antibody or antigen binding fragment thereof comprises a VH and a VL, wherein the VH comprises a VH CDR1, VH CDR2, and VH CDR3, and the VL comprises a VL CDR1, VL CDR2, and VL CDR3, wherein a) the VH CDR1, VH CDR2, and VH CDR3 comprises the sequence of SEQ ID NO: 37, 38, and 31; SEQ ID NO: 37, 38, and 32; SEQ ID NO: 37, 38, and 33; SEQ ID NO: 37, 38, and 34; SEQ ID NO: 37, 38, and 35; or SEQ ID NO: 37, 39, and 31, respectively; and b) the VL CDR1, VL CDR2 and VLCDR3 comprises the sequence of SEQ ID NO: 41, 46, and 30, respectively; SEQ ID NO: 42, 45, and 30, respectively; SEQ ID NO: 41, 45, and 30, respectively; SEQ ID NO: 43, 45, and 30, respectively; SEQ ID NO: 43, 46, and 30, respectively; or SEQ ID NO: 44, 45, and 30, respectively.

2. The antibody or antigen binding fragment thereof of claim 1, wherein a) the VH CDR1, VH CDR2, and VH CDR3 comprises the sequence of SEQ ID NO: 37, 38, and 34; and b) the VL CDR1, VL CDR2 and VLCDR3 comprises the sequence of SEQ ID NO: 43, 45, and 30, respectively; or SEQ ID NO: 44, 45, and 30, respectively.

3. The antibody or antigen binding fragment thereof of claim 1, wherein the VH has at least 95% sequence identity to SEQ ID NO: 3-12; and the VL has at least 95% sequence identity to SEQ ID NO: 13-28.

4. The antibody or antigen binding fragment thereof of claim 1, wherein the antibody comprises a VH having at least about 90% sequence identity to SEQ ID NO: 1 and a VL having at least about 90% sequence identity SEQ ID NO: 2, wherein (i) the VH comprises one or more of a A at H2, Q at H3, V at H5, A at H9, A at H16, N at H24, T at H30, Q at H39, E at H46, Q at H54, E at H56, A at H58, K at H60, QGR at H62-H64, D at H66, G at H81, E at H85, E at H100H, E at H100M, Y at H100N, E at H100P, and A at H104, wherein the VH residues are numbered according to Kabat; and (ii) the VL comprises one or more of a I at L2, L at L9, P at L18, D at L26, Q at L27, Q or L at L27C, L at L37, K or Q at L42, L at L48, D at L49, G at L51, E or D at L53, E or R at L68, S at L74, D at L76, and A at L80, wherein the VL residues are numbered according to Kabat.

5. The antibody or antigen binding fragment thereof of claim 2, wherein the antibody comprises (i) a VH comprising the amino acid sequence of SEQ ID NO: 9 and a VL comprising the amino acid sequence of SEQ ID NO: 17;

(ii) a VH comprising the amino acid sequence of SEQ ID NO: 9 and a VL comprising the amino acid sequence of SEQ ID NO: 21; or (iii) a VH comprising the amino acid sequence of SEQ ID NO: 9 and a VL comprising the amino acid sequence of SEQ ID NO: 25.

6. The antibody or antigen binding fragment thereof of claim 2, which is capable of competing with PGDM1400 for binding to HIV gp120.

7. The antibody or antigen binding fragment thereof of claim 2, wherein the HIV gp120 is BG505 gp120.

8. The antibody or antigen binding fragment thereof of claim 2 capable of neutralizing at least two cross-clade isolates of HIV.

9. The antibody or antigen binding fragment thereof of claim 2, wherein the antibody is characterized by one or more of (i) the antibody is a recombinant antibody, a chimeric antibody, a bispecific antibody, or a trispecific antibody;

(ii) the antibody is a bispecific antibody;

(iii) the antibody is a trispecific antibody;

(iv) the antibody is an antibody fragment, which comprises a single-chain Fv (scFv), F(ab) fragment, F(ab')2 fragment, or an isolated VH domain;

(v) the antibody further comprises a heavy and/or light chain constant region;

(vi) the antibody further comprises a human heavy and/or light chain constant region;

(vii) the antibody further comprises a human heavy and/or light chain constant region, wherein the heavy chain constant region is human immunoglobulin IgG1, IgG2, IgG3, IgG4, IgA1, or IgA2 constant region; and (viii) the antibody further comprises a human heavy and/or light chain constant region, wherein the heavy chain constant region comprises a variant amino acid sequence.

10. The antibody or antigen binding fragment thereof of claim 3, wherein the antibody comprises (i) a VH comprising an amino acid sequence having at least 95% sequence identity to SEQ ID NO: 9 and a VL comprising an amino acid sequence having at least 95% sequence identity to SEQ ID NO: 17;

(ii) a VH comprising the amino acid sequence of SEQ ID NO: 9 and a VL comprising an amino acid sequence having at least 95% sequence identity to SEQ ID NO: 21; or (iii) a VH comprising an amino acid sequence having at least 95% sequence identity to SEQ ID NO: 9 and a VL comprising an amino acid sequence having at least 95% sequence identity to SEQ ID NO: 25.

11. A pharmaceutical composition comprising the antibody or antigen binding fragment thereof of claim 2 and a pharmaceutically acceptable excipient.

12. A method of neutralizing an HIV virus comprising contacting the virus with a sufficient amount of the antibody or antigen binding fragment thereof of claim 5.

13. A method of reducing the likelihood of HIV infection in a subject in need thereof comprising administering to the subject a sufficient amount of the antibody or antigen binding fragment thereof of claim 5.

14. A method of slowing down, lessening symptoms of, or halting progression of HIV/AIDS in a subject in need thereof comprising administering to the subject a sufficient amount of the antibody or antigen binding fragment thereof of claim 5.

15. A method of reducing HIV viral load in a subject in need thereof comprising administering to the subject a sufficient amount of the antibody or antigen binding fragment thereof of claim 5.

16. The method of claim 15, further comprising administering at least one additional therapeutic agent.

17. The method of claim 14, further comprising administering at least one additional therapeutic agent.

* * * * *